(12) United States Patent
Martinez-Sobrido et al.

(10) Patent No.: US 10,973,903 B2
(45) Date of Patent: Apr. 13, 2021

(54) NS1 TRUNCATED VIRUS FOR THE DEVELOPMENT OF CANINE INFLUENZA VACCINES

(71) Applicants: University of Rochester, Rochester, NY (US); Cornell University, Ithaca, NY (US)

(72) Inventors: Luis Martinez-Sobrido, Rochester, NY (US); Aitor Nogales-Gonzalez, Rochester, NY (US); Colin Parrish, Ithaca, NY (US)

(73) Assignees: University of Rochester, Rochester, NY (US); Cornell University, Ithaca, NY (US)

( * ) Notice: Subject to any disclaimer, the term of this patent is extended or adjusted under 35 U.S.C. 154(b) by 434 days.

(21) Appl. No.: 15/753,676

(22) PCT Filed: Aug. 19, 2016

(86) PCT No.: PCT/US2016/047711
§ 371 (c)(1),
(2) Date: Feb. 20, 2018

(87) PCT Pub. No.: WO2017/031401
PCT Pub. Date: Feb. 23, 2017

(65) Prior Publication Data
US 2020/0206341 A1 Jul. 2, 2020

Related U.S. Application Data

(60) Provisional application No. 62/207,576, filed on Aug. 20, 2015.

(51) Int. Cl.
*A61K 39/145* (2006.01)
*C12N 15/113* (2010.01)
*A61K 39/00* (2006.01)

(52) U.S. Cl.
CPC ........ *A61K 39/145* (2013.01); *C12N 15/1131* (2013.01); *A61K 2039/5254* (2013.01); *A61K 2039/552* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 7,722,884 B2 | 5/2010 | Shields et al. | |
| 8,137,676 B2 * | 3/2012 | Palese | C12N 7/00 424/206.1 |
| 9,345,758 B2 * | 5/2016 | Crawford | C12N 15/86 |
| 2010/0285063 A1 * | 11/2010 | Cho | A61K 39/12 424/209.1 |
| 2011/0150912 A1 | 6/2011 | Perez | |
| 2018/0243401 A1 | 8/2018 | Martinez-Sobrido et al. | |
| 2018/0256703 A1 | 8/2018 | Martinez-Sobrido et al. | |

FOREIGN PATENT DOCUMENTS

WO 2011/044561 A1 4/2011

OTHER PUBLICATIONS

Wang et al., Journal of Virology, 2002, vol. 76, No. 24, pp. 12951-12962.*
GenBank Accession # ADN86784, nonstructural protein 1 [Influenza A virus (A/canine/NY/dog23c02/2009(H3N8))], 2010.*
Baker et al., 2015, "Downregulating viral gene expression: codon usage bias manipulation for the generation of novel influenza A virus vaccines." Future Virology, 10: 715-730.
Varghese et al., 1992, "The structure of the complex between influenza virus neuraminidase and sialic acid, the viral receptor." Proteins, 14: -327-332.
Crawford et al., 2005, "Transmission of equine influenza virus to dogs." Science, 310: 482-485.
Song et al., 2008, "Transmission of avian influenza virus (H3N2) to dogs." Emerging Infectious Diseases, 14: 741-746.
JAVMA News. 2015. Outbreak of canine influenza caused by new strain of virus. J Am Vet Med Assoc. 246:1049-1049.
Jeoung et al., 2013, "A novel canine influenza H3N2 virus isolated from cats in an animal shelter." Veterinary Microbiology, 165: 281-286.
Song et al., 2011, "Interspecies transmission of the canine influenza H3N2 virus to domestic cats in South Korea, 2010." The Journal of General Virology, 92: 2350-2355.
Yoon et al., 2005, "Influenza virus infection in racing greyhounds." Emerging Infectious Diseases, 11: 1974-1976.
Holt et al., 2010, "Serologic prevalence of antibodies against canine influenza virus (H3N8) in dogs in a metropolitan animal shelter." Journal of the American Veterinary Medical Association, 237: 71-73.
Pecoraro et al., 2013, "Evaluation of virus isolation, one-step real-time reverse transcription polymerase chain reaction assay, and two rapid influenza diagnostic tests for detecting canine Influenza A virus H3N8 shedding in dogs." Journal of Veterinary Diagnostic Investigation, 25: 402-406.
Gonzalez et al., 2014, "Infection and pathogenesis of canine, equine, and human influenza viruses in canine tracheas." J Virol, 88: 9208-9219.
Song et al., 2015, "Canine susceptibility to human influenza viruses (A/pdm 09H1N1, A/H3N2 and B)." The Journal of General Virology, 96: 254-258.
Song et al., 2012, "A novel reassortant canine H3N1 influenza virus between pandemic H1N1 and canine H3N2 influenza viruses in Korea." The Journal of General Virology, 93: 551-554.

(Continued)

*Primary Examiner* — Benjamin P Blumel
(74) *Attorney, Agent, or Firm* — Riverside Law LLP

(57) ABSTRACT

The present invention relates to compositions and methods for the treatment and prevention of canine influenza virus (CIV) and CIV-related pathology. The present invention is based on the development of mutant CIV, having one or more mutations in segment 8, which induces a CIV-specific immune response in a subject.

17 Claims, 12 Drawing Sheets

Specification includes a Sequence Listing.

(56) References Cited

OTHER PUBLICATIONS

Yen et al., 2009, "Pandemic influenza as a current threat." Current topics in microbiology and immunology, 333: 3-24.
Pica et al., 2013, "Toward a universal influenza virus vaccine: prospects and challenges." Annual Review of Medicine, 64: 189-202.
Wong et al., 2013, "Traditional and new influenza vaccines." Clinical Microbiology Reviews, 26: 476-492.
Belshe et al., 2007, "Live attenuated versus inactivated influenza vaccine in infants and young children." The New England Journal of Medicine, 356: 685-696.
Cox et al., 2008, "FluBlok, a recombinant hemagglutinin influenza vaccine." Influenza and other Respiratory Viruses: 2: 211-219.
Osterholm et al., 2012, "Efficacy and effectiveness of influenza vaccines: a systematic review and meta-analysis" The Lancet Infectious Diseases, 12: 36-44.
Pronker et al., 2012, "Development of new generation influenza vaccines: recipes for success?" Vaccine, 30: 7344-7347.
Belongia et al., 2009, "Effectiveness of inactivated influenza vaccines varied substantially with antigenic match from the 2004-2005 season to the 2006-2007 season." Journal of Infectious Diseases, 199: 159-167.
Gorse et al., 1991, "Superiority of live attenuated compared with inactivated influenza A virus vaccines in older, chronically ill adults." Chest, 100: 977-984.
Maassab., 1968, "Plaque formation of influenza virus at 25 degrees C." Nature, 219:645-646.
Cox et al., 1988, "Identification of sequence changes in the cold-adapted, live attenuated influenza vaccine strain, A/Ann Arbor/6/60 (H2N2)." Virology, 167:554-567.
Snyder et al., 1988, "Four viral genes independently contribute to attenuation of live influenza A/Ann Arbor/6/60 (H2N2) cold-adapted reassortant virus vaccines." J Virol, 62:488-495.
Chan et al., 2008, "The cold adapted and temperature sensitive influenza A/Ann Arbor/6/60 virus, the master donor virus for live attenuated influenza vaccines, has multiple defects in replication at the restrictive temperature." Virology, 380:304-311.
Cox et al., 2015, "Development of a mouse-adapted live attenuated influenza virus that permits in vivo analysis of enhancements to the safety of live attenuated influenza virus vaccine." J Virol, 89(6): 3421-3426.
Jin et al., 2004, "Imparting temperature sensitivity and attenuation in ferrets to A/Puerto Rico/8/34 influenza virus by transferring the genetic signature for temperature sensitivity from cold-adapted A/Ann Arbor/6/60." J Virol, 78:995-998.
Zhou et al., 2012, "Engineering temperature sensitive live attenuated influenza vaccines from emerging viruses." Vaccine, 30: 3691-3702.
Martinez-Sobrido et al., 2010, Journal of visualized experiments, 42; doi: 10.3791/2057.
Nogales et al., 2014, "Influenza A virus attenuation by codon deoptimization of the NS gene for vaccine development." J Virol, 88: 10525-10540.
Feng et al., 2015, "Equine and Canine Influenza H3N8 Viruses Show Minimal Biological Differences Despite Phylogenetic Divergence." J Virol, 89: 6860-6873.
Nogales et al., 2015, "Replication-competent influenza A viruses expressing a red fluorescent protein." Virology, 476: 206-216.
Jin et al., 2003, "Multiple amino acid residues confer temperature sensitivity to human influenza virus vaccine strains (FluMist) derived from cold-adapted A/Ann Arbor/6/60." Virology, 306: 18-24.
Nogales et al., 2016, "Rearrangement of Influenza Virus Spliced Segments for the Development of Live-Attenuated Vaccines." J Virol, 90: 6291-6302.
Maassab, 1999, Reviews in medical virology, 9: 237-244.
Murphy et al., 2002, "Principles underlying the development and use of live attenuated cold-adapted influenza A and B virus vaccines." Viral immunology, 15: 295-323.
Kohlmeier et al., 2009, "Immunity to respiratory viruses." Annual review of immunology, 27: 61-82.
Cheng et al., 2013, The Journal of infectious diseases, 208: 594-602.
De Villiers et al., 2009, "Efficacy and safety of a live attenuated influenza vaccine in adults 60 years of age and older." Vaccine, 28: 228-234.
Katsura et al., 2012, "A replication-incompetent virus possessing an uncleavable hemagglutinin as an influenza vaccine." Vaccine, 30: 6027-6033.
Victor et al., 2012, "A replication-incompetent PB2-knockout influenza A virus vaccine vector." J Virol, 86(8): 4123-4128.
Baker et al., 2013, "Protection against lethal influenza with a viral mimic." J Virol, 87: 8591-8605.
Guo et al., 2014, "Induction of CD8 T cell heterologous protection by a single dose of single-cycle infectious influenza virus" J Virol, 88: 12006-12016.
Powell et al., 2012, "Pseudotyped influenza A virus as a vaccine for the induction of heterotypic immunity." J Virol, 86: 13397-13406.
Uraki et al., 2013, "A novel bivalent vaccine based on a PB2-knockout influenza virus protects mice from pandemic H1N1 and highly pathogenic H5N1 virus challenges." J Virol, 87: 7874-7881.
Hayward et al., 2010, "Microevolution of canine influenza virus in shelters and its molecular epidemiology in the United States." J Virol, 84:12636-12645.
Rivailler et al., 2010, "Evolution of canine and equine influenza (H3N8) viruses co-circulating between 2005 and 2008." Virology, 408: 71-79.
Bean et al., 1992, "Evolution of the H3 influenza virus hemagglutinin from human and nonhuman hosts." J Virol, 66:1129-1138.
Both et al., 1983, "Antigenic drift in influenza virus H3 hemagglutinin from 1968 to 1980: multiple evolutionary pathways and sequential amino acid changes at key antigenic sites." J Virol, 48:52.
Bush et al., 1999, "Positive selection on the H3 hemagglutinin gene of human influenza virus A." Molecular biology and evolution, 16: 1457-1465.
De Jong et al., 2007, "Antigenic and genetic evolution of swine influenza A (H3N2) viruses in Europe." J Virol, 81: 4315-4322.
Epperson et al., 2013, Human infections with influenza A(H3N2) variant virus in the United States, 2011-2012. Clinical infectious diseases, 57 Suppl 1:S4-S11.
Hussain et al., 2010, "Comparison of egg and high yielding MDCK cell-derived live attenuated influenza virus for commercial production of trivalent influenza vaccine: in vitro cell susceptibility and influenza virus replication kinetics in permissive and semi-permissive cells." Vaccine, 28: 3848-3855.
Parrish et al., 2005, "The Origins of New Pandemic Viruses: The Acquisition of New Host Ranges by Canine Parvovirus and Influenza A Viruses" Annual review of microbiology, 59:553-586.
Parrish et al., 2015, "Influenza Virus Reservoirs and Intermediate Hosts: Dogs, Horses, and New Possibilities for Influenza Virus Exposure of Humans" J Virol, 89:2990-2994.
Belshe et al., 2000, "Correlates of Immune Protection Induced by Live, Attenuated, Cold-Adapted, Trivalent, Intranasal Influenza Virus Vaccine" The Journal of infectious diseases, 181:1133-1137.
Centers for Disease Control and Prevention, 2010, "Licensure of a High-Dose Inactivated Influenza Vaccine for Persons Aged ≥65 Years (Fluzone High-Dose) and Guidance for Use—United States, 2010" MMWR, 59(16):485-486.
Rimmelzwaan et al., 2007, "Influenza virus-specific cytotoxic T lymphocytes: a correlate of protection and a basis for vaccine development" Current opinion in biotechnology, 18:529-536.
Smith et al., 2009, "Origins and evolutionary genomics of the 2009 swine-origin H1N1 influenza A epidemic" Nature, 459:1122-1125.
Dundon et al., 2010, "Serologic Evidence of Pandemic (H1N1) 2009 Infection in Dogs, Italy" Emerging infectious diseases, 16:2019-2021.
Hale et al., 2008, "The multifunctional NS1 protein of influenza A viruses" The Journal of general virology, 89:2359-2376.
Lamb et al., 1980, "Mapping of the two overlapping genes for polypeptides NS1 and NS2 on RNA segment 8 of influenza virus genome" Proceedings of the National Academy of Sciences, 77:1857-1861.
Garcia-Sastre et al., 1998, "Influenza A Virus Lacking the NS1 Gene Replicates in Interferon-Deficient Systems" Virology, 252:324-330.

(56) References Cited

OTHER PUBLICATIONS

Steidle et al., 2010, "Glycine 184 in Nonstructural Protein NS1 Determines the Virulence of Influenza A Virus Strain PR8 without Affecting the Host Interferon Response" J Virol, 84:12761-12770.
Geiss et al., 2002, "Cellular transcriptional profiling in influenza A virus-infected lung epithelial cells: The role of the nonstructural NS1 protein in the evasion of the host innate defense and its potential contribution to pandemic influenza" Proceedings of the National Academy of Sciences, 99:10736-10741.
Falcon et al., 2005, "Attenuation and immunogenicity in mice of temperature-sensitive influenza viruses expressing truncated NS1 proteins" The Journal of general virology, 86:2817-2821.
Ferko et al., 2004, "Immunogenicity and Protection Efficacy of Replication-Deficient Influenza A Viruses with Altered NS1 Genes" J Virol, 78:13037-13045.
Quinlivan et al., 2005, "Attenuation of Equine Influenza Viruses through Truncations of the NS1 Protein" J Virol, 79:8431-8439.
Richt et al., 2009, "Attenuated Influenza Virus Vaccines with Modified NS1 Proteins" Current topics in microbiology and immunology, 333:177-195.
Steel et al., 2009, "Live Attenuated Influenza Viruses Containing NS1 Truncations as Vaccine Candidates against H5N1 Highly Pathogenic Avian Influenza" J Virol 83:1742-1753.
Vincent et al., 2007, "Efficacy of intranasal administration of a truncated NS1 modified live influenza virus vaccine in swine" Vaccine 25:7999-8009.
Richt et al., 2006, "Vaccination of Pigs against Swine Influenza Viruses by Using an NS1-Truncated Modified Live-Virus Vaccine" J Virol 80:11009-11018.
Solorzano et al., 2005, "Mutations in the NS1 Protein of Swine Influenza Virus Impair Anti-Interferon Activity and Confer Attenuation in Pigs" J Virol, 79:7535-7543.
Choi et al., 2015, "Development of a dual-protective live attenuated vaccine against H5N1 and H9N2 avian influenza viruses by modifying the NS1 gene" Archives of virology, 160:1729-1740.
Wang et al., 2008, "Characterization of influenza virus variants with different sizes of the non-structural (NS) genes and their potential as a live influenza vaccine in poultry" Vaccine, 26:3580-3586.
Baskin et al., 2007, "Functional Genomic and Serological Analysis of the Protective Immune Response Resulting from Vaccination of Macaques with an NS1-Truncated Influenza Virus" J Virol, 81:11817-11827.
Pica et al., 2012, "NS1-Truncated Live Attenuated Virus Vaccine Provides Robust Protection to Aged Mice from Viral Challenge" J Virol, 86:10293-10301.
Hai et al., 2008, "Influenza B Virus NS1-Truncated Mutants: Live-Attenuated Vaccine Approach" J Virol, 82:10580-10590.
Talon et al., 2000, "Influenza A and B viruses expressing altered NS1 proteins: A vaccine approach" Proceedings of the National Academy of Sciences, 97:4309-4314.
Martinez-Sobrido et al., 2009, "Identification of Amino Acid Residues Critical for the Anti-Interferon Activity of the Nucleoprotein of the Prototypic Arenavirus Lymphocytic Choriomeningitis Virus" J Virol, 83:11330-11340.
Martinez-Sobrido et al., 2006, "Inhibition of the type I interferon response by the nucleoprotein of the prototypic arenavirus lymphocytic choriomeningitis virus" J Virol, 80:9192-9199.
Park et al., 2003, "Newcastle Disease Virus (NDV)-Based Assay Demonstrates Interferon-Antagonist Activity for the NDV V Protein and the Nipah Virus V, W, and C Proteins" J Virol, 77:1501-1511.
Deshpande et al., 2009, "Evaluation of the Efficacy of a Canine Influenza Virus (H3N8) Vaccine in Dogs Following Experimental Challenge" Veterinary therapeutics: research in applied veterinary medicine, 10:103-112.
Newbury et al., 2016, "Prolonged intermittent virus shedding during an outbreak of canine influenza A H3N2 virus infection in dogs in three Chicago area shelters: 16 cases (Mar.-May 2015)" Journal of the American Veterinary Medical Association, 248:1022-1026.
Ramirez-Martinez et al., 2013, "Evidence of transmission and risk factors for influenza A virus in household dogs and their owners" Influenza and other respiratory viruses, 7:1292-1296.
Randall et al., 2008, "Interferons and viruses: an interplay between induction, signalling, antiviral responses and virus countermeasures" The Journal of general virology, 89:1-47.
Solorzano et al., 2010, "Alternative Live-Attenuated Influenza Vaccines Based on Modifications in the Polymerase Genes Protect against Epidemic and Pandemic Flu." Journal of Virology, 84(9): 4587-4596.
Song et al., 2007, "A New Generation of Modified Live-Attenuated Avian Influenza Viruses Using a Two-Strategy Combination as Potential Vaccine Candidates." Journal of Virology, 81(17): 9238-9248.
Subbarao et al., 1995, "Sequential addition of temperature-sensitive missense mutations into the PB2 gene of influenza A transfectant viruses can effect an increase in temperature sensitivity and attenuation and permits the rational design of a genetically engineered live influenza a virus vaccine." Journal of Virology, 69(10): 5969-5977.
Hickman et al., 2008, "An avian live attenuated master backbone for potential use in epidemic and pandemic influenza vaccines." Journal of General Virology, 89(11): 2682-2690.
Mariana Baz et al., 2014, "A live attenuated H3N8 influenza vaccine is highly immunogenic and efficacious in mice and ferrets." Journal of Virology, 89(3): 1652-1659.
Kappes et al., 2011, "Vaccination with NS-1 truncated H3N2 swine influenza virus rimes T cells and confers cross-protection against an H1N1 heterosubtypic challenge in pigs." Vaccine, 30(2): 280-288.
Voorhees et al., "Spread of Canine Influenza A9H3N2) Virus, United States," Emerging Infectious Diseases, 23 (12):1950-1957, 2017.
Chao, "A Single Amino Acid Deletion at the Amino Terminus of Influenza Virus Hemagglutinin Causes Malfolding and Blocks Exocytosis of the Molecule in Mammalian Cells," The Journal of Biological Chemistry, 267(4)2142-2148, 1992.
Murphy et al., "An influenza A live attenuated reassortant virus possessing three temperature-sensitive mutations in the PB2 polymerase gene rapidly loses temperature sensitivity following replication in hamsters," Vaccine, 15 (12/13):1372-1378, 1997.
Hanson et al., "Canine Influenza," Clinicians Brief, University of Georgia, 97-103, 2016.
Suzuki et al., "Amino Acid Substitutions of PB1 of Avian Influenza Viruses Influence Pathogenicity and Transmissibility in Chickens," Journal of Virology, 88(19):11130-11139, 2014.

\* cited by examiner

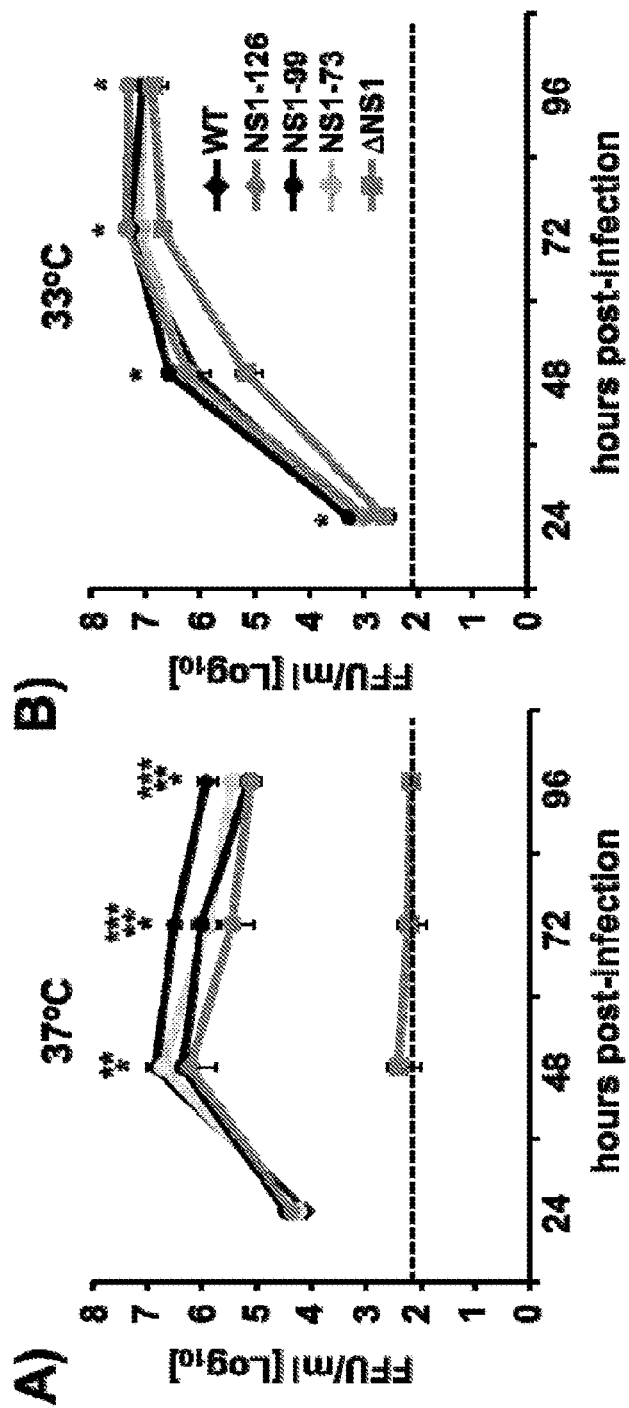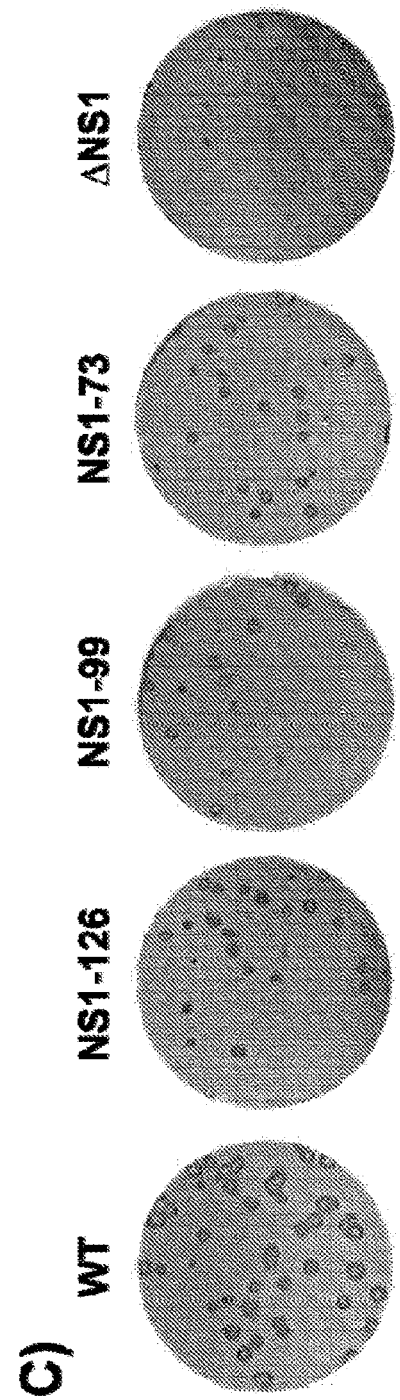
Figure 2A – Figure 2C

ΔNS1 - Nucleotide sequence of modified segment 8 - (SEQ ID NO: 1)
agcaaaagcagggtgacaaaaacataatggattccaacactgtgtcaagct
ttcaggacatactaatgaggatgtcaaaaatgcaattggggtcctcatcgg
aggatttaaatggaatgataatacggttaaaatctctgaaactctacagag
attcgcttggagaagcagtcatgagaatgggagaccttcactcccttcaaa
gcagaaacgaaaaatggagagaacaattaagccagaaatttgaagaaataa
gatggttgattgaagaagtgcgacatagactgaaaaatacagaaaatagtt
ttgaacaaataacatttatgcaagccttacaactattgcttgaagtagaac
aagagataagaactttctcgtttcagcttatttaatgataaaaaacaccct
tgtttctact

Figure 9

NS1-126 - Nucleotide sequence of modified segment 8 (SEQ ID NO: 2)

agcaaaagcagggtgacaaaaacataatggattccaacactgtgtcaagct
ttcaggtagactgttttctttggcatgtccgcaaacaattcgcagaccaag
aactgggtgatgccccattccttgaccggcttcgccgagaccagaagtccc
taaggggaagaggtagcactcttggtctggacatcgaaacagccactcatg
caggaaagcagatagtggagcagattctggaaaaggaatcagatgaggcac
ctaaaatgaccattgcctctgttcctgcttcacgctacttaactgacatga
ctcttgatgagatgtcaagagactggttcatgctcatgcccaagcaaaaag
taacaggctccctatgtataagaatggaccaggcaatcatggataagtaga
tcttgattaattaagaaggagcaatcgttggcgaaatttcaccattacctt
ctcttccaggacatactaatgaggatgtcaaaaatgcaattggggtcctca
tcggaggatttaaatggaatgataatacggttaaaatctctgaaactctac
agagattcgcttggagaagcagtcatgagaatgggagaccttcactccctt
caaagcagaaacgaaaaatggagagaacaattaagccagaaatttgaagaa
ataagatggttgattgaagaagtgcgacatagactgaaaaatacagaaaat
agttttgaacaaataacatttatgcaagccttacaactattgcttgaagta
gaacaagagataagaactttctcgtttcagcttatttaatgataaaaaaca
cccttgtttctact

Figure 10A

NS1-126 - Amino Acid Sequence (SEQ ID NO: 5)

MDSNTVSSFQVDCFLWHVRKQFADQELGDAPFLDRLRRDQKSLRGRGSTLG
LDIETATHAGKQIVEQILEKESDEAPKMTIASVPASRYLTDMTLDEMSRDW
FMLMPKQKVTGSLCIRMDQAIMDK

Figure 10B

NS1-99 - Nucleotide sequence of modified segment 8 (SEQ ID NO: 3)

```
agcaaaagcagggtgacaaaaacataatggattccaacactgtgtcaagct
ttcaggtagactgttttctttggcatgtccgcaaacaattcgcagaccaag
aactgggtgatgccccattccttgaccggcttcgccgagaccagaagtccc
taaggggaagaggtagcactcttggtctggacatcgaaacagccactcatg
caggaaagcagatagtggagcagattctggaaaaggaatcagatgaggcac
ctaaaatgaccattgcctctgttcctgcttcacgctacttaactgacatga
ctcttgatgagatgtcatgattaattaagaaggagcaatcgttggcgaaat
tcaccattccttctcttccaggacatactaatgaggatgtcaaaaatgc
aattggggtcctcatcggaggatttaaatggaatgataatacggttaaaat
ctctgaaactctacagagattcgcttggagaagcagtcatgagaatgggag
accttcactcccttcaaagcagaaacgaaaaatggagagaacaattaagcc
agaaatttgaagaaataagatggttgattgaagaagtgcgacatagactga
aaatacagaaatagttttgaacaaataacatttatgcaagccttacaac
tattgcttgaagtagaacaagagataagaactttctcgtttcagcttattt
aatgataaaaacaccttgtttctact
```

Figure 11A

NS1-99- Amino Acid Sequence (SEQ ID NO: 6)

MDSNTVSSFQVDCFLWHVRKQFADQELGDAPFLDRLRRDQKSLRGRGSTLG

LDIETATHAGKQIVEQILEKESDEAPKMTIASVPASRYLTDMTLDEMS

Figure 11B

NS1-73 - Nucleotide sequence of modified segment 8 (SEQ ID NO: 4)
```
agcaaaagcagggtgacaaaaacataatggattccaacactgtgtcaagct
ttcaggtagactgttttctttggcatgtccgcaaacaattcgcagaccaag
aactgggtgatgccccattccttgaccggcttcgccgagaccagaagtccc
taaggggaagaggtagcactcttggtctggacatcgaaacagccactcatg
caggaaagcagatagtggagcagattctggaaaaggaatcataagctttaa
ttaagaaggagcaatcgttggcgaaatttcaccattaccttctcttccagg
acatactaatgaggatgtcaaaaatgcaattggggtcctcatcggaggatt
taaatggaatgataatacggttaaatctctgaaactctacagagattcgc
ttggagaagcagtcatgagaatgggagaccttcactcccttcaaagcagaa
acgaaaaatggagagaacaattaagccagaaatttgaagaaataagatggt
tgattgaagaagtgcgacatagactgaaaaatacagaaaatagtttgaac
aaataacatttatgcaagccttacaactattgcttgaagtagaacaagaga
taagaactttctcgtttcagcttatttaatgataaaaaacaccttgtttc
tact
```

Figure 12A

NS1-73 - Amino Acid Sequence (SEQ ID NO: 7)
```
MDSNTVSSFQVDCFLWHVRKQFADQELGDAPFLDRLRRDQKSLRGRGSTLG
LDIETATHAGKQIVEQILEKES
```

Figure 12B

SEQUENCE LISTING

<160> NUMBER OF SEQ ID NOS: 30

<210> SEQ ID NO 1
<211> LENGTH: 418
<212> TYPE: DNA
<213> ORGANISM: Artificial Sequence
<220> FEATURE:
<223> OTHER INFORMATION: Chemically Synthesized

<400> SEQUENCE: 1
agcaaaagca gggtgacaaa aacataatgg attccaacac tgtgtcaagc tttcaggaca    60
tactaatgag gatgtcaaaa atgcaattgg ggtcctcatc ggaggattta aatggaatga   120
taatacggtt aaaatctctg aaactctaca gagattcgct tggagaagca gtcatgaaaa   180
tgggagacct tcactccctt caaagcagaa acgaaaaatg gagagaacaa ttaagccaga   240
aatttgaaga aataagatgg ttgattgaag aagtgcgaca tagactgaaa aatacagaaa   300
atagttttga acaaataaca tttatgcaag ccttacaact attgcttgaa gtagaacaag   360
agataagaac tttctcgttt cagcttattt aatgataaaa aacacccttg tttctact     418

<210> SEQ ID NO 2
<211> LENGTH: 830
<212> TYPE: DNA
<213> ORGANISM: Artificial Sequence
<220> FEATURE:
<223> OTHER INFORMATION: Chemically Synthesized

<400> SEQUENCE: 2
agcaaaagca gggtgacaaa aacataatgg attccaacac tgtgtcaagc tttcaggtag    60 actgtttttct ttggcatgtc cgcaaacaat tcgcagacca agaactgggt gatgccccat   120
tccttgaccg gcttcgccga gaccagaagt ccctaagggg aagaggtagc actcttggtc   180

```
tggacatcga aacagccact catgcaggaa agcagatagt ggagcagatt ctggaaaagg    240
aatcagatga ggcacctaaa atgaccattg cctctgttcc tgcttcacgc tacttaactg    300
acatgactct tgatgagatg tcaagagact ggttcatgct catgcccaag caaaaagtaa    360
caggctccct atgtataaga atggaccagg caatcatgga taagtagatc ttgattaatt    420
aagaaggagc aatcgttggc gaaatttcac cattaccttc tcttccagga catactaatg    480
aggatgtcaa aaatgcaatt ggggtcctca tcggaggatt taaatggaat gataatacgg    540
ttaaaatctc tgaaactcta cagagattcg cttggagaag cagtcatgag aatgggagac    600
cttcactccc ttcaaagcag aaacgaaaaa tggagagaac aattaagcca gaaatttgaa    660
gaaataagat ggttgattga agaagtgcga catagactga aaaatacaga aaatagtttt    720
gaacaaataa catttatgca agccttacaa ctattgcttg aagtagaaca agagataaga    780
actttctcgt ttcagcttat ttaatgataa aaaacaccct tgtttctact              830

<210> SEQ ID NO 3
<211> LENGTH: 742
<212> TYPE: DNA
<213> ORGANISM: Artificial Sequence
<220> FEATURE:
<223> OTHER INFORMATION: Chemically Synthesized

<400> SEQUENCE: 3
agcaaaagca gggtgacaaa acataatgg attccaacac tgtgtcaagc tttcaggtag      60
actgttttct ttggcatgtc cgcaaacaat tcgcagacca agaactgggt gatgccccat    120
tccttgaccg gcttcgccga gaccagaagt ccctaagggg aagaggtagc actcttggtc    180
tggacatcga aacagccact catgcaggaa agcagatagt ggagcagatt ctggaaaagg    240
aatcagatga ggcacctaaa atgaccattg cctctgttcc tgcttcacgc tacttaactg    300
acatgactct tgatgagatg tcatgattaa ttaagaagga gcaatcgttg gcgaaatttc    360 accattcct tctcttccag acatactaa tgaggatgtc aaaaatgcaa ttggggtcct    420
catcggagga tttaaatgga atgataatac ggttaaaatc tctgaaactc tacagagatt    480
cgcttggaga agcagtcatg agaatgggag accttcactc ccttcaaagc agaaacgaaa    540
aatggagaga acaattaagc cagaaatttg aagaaataag atggttgatt gaagaagtgc    600
gacatagact gaaaaataca gaaaatagtt ttgaacaaat aacatttatg caagccttac    660
aactattgct tgaagtagaa caagagataa gaactttctc gtttcagctt atttaatgat    720
aaaaaacacc cttgtttcta ct                                             742

<210> SEQ ID NO 4
<211> LENGTH: 667
<212> TYPE: DNA
<213> ORGANISM: Artificial Sequence
<220> FEATURE:
<223> OTHER INFORMATION: Chemically Synthesized

<400> SEQUENCE: 4
agcaaaagca gggtgacaaa acataatgg attccaacac tgtgtcaagc tttcaggtag      60
actgttttct ttggcatgtc cgcaaacaat tcgcagacca agaactgggt gatgccccat    120
tccttgaccg gcttcgccga gaccagaagt ccctaagggg aagaggtagc actcttggtc    180
tggacatcga aacagccact catgcaggaa agcagatagt ggagcagatt ctggaaaagg    240
aatcataagc tttaattaag aaggagcaat cgttggcgaa atttcaccat taccttctct    300
tccaggacat actaatgagg atgtcaaaaa tgcaattggg gtcctcatcg gaggatttaa    360
```

```
atggaatgat aatacggtta aaatctctga aactctacag agattcgctt ggagaagcag    420
tcatgagaat gggagacctt cactcccttc aaagcagaaa cgaaaaatgg agagaacaat    480
taagccagaa atttgaagaa ataagatggt tgattgaaga agtgcgacat agactgaaaa    540
atacagaaaa tagttttgaa caaataacat ttatgcaagc cttacaacta ttgcttgaag    600
tagaacaaga gataagaact ttctcgtttc agcttattta atgataaaaa acacccttgt    660
ttctact                                                              667
```

```
<210> SEQ ID NO 5
<211> LENGTH: 126
<212> TYPE: PRT
<213> ORGANISM: Artificial Sequence
<220> FEATURE:
<223> OTHER INFORMATION: Chemically Syntehsized

<400> SEQUENCE: 5

Met Asp Ser Asn Thr Val Ser Ser Phe Gln Val Asp Cys Phe Leu Trp
1               5                   10                  15

His Val Arg Lys Gln Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr His Ala Gly Lys Gln Ile
    50                  55                  60

Val Glu Gln Ile Leu Glu Lys Glu Ser Asp Glu Ala Pro Lys Met Thr
65                  70                  75                  80

Ile Ala Ser Val Pro Ala Ser Arg Tyr Leu Thr Asp Met Thr Leu Asp
                85                  90                  95

Glu Met Ser Arg Asp Trp Phe Met Leu Met Pro Lys Gln Lys Val Thr
            100                 105                 110

Gly Ser Leu Cys Ile Arg Met Asp Gln Ala Ile Met Asp Lys
        115                 120                 125
```

```
<210> SEQ ID NO 6
<211> LENGTH: 99
<212> TYPE: PRT
<213> ORGANISM: Artificial Sequence
<220> FEATURE:
<223> OTHER INFORMATION: Chemically Synthesized

<400> SEQUENCE: 6

Met Asp Ser Asn Thr Val Ser Ser Phe Gln Val Asp Cys Phe Leu Trp
1               5                   10                  15

His Val Arg Lys Gln Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr His Ala Gly Lys Gln Ile
    50                  55                  60

Val Glu Gln Ile Leu Glu Lys Glu Ser Asp Glu Ala Pro Lys Met Thr
65                  70                  75                  80

Ile Ala Ser Val Pro Ala Ser Arg Tyr Leu Thr Asp Met Thr Leu Asp
                85                  90                  95

Glu Met Ser
```

```
<210> SEQ ID NO 7
```

-continued

<211> LENGTH: 73
<212> TYPE: PRT
<213> ORGANISM: Artificial Sequence
<220> FEATURE:
<223> OTHER INFORMATION: Chemically Synthesized

<400> SEQUENCE: 7

```
Met Asp Ser Asn Thr Val Ser Ser Phe Gln Val Asp Cys Phe Leu Trp
1               5                   10                  15

His Val Arg Lys Gln Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr His Ala Gly Lys Gln Ile
    50                  55                  60

Val Glu Gln Ile Leu Glu Lys Glu Ser
65                  70
```

<210> SEQ ID NO 8
<211> LENGTH: 121
<212> TYPE: PRT
<213> ORGANISM: Artificial Sequence
<220> FEATURE:
<223> OTHER INFORMATION: Chemically Synthesized

<400> SEQUENCE: 8

```
Met Asp Ser Asn Thr Val Ser Ser Phe Gln Asp Ile Leu Met Arg Met
1               5                   10                  15

Ser Lys Met Gln Leu Gly Ser Ser Ser Glu Asp Leu Asn Gly Met Ile
            20                  25                  30

Ile Arg Leu Lys Ser Leu Lys Leu Tyr Arg Asp Ser Leu Gly Glu Ala
        35                  40                  45

Val Met Arg Met Gly Asp Leu His Ser Leu Gln Ser Arg Asn Glu Lys
    50                  55                  60

Trp Arg Glu Gln Leu Ser Gln Lys Phe Glu Glu Ile Arg Trp Leu Ile
65                  70                  75                  80

Glu Glu Val Arg His Arg Leu Lys Asn Thr Glu Asn Ser Phe Glu Gln
                85                  90                  95

Ile Thr Phe Met Gln Ala Leu Gln Leu Leu Leu Glu Val Glu Gln Glu
            100                 105                 110

Ile Arg Thr Phe Ser Phe Gln Leu Ile
        115                 120
```

<210> SEQ ID NO 9
<211> LENGTH: 2341
<212> TYPE: DNA
<213> ORGANISM: Influenza A virus (H3N8)

<400> SEQUENCE: 9

```
agcgaaagca ggtcaaatat attcaatatg gagagaataa aagaactgag agatctgatg      60
ttacaatccc gcacccgcga gatactaaca aaaactactg tagaccacat ggccataatc     120
aagaaataca catcaggaag acaagagaag aaccctgcac ttaggatgaa atggatgatg     180
gcaatgaaat acccaatcac agcagataag aggataatgg agatgattcc tgagagaaat     240
gaacagggac aaaccctttg gagcaaaacg aacgatgctg gctcagaccg cgtaatggta     300
tcacctctgg cagtaacatg gtggaatagg aatggaccaa caacgaacac aattcattat     360
ccaaaagtct acaaaactta ttttgaaaag gttgaaagat tgaaacacgg aacctttggc     420
```

```
cccgttcatt ttaggaatca agtcaaaata agacgaagag ttgatgtaaa ccctggtcac    480
gcggacctca gtgctaaaga agcacaagat gtgatcatgg aagttgtttt cccaaatgag    540
gtgggagccc gaattctaac atcggaatca caactaacaa taaccaagga gaaaaggaa     600 gaacttcagg actgcaaaat tgctcccttg atggtagcat acatgctaga aagagagttg    660
gtccgaaaaa caaggttcct cccagtagta ggcggaacaa gcagtatata cattgaagtg    720
ttgcatctga ctcagggaac atgctgggag caaatgtaca ccccaggagg agaagttaga    780
aacgatgata ttgatcaaag tttaattatt gcagcccgga acatagtgag aagagcgaca    840
gtatcagcag atccactagc atccctactg gaaatgtgcc acagtacaca aattggtgga    900
acaaggatga tagacatcct taagcagaac ccaacagagg aacaagctgt ggatatatgc    960
aaagcagcaa tgggattgag aattagctca tcattcagct ttggtggatt caccttcaaa   1020
aggacaagtg gatcatcagt caagagagaa gaagaaatgc ttacgggcaa ccttcaaaca   1080
ttgaaaataa gagtgcatga gggctatgaa gaattcacaa tggtcggaag aagagcaaca   1140
gccattatca gaaaggcaac cagaagattg attcaactga tagtaagtgg aaaagatgaa   1200
caatcaattg ctgaagcaat aattgtagcc atggtgtttt cgcaagaaga ttgcatgata   1260
aaagcagttc gaggcgattt gaactttgtt aatagagcaa atcagcgttt aaaccccatg   1320
catcaactct tgaggcattt ccaaaaagat gcaaagtgc ttttccaaaa ttggggaatt   1380
gaacccatcg acaatgtaat gggaatgatt ggaatactgc ctgacatgac cccaagcact   1440
gaaatgtcat tgagaggagt gagagtcagc aaaatgggag tggatgagta ctccagcact   1500
gagagagtgg tggtgagcat tgaccgtttt ttaagagttc gggatcaaag gggaaacata   1560
ctactgtccc ctgaagaagt cagtgaaaca caaggaacgg aaaagctgac aataatttat   1620
tcgtcatcaa tgatgtggga gattaatggt cccgaatcag tgttggtcaa tacttatcaa   1680
tggatcatca gaaactggga aaatgtaaaa attcagtggt cacaggaccc cacaatgtta   1740
tacaataaga tagaatttga gccattccaa tccctggtcc ctaggggccac cagaagccaa   1800 tacagcggtt ttgtaagaac cctgttttcag caaatgcgag atgtacttgg aacatttgat   1860
actgctcaaa aataaaaact cctccctttt gccgctgctc ctccggaaca gagtaggatg   1920
cagttctctt ctttgactgt taatgtaaga ggttcgggaa tgaggatact tgtaagaggc   1980
aattccccag tgttcaacta caataaagcc actaaaaggc tcacagtcct cggaaaagat   2040
gcgggtgcgc ttactgagga cccagatgaa ggtacggctg gagtagaatc cgctgttcta   2100
agagggtttc tcatcttagg taaagaaaac aagagatatg gcccagcact aagcatcaat   2160
gaacttagca aacttgcaaa aggggagaaa gccaatgtac taattgggca aggggacata   2220
gtgttggtaa tgaaacggaa acgtgactct agcatactta ctgacagcca gacagcgacc   2280
aaaaggattc ggatggccat caattagtgt taaattgttt aaaaacgacc ttgtttctac   2340
t                                                                   2341

<210> SEQ ID NO 10
<211> LENGTH: 759
<212> TYPE: PRT
<213> ORGANISM: Influenza A virus (H3N8)

<400> SEQUENCE: 10

Met Glu Arg Ile Lys Glu Leu Arg Asp Leu Met Leu Gln Ser Arg Thr
1               5                   10                  15

Arg Glu Ile Leu Thr Lys Thr Thr Val Asp His Met Ala Ile Ile Lys
            20                  25                  30
```

-continued

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Met
    50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Asn Thr Ile His Tyr Pro
                100                 105                 110

Lys Val Tyr Lys Thr Tyr Phe Glu Lys Val Glu Arg Leu Lys His Gly
            115                 120                 125

Thr Phe Gly Pro Val His Phe Arg Asn Gln Val Lys Ile Arg Arg Arg
    130                 135                 140

Val Asp Val Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ala Pro Leu Met Val Ala Tyr Met Leu Glu
    195                 200                 205

Arg Glu Leu Val Arg Lys Thr Arg Phe Leu Pro Val Val Gly Gly Thr
    210                 215                 220

Ser Ser Ile Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Ile Asp
                245                 250                 255

Gln Ser Leu Ile Ile Ala Ala Arg Asn Ile Val Arg Arg Ala Thr Val
            260                 265                 270

Ser Ala Asp Pro Leu Ala Ser Leu Leu Glu Met Cys His Ser Thr Gln
    275                 280                 285

Ile Gly Gly Thr Arg Met Ile Asp Ile Leu Lys Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Met Leu Thr Gly Asn Leu Gln Thr Leu
            340                 345                 350

Lys Ile Arg Val His Glu Gly Tyr Glu Glu Phe Thr Met Val Gly Arg
    355                 360                 365

Arg Ala Thr Ala Ile Ile Arg Lys Ala Thr Arg Arg Leu Ile Gln Leu
    370                 375                 380

Ile Val Ser Gly Lys Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
    435                 440                 445

Trp Gly Ile Glu Pro Ile Asp Asn Val Met Gly Met Ile Gly Ile Leu
450                 455                 460

Pro Asp Met Thr Pro Ser Thr Glu Met Ser Leu Arg Gly Val Arg Val
465                 470                 475                 480

Ser Lys Met Gly Val Asp Glu Tyr Ser Ser Thr Glu Arg Val Val
            485                 490                 495

Ser Ile Asp Arg Phe Leu Arg Val Arg Asp Gln Arg Gly Asn Ile Leu
            500                 505                 510

Leu Ser Pro Glu Glu Val Ser Glu Thr Gln Gly Thr Glu Lys Leu Thr
            515                 520                 525

Ile Ile Tyr Ser Ser Ser Met Met Trp Glu Ile Asn Gly Pro Glu Ser
            530                 535                 540

Val Leu Val Asn Thr Tyr Gln Trp Ile Ile Arg Asn Trp Glu Asn Val
545                 550                 555                 560

Lys Ile Gln Trp Ser Gln Asp Pro Thr Met Leu Tyr Asn Lys Ile Glu
            565                 570                 575

Phe Glu Pro Phe Gln Ser Leu Val Pro Arg Ala Thr Arg Ser Gln Tyr
            580                 585                 590

Ser Gly Phe Val Arg Thr Leu Phe Gln Gln Met Arg Asp Val Leu Gly
            595                 600                 605

Thr Phe Asp Thr Ala Gln Ile Ile Lys Leu Leu Pro Phe Ala Ala Ala
            610                 615                 620

Pro Pro Glu Gln Ser Arg Met Gln Phe Ser Ser Leu Thr Val Asn Val
625                 630                 635                 640

Arg Gly Ser Gly Met Arg Ile Leu Val Arg Gly Asn Ser Pro Val Phe
            645                 650                 655

Asn Tyr Asn Lys Ala Thr Lys Arg Leu Thr Val Leu Gly Lys Asp Ala
            660                 665                 670

Gly Ala Leu Thr Glu Asp Pro Asp Glu Gly Thr Ala Gly Val Glu Ser
            675                 680                 685

Ala Val Leu Arg Gly Phe Leu Ile Leu Gly Lys Glu Asn Lys Arg Tyr
690                 695                 700

Gly Pro Ala Leu Ser Ile Asn Glu Leu Ser Lys Leu Ala Lys Gly Glu
705                 710                 715                 720

Lys Ala Asn Val Leu Ile Gly Gln Gly Asp Ile Val Leu Val Met Lys
            725                 730                 735

Arg Lys Arg Asp Ser Ser Ile Leu Thr Asp Ser Gln Thr Ala Thr Lys
            740                 745                 750

Arg Ile Arg Met Ala Ile Asn
        755

<210> SEQ ID NO 11
<211> LENGTH: 2341
<212> TYPE: DNA
<213> ORGANISM: Influenza A virus (H3N8)

<400> SEQUENCE: 11
agcgaaagca ggcaaaccat ttgaatggat gtcaacccga ctctactttt cttaaaggtg    60
ccagcgcaaa atgctataag cacaacattc cctatactg gagatcctcc ctacagtcat   120
ggaacaggga caggatacac catggatact gtcaacagaa cgcaccaata ttcagaaaaa   180
gggaaatgga taacaaacac tgagattgga gcaccacaac ttaatccaat cgatggacca   240
cttcctgaag acaatgaacc aagtgggtac gcccaaacag attgtgtatt ggaagcaatg   300
gctttccttg aagaatccca tcccggaatc tttgaaaatt cgtgtcttga acaatggag   360

```
gtgattcagc agacaagagt ggacaaacta acacaaggcc gacaaactta tgattggacc    420
ttgaatagga atcaacctgc cgcaacagca cttgctaata cgattgaagt attcagatca    480
aatggtctga cttccaatga atcggggaga ttgatagact tcctcaaaga tgtcatggag    540
tccatgaaca aggaagaaat ggaataacaa cacacttcc aacggaagag aagagtaaga    600
gacaacatga caaagagaat gataacacag agaaccatag ggaagaaaaa caacgatta    660 aacagaaaga gctatctgat cagaacatta accctaaaca caatgaccaa ggacgctgag    720
agagggaaat tgaaacgacg agcaatcgct accccaggga tgcagataag aggatttgta    780
tattttgttg aaacactagc tcgaagaata tgtgaaaagc ttgaacaatc aggattgcca    840
gttggcggta atgagaaaaa agccaaactg gctaatgtcg tcagaaaaat gatgactaat    900
tcccaagaca ctgaactctc cttcaccatc actggggaca taccaaatg gaatgaaaat    960 cagaacccac gcatattcct ggcaatgatc acatacataa ctagaaatca gccagaatgg   1020
ttcagaaatg ttctaaacat tgcaccgatt atgttctcaa ataaaatggc aagactgggg   1080
aaaggatata tgtttgaaag caaaagtatg aaattgagaa ctcaaatacc agcagaaatg   1140
ctagcgagca ttgacctaaa atatttcaat gattcaacaa aaagaaaat tgaaagata   1200 cgaccactct tggttaacgg gactgcttca ctgagtcctg gcatgatgat gggaatgttc   1260
aacatgttga gcactgtgct gggtgtatcc atattaaacc tgggccagag gaaatataca   1320 aaaccacat actggtggga tggtctgcaa tcatcagatg actttgcttt gatagtgaat   1380
gcgcctaatc atgaaggaat acaagctgga gtagacagat tctatagaac ttgcaaactg   1440
gtcgggatca acatgagcaa aaagaagtcc tacataaata gaactggaac attcgaattc   1500
acaagctttt tctaccggta tggttttgta gccaatttca gcatggaact acccagtttt   1560
ggggtttccg gaataaatga atctgcagac atgagcattg gagtgacaat catcaaaaac   1620
aacatgataa ataatgatct cggtcctgcc acggcacaaa tggcactcca actcttcatt   1680
aaggattatc ggtacacata ccggtgccat agaggtgata cccagataca aaccagaaga   1740
tcttttgagt tgaagaaact ttgggaacag actcaatcaa agactggtct actgatatca   1800
gatgggggtc caaacctata taacatcaga aacctacaca tcccgaagt ctgtttaaag   1860 tgggagctaa tggatgaaga ttataagggg aggctatgca atccattgaa tcctttcgtt   1920
agtcacaaag aaattgaatc agtcaacagt gcagtagtaa tgcctgcgca tggccctgcc   1980
aaaagcatgg agtatgatgc tgttgcaaca acacattctt ggatccccaa gaggaaccgg   2040
tccatattga cacaagcca aaggggaata ctcgaagatg agcatatgta tcagaaatgc   2100
tgcaacctgt ttgaaaaatt ctttcccaagc agctcataca aagaccagtc cggaatttct   2160
agtatggttg aggccatggt atccagggcc cgcattgatg cacgaattga cttcgaatct   2220
ggacggataa agaaggatga gttcgctgag atcatgaaga tctgttccac cattgaagag   2280
ctcaaacggc aaaaatagtg aatttagctt gatcttcatg aaaaaatgcc ttgtttctac   2340
t                                                                  2341
```

<210> SEQ ID NO 12
<211> LENGTH: 757
<212> TYPE: PRT
<213> ORGANISM: Influenza A virus (H3N8)

<400> SEQUENCE: 12

```
Met Asp Val Asn Pro Thr Leu Leu Phe Leu Lys Val Pro Ala Gln Asn
1               5                   10                  15
```

```
Ala Ile Ser Thr Thr Phe Pro Tyr Thr Gly Asp Pro Tyr Ser His
         20                  25                  30

Gly Thr Gly Thr Gly Tyr Thr Met Asp Thr Val Asn Arg Thr His Gln
             35                  40                  45

Tyr Ser Glu Lys Gly Lys Trp Ile Thr Asn Thr Glu Ile Gly Ala Pro
     50                  55                  60

Gln Leu Asn Pro Ile Asp Gly Pro Leu Pro Glu Asp Asn Glu Pro Ser
 65                  70                  75                  80

Gly Tyr Ala Gln Thr Asp Cys Val Leu Glu Ala Met Ala Phe Leu Glu
                 85                  90                  95

Glu Ser His Pro Gly Ile Phe Glu Asn Ser Cys Leu Glu Thr Met Glu
                100                 105                 110

Val Ile Gln Gln Thr Arg Val Asp Lys Leu Thr Gln Gly Arg Gln Thr
             115                 120                 125

Tyr Asp Trp Thr Leu Asn Arg Asn Gln Pro Ala Ala Thr Ala Leu Ala
130                 135                 140

Asn Thr Ile Glu Val Phe Arg Ser Asn Gly Leu Thr Ser Asn Glu Ser
145                 150                 155                 160

Gly Arg Leu Ile Asp Phe Leu Lys Asp Val Met Glu Ser Met Asn Lys
                165                 170                 175

Glu Glu Met Glu Ile Thr Thr His Phe Gln Arg Lys Arg Arg Val Arg
            180                 185                 190

Asp Asn Met Thr Lys Arg Met Ile Thr Gln Arg Thr Ile Gly Lys Lys
            195                 200                 205

Lys Gln Arg Leu Asn Arg Lys Ser Tyr Leu Ile Arg Thr Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Arg Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
290                 295                 300

Asp Asn Thr Lys Trp Asn Glu Asn Gln Asn Pro Arg Ile Phe Leu Ala
305                 310                 315                 320

Met Ile Thr Tyr Ile Thr Arg Asn Gln Pro Glu Trp Phe Arg Asn Val
                325                 330                 335

Leu Asn Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
    370                 375                 380

Thr Lys Lys Lys Ile Glu Lys Ile Arg Pro Leu Leu Val Asn Gly Thr
385                 390                 395                 400

Ala Ser Leu Ser Pro Gly Met Met Gly Met Phe Asn Met Leu Ser
                405                 410                 415

Thr Val Leu Gly Val Ser Ile Leu Asn Leu Gly Gln Arg Lys Tyr Thr
            420                 425                 430
```

```
Lys Thr Thr Tyr Trp Trp Asp Gly Leu Gln Ser Ser Asp Phe Ala
            435                 440                 445
Leu Ile Val Asn Ala Pro Asn His Glu Gly Ile Gln Ala Gly Val Asp
    450                 455                 460
Arg Phe Tyr Arg Thr Cys Lys Leu Val Gly Ile Asn Met Ser Lys Lys
465                 470                 475                 480
Lys Ser Tyr Ile Asn Arg Thr Gly Thr Phe Glu Phe Thr Ser Phe Phe
                485                 490                 495
Tyr Arg Tyr Gly Phe Val Ala Asn Phe Ser Met Glu Leu Pro Ser Phe
            500                 505                 510
Gly Val Ser Gly Ile Asn Glu Ser Ala Asp Met Ser Ile Gly Val Thr
        515                 520                 525
Ile Ile Lys Asn Asn Met Ile Asn Asn Asp Leu Gly Pro Ala Thr Ala
    530                 535                 540
Gln Met Ala Leu Gln Leu Phe Ile Lys Asp Tyr Arg Tyr Thr Tyr Arg
545                 550                 555                 560
Cys His Arg Gly Asp Thr Gln Ile Gln Thr Arg Arg Ser Phe Glu Leu
                565                 570                 575
Lys Lys Leu Trp Glu Gln Thr Gln Ser Lys Thr Gly Leu Leu Ile Ser
            580                 585                 590
Asp Gly Gly Pro Asn Leu Tyr Asn Ile Arg Asn Leu His Ile Pro Glu
        595                 600                 605
Val Cys Leu Lys Trp Glu Leu Met Asp Glu Asp Tyr Lys Gly Arg Leu
    610                 615                 620
Cys Asn Pro Leu Asn Pro Phe Val Ser His Lys Glu Ile Glu Ser Val
625                 630                 635                 640
Asn Ser Ala Val Val Met Pro Ala His Gly Pro Ala Lys Ser Met Glu
                645                 650                 655
Tyr Asp Ala Val Ala Thr Thr His Ser Trp Ile Pro Lys Arg Asn Arg
            660                 665                 670
Ser Ile Leu Asn Thr Ser Gln Arg Gly Ile Leu Glu Asp Glu His Met
        675                 680                 685
Tyr Gln Lys Cys Cys Asn Leu Phe Glu Lys Phe Phe Pro Ser Ser Ser
    690                 695                 700
Tyr Arg Arg Pro Val Gly Ile Ser Ser Met Val Glu Ala Met Val Ser
705                 710                 715                 720
Arg Ala Arg Ile Asp Ala Arg Ile Asp Phe Glu Ser Gly Arg Ile Lys
                725                 730                 735
Lys Asp Glu Phe Ala Glu Ile Met Lys Ile Cys Ser Thr Ile Glu Glu
            740                 745                 750
Leu Lys Arg Gln Lys
        755

<210> SEQ ID NO 13
<211> LENGTH: 2233
<212> TYPE: DNA
<213> ORGANISM: Influenza A virus (H3N8)

<400> SEQUENCE: 13
agcgaaagca ggtactgatc caaaatggaa gactttgtgc gacagtgctt caatccaatg        60
atcgtcgagc ttgcggaaaa ggcaatgaaa gaatatggag agaacccgaa atcgaaaaca       120
aacaaatttg cagcaatatg cactcacttg gaagtctgct tcatgtactc ggatttccac       180
tttataaatg aactgggtga gtcagtggtc atagagtctg tgacccaaa tgctcttttg       240
```

| | |
|---|---|
| aaacacagat tgaaatcat tgaggggaga gatcgaacaa tggcatggac agtagtaaac | 300 |
| agcatctgca acaccacaag agctgaaaaa cctaaatttc ttccagattt atacgactat | 360 |
| aaggagaaca gatttgttga aattggtgtg acaaggagag aagttcacat atactacctg | 420 |
| gagaaggcca acaaaataaa gtctgagaaa acacatatcc acatcttctc atttacagga | 480 |
| gaggaaatgg ctacaaaagc ggactatact cttgatgaag agagtagagc caggatcaag | 540 |
| accagactat tcactataag acaagaaatg gccagtagag gcctctggga ttcctttcgt | 600 |
| cagtccgaga gaggcgaaga gacaattgaa gaaagatttg aaatcacagg gacgatgcgc | 660 |
| aagcttgcca attacagtct cccaccgaac ttctccagcc ttgaaaattt tagagtttat | 720 |
| gtagatggat tcgaaccgaa cggctgcatt gagagtaagc tttctcaaat gtccaaagaa | 780 |
| gtaaatgcca aaatcgaacc atttccaaag acaacacccc gaccactcaa aatgcctggt | 840 |
| ggtccaccct gccatcagcg atccaaattc ttgctaatgg atgctctgaa attgagcatt | 900 |
| gaagacccaa gtcacgaggg agaagggata ccactatatg atgcaatcaa atgcatgaaa | 960 |
| actttctttg gatggaaaga acccagtatt gttaaaccac ataaaaaggg tataaacccg | 1020 |
| aactatctcc aaacttggaa gcaagtatta gaagaaatac aagacattga gaacgaagaa | 1080 |
| aagaccccca aaaccaagaa tatgaaaaaa acaagccaat aaaatgggc actaggtgaa | 1140 |
| aatatggcac cagagaaagt ggattttgag gattgtaaag acatcaatga tttaaaacaa | 1200 |
| tatgacagtg atgagccaga agcaaggtct cttgcaagtt ggattcaaag tgagttcaac | 1260 |
| aaggcttgtg agctgacaga ttcaagctgg atagagctcg atgaaattgg ggaggatgtc | 1320 |
| gccccaatag aatacattgc gagcatgagg agagactatt ttactgctga gatttcccat | 1380 |
| tgtagagcaa cagaatatat aatgaaagga gtatacatca acactgctct actcaatgca | 1440 |
| tcctgtgctg cgatggatga atttcaattg attccgatga taagtaaatg caggaccaaa | 1500 |
| gaagggagaa ggaaaacaaa tttatatgga ttcataataa agggaaggtc ccatttaaga | 1560 |
| aatgatactg acgtggtgaa ctttgtaagt atggaatttt ctctcactga tccaagattt | 1620 |
| gagccacaca caatgggaaa atactgcgtt ctagaaattg agacatgct tctaagaact | 1680 |
| gctgtaggtc aagtgtcaag acccatgttt ttatatgtaa ggacaaatgg aacctctaaa | 1740 |
| attaaaatga atgggggaat ggaaatgagg cgctgcctcc ttcagtctct acaacagatt | 1800 |
| gaaagcatga tcgaagctga gtcctcagtc aaagaaaagg acatgaccaa agaattttt | 1860 |
| gagaacaaat cagagacatg gcctatagga gagtccccca aggagtggga agaaggctca | 1920 |
| atcgggaagg tttgcaggac cttattagca aaatctgtgt taacagttt atatgcatct | 1980 |
| ccacaactgg aaggattttc agctgaatct aggaaattac ttctcattgt tcaggctctt | 2040 |
| agagatgacc tggaacctgg aacctttgat attgggggt tatatgaatc aattgaggag | 2100 |
| tgcctgatta atgatccctg ggttttgctt aatgcatctt ggttcaactc cttcctcaca | 2160 |
| catgcactga gtagttgtg gcaatgctac tatttgctat ccatactgtc caaaaaagta | 2220 |
| ccttgtttct act | 2233 |

<210> SEQ ID NO 14
<211> LENGTH: 716
<212> TYPE: PRT
<213> ORGANISM: Influenza A virus (H3N8)

<400> SEQUENCE: 14

```
Met Glu Asp Phe Val Arg Gln Cys Phe Asn Pro Met Ile Val Glu Leu
1               5                   10                  15
```

```
Ala Glu Lys Ala Met Lys Glu Tyr Gly Asn Pro Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Leu Gly Glu Ser Val Val Ile Glu
    50                  55                  60

Ser Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Arg Ala Glu Lys Pro Lys Phe Leu Pro Asp Leu Tyr Asp Tyr
            100                 105                 110

Lys Glu Asn Arg Phe Val Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Lys Leu Ala Asn Tyr Ser Leu Pro Pro Asn Phe Ser
    210                 215                 220

Ser Leu Glu Asn Phe Arg Val Tyr Val Asp Gly Phe Glu Pro Asn Gly
225                 230                 235                 240

Cys Ile Glu Ser Lys Leu Ser Gln Met Ser Lys Glu Val Asn Ala Lys
                245                 250                 255

Ile Glu Pro Phe Ser Lys Thr Thr Pro Arg Pro Leu Lys Met Pro Gly
            260                 265                 270

Gly Pro Pro Cys His Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320

Ser Ile Val Lys Pro His Lys Lys Gly Ile Asn Pro Asn Tyr Leu Gln
                325                 330                 335

Thr Trp Lys Gln Val Leu Glu Glu Ile Gln Asp Ile Glu Asn Glu Glu
            340                 345                 350

Lys Thr Pro Lys Thr Lys Asn Met Lys Lys Thr Ser Gln Leu Lys Trp
        355                 360                 365

Ala Leu Gly Glu Asn Met Ala Pro Glu Lys Val Asp Phe Glu Asp Cys
    370                 375                 380

Lys Asp Ile Asn Asp Leu Lys Gln Tyr Asp Ser Asp Glu Pro Glu Ala
385                 390                 395                 400

Arg Ser Leu Ala Ser Trp Ile Gln Ser Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu Tyr Ile Ala Ser Met Arg Arg Asp Tyr Phe Thr Ala
```

-continued

```
        435                 440                 445

Glu Ile Ser His Cys Arg Ala Thr Glu Tyr Ile Met Lys Gly Val Tyr
    450                 455                 460
Ile Asn Thr Ala Leu Leu Asn Ala Ser Cys Ala Ala Met Asp Glu Phe
465                 470                 475                 480
Gln Leu Ile Pro Met Ile Ser Lys Cys Arg Thr Lys Glu Gly Arg Arg
                485                 490                 495
Lys Thr Asn Leu Tyr Gly Phe Ile Ile Lys Gly Arg Ser His Leu Arg
            500                 505                 510
Asn Asp Thr Asp Val Val Asn Phe Val Ser Met Glu Phe Ser Leu Thr
        515                 520                 525
Asp Pro Arg Phe Glu Pro His Lys Trp Glu Lys Tyr Cys Val Leu Glu
    530                 535                 540
Ile Gly Asp Met Leu Leu Arg Thr Ala Val Gly Gln Val Ser Arg Pro
545                 550                 555                 560
Met Phe Leu Tyr Val Arg Thr Asn Gly Thr Ser Lys Ile Lys Met Lys
                565                 570                 575
Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605
Lys Glu Phe Phe Glu Asn Lys Ser Glu Thr Trp Pro Ile Gly Glu Ser
    610                 615                 620
Pro Lys Gly Val Glu Glu Gly Ser Ile Gly Lys Val Cys Arg Thr Leu
625                 630                 635                 640
Leu Ala Lys Ser Val Phe Asn Ser Leu Tyr Ala Ser Pro Gln Leu Glu
                645                 650                 655
Gly Phe Ser Ala Glu Ser Arg Lys Leu Leu Leu Ile Val Gln Ala Leu
            660                 665                 670
Arg Asp Asp Leu Glu Pro Gly Thr Phe Asp Ile Gly Gly Leu Tyr Glu
        675                 680                 685
Ser Ile Glu Glu Cys Leu Ile Asn Asp Pro Trp Val Leu Leu Asn Ala
    690                 695                 700
Ser Trp Phe Asn Ser Phe Leu Thr His Ala Leu Lys
705                 710                 715

<210> SEQ ID NO 15
<211> LENGTH: 1762
<212> TYPE: DNA
<213> ORGANISM: Influenza A virus (H3N8)

<400> SEQUENCE: 15
agcaaaagca ggggatattt ctttcaatca tgaaaacaac cattatttta atactactga      60
cccattgggc ctacagtcaa aacccaatca gtggcaataa cacagccaca ctgtgtctgg     120
gacaccatgc agtagcaaat ggaacattgg taaaaacaat gagtgatgat caaattgagg     180
tgacaaatgc tacagaatta gttcagagca tttcaatggg gaaaatatgc aacaaatcat     240
atagagttct agatggaaga aattgcacat taatagatgc aatgctagga gacccccagt     300
gtgacgcctt tcagtatgag agttgggacc tctttataga aagaagcaac gctttcagca     360
attgctaccc atatgacatc cctgactatg catcgctccg atccattgta gcatcctcag     420
gaacagtgga attcacagca gagggattca catggacagg tgtcactcaa aacggaagaa     480
gtggagcctg caaaagggga tcagccgata gtttctttag ccgactgaat tggctaacaa     540
```

```
aatctggaag ctcttacccc acattgaatg tgacaatgcc taacaataaa aatttcgaca      600
agctatacat ctgggggatt catcacccga gctcgaatca agagcagaca aaattgtaca      660
tccaagaatc aggacgagta acagtctcaa caaaagaag tcaacaaaca ataatccctc       720
acatcggatc tagaccgttg atcagaggtc aatcaggcag ataagcata tactggacca      780 ttgtaaaacc tggagatatc ctaatgataa acagtaatgg caacttagtt gcaccgcggg     840
gatatttcaa attgaaccca ggaaaaagct ctgtaatgag atccgatgta cccatagaca    900
tttgtgtgtc tgaatgtatt acaccaaatg gaagcatctc caacgacaag ccattccaaa    960
atgtgaacaa agttacatat ggaaaatgcc ccaagtatat caggcaaaac acttaaagt    1020 tggccactgg gatgaggaat gtgccagaaa agcaaaccag aggaatcttt ggggcgatag    1080
cgggattcat cgaaaacggc tgggaaggaa tggttgatgg gtggtatggg ttccgatatc    1140
aaaactctga aggaacaggg caagctgcag atctaaagag cactcaagca gccatcgacc    1200
agattaatgg aaagttaaac agggtgattg aaagaaccaa tgagaaattc catcaaatag    1260
agaaggaatt ctcagaagta aaggaagaa ttcaggactt ggagaaatat gtagaagaca    1320
ccaaaataga cctatggtcc tacaatgcag aactgctggt ggctctagaa atcaacata    1380 caattgactt aacagatgca gaaatgaata aattatttga aagactaga cgccagttaa    1440 gagaaaatgc agaagacatg ggagatggat gtttcaagat ttaccacaag tgtgataatg    1500
catgcattga gtcaataaga actggaacat atgaccatta catatacaaa gatgaagcat    1560
taaacaaccg atttcagatc aaaggtgtag aattgaaatc aggctacaaa gattggatac    1620
tgtggatttc attcgccata tcatgcttct taatttgcgt tgttctattg ggtttcatta    1680
tgtgggcttg ccaaaaaggc aacatcagat gcaacatttg catttgagta aactgatagt    1740
taaaaacacc cttgtttcta ct                                              1762
```

<210> SEQ ID NO 16
<211> LENGTH: 565
<212> TYPE: PRT
<213> ORGANISM: Influenza A virus (H3N8)

<400> SEQUENCE: 16

Met Lys Thr Thr Ile Ile Leu Ile Leu Leu Thr His Trp Ala Tyr Ser
1               5                   10                  15

Gln Asn Pro Ile Ser Gly Asn Asn Thr Ala Thr Leu Cys Leu Gly His
            20                  25                  30

His Ala Val Ala Asn Gly Thr Leu Val Lys Thr Met Ser Asp Asp Gln
        35                  40                  45

Ile Glu Val Thr Asn Ala Thr Glu Leu Val Gln Ser Ile Ser Met Gly
    50                  55                  60

Lys Ile Cys Asn Lys Ser Tyr Arg Val Leu Asp Gly Arg Asn Cys Thr
65                  70                  75                  80

Leu Ile Asp Ala Met Leu Gly Asp Pro Gln Cys Asp Ala Phe Gln Tyr
                85                  90                  95

Glu Ser Trp Asp Leu Phe Ile Glu Arg Ser Asn Ala Phe Ser Asn Cys
            100                 105                 110

Tyr Pro Tyr Asp Ile Pro Asp Tyr Ala Ser Leu Arg Ser Ile Val Ala
        115                 120                 125

Ser Ser Gly Thr Val Glu Phe Thr Ala Glu Gly Phe Thr Trp Thr Gly
    130                 135                 140

Val Thr Gln Asn Gly Arg Ser Gly Ala Cys Lys Arg Gly Ser Ala Asp
145                 150                 155                 160

```
Ser Phe Phe Ser Arg Leu Asn Trp Leu Thr Lys Ser Gly Ser Ser Tyr
                165                 170                 175

Pro Thr Leu Asn Val Thr Met Pro Asn Asn Lys Asn Phe Asp Lys Leu
            180                 185                 190

Tyr Ile Trp Gly Ile His His Pro Ser Ser Asn Gln Glu Gln Thr Lys
        195                 200                 205

Leu Tyr Ile Gln Glu Ser Gly Arg Val Thr Val Ser Thr Lys Arg Ser
    210                 215                 220

Gln Gln Thr Ile Ile Pro His Ile Gly Ser Arg Pro Leu Ile Arg Gly
225                 230                 235                 240

Gln Ser Gly Arg Ile Ser Ile Tyr Trp Thr Ile Val Lys Pro Gly Asp
                245                 250                 255

Ile Leu Met Ile Asn Ser Asn Gly Asn Leu Val Ala Pro Arg Gly Tyr
            260                 265                 270

Phe Lys Leu Asn Pro Gly Lys Ser Ser Val Met Arg Ser Asp Val Pro
        275                 280                 285

Ile Asp Ile Cys Val Ser Glu Cys Ile Thr Pro Asn Gly Ser Ile Ser
    290                 295                 300

Asn Asp Lys Pro Phe Gln Asn Val Asn Lys Val Thr Tyr Gly Lys Cys
305                 310                 315                 320

Pro Lys Tyr Ile Arg Gln Asn Thr Leu Lys Leu Ala Thr Gly Met Arg
                325                 330                 335

Asn Val Pro Glu Lys Gln Thr Arg Gly Ile Phe Gly Ala Ile Ala Gly
            340                 345                 350

Phe Ile Glu Asn Gly Trp Glu Gly Met Val Asp Gly Trp Tyr Gly Phe
        355                 360                 365

Arg Tyr Gln Asn Ser Glu Gly Thr Gly Gln Ala Ala Asp Leu Lys Ser
    370                 375                 380

Thr Gln Ala Ala Ile Asp Gln Ile Asn Gly Lys Leu Asn Arg Val Ile
385                 390                 395                 400

Glu Arg Thr Asn Glu Lys Phe His Gln Ile Glu Lys Glu Phe Ser Glu
                405                 410                 415

Val Glu Gly Arg Ile Gln Asp Leu Glu Lys Tyr Val Glu Asp Thr Lys
            420                 425                 430

Ile Asp Leu Trp Ser Tyr Asn Ala Glu Leu Leu Val Ala Leu Glu Asn
        435                 440                 445

Gln His Thr Ile Asp Leu Thr Asp Ala Glu Met Asn Lys Leu Phe Glu
    450                 455                 460

Lys Thr Arg Arg Gln Leu Arg Glu Asn Ala Glu Asp Met Gly Asp Gly
465                 470                 475                 480

Cys Phe Lys Ile Tyr His Lys Cys Asp Asn Ala Cys Ile Glu Ser Ile
                485                 490                 495

Arg Thr Gly Thr Tyr Asp His Tyr Ile Tyr Lys Asp Glu Ala Leu Asn
            500                 505                 510

Asn Arg Phe Gln Ile Lys Gly Val Glu Leu Lys Ser Gly Tyr Lys Asp
        515                 520                 525

Trp Ile Leu Trp Ile Ser Phe Ala Ile Ser Cys Phe Leu Ile Cys Val
    530                 535                 540

Val Leu Leu Gly Phe Ile Met Trp Ala Cys Gln Lys Gly Asn Ile Arg
545                 550                 555                 560

Cys Asn Ile Cys Ile
                565
```

<210> SEQ ID NO 17
<211> LENGTH: 1565
<212> TYPE: DNA
<213> ORGANISM: Influenza A virus (H3N8)

<400> SEQUENCE: 17

```
agcaaaagca gggtagataa tcactcactg agtgacatca aagtcatggc gtctcaaggc      60
accaaacgat cctatgaaca gatggaaact gatggggaac gccagaatgc aactgaaatc     120
agaacatctg tcggaaggat ggtgggagga atcggacggt tttatgtcca gatgtgtact     180
gagcttaaac taaacgacta tgaagggcgg ctgattcaga acagcataac aatagaaagg     240
atggtacttt cggcattcga cgaaagaaga aacaagtatc tcgaggagca tcccagtgct     300
gggaagacc ctaagaaaac gggggcccg atatacagaa gaaagatgg gaaatggatg        360
agggaactca tcctccatga taagaagaa atcatgagaa tctggcgtca ggccaacaat      420
ggtgaagacg ctactgctgg tcttactcac atgatgatct ggcactccaa tctcaacgac     480
accacatacc aaagaacaag ggctcttgtt cggactggga tggatcccag aatgtgctct     540
ttgatgcaag gctcaaccct cccacggaga tctggagccg ctggtgctgc agtaaaaggt     600
gttgaacaa tggtaatgga actcatcaga atgatcaagc gcggaataaa tgatcggaat      660
ttctggagag gtgaaaatgg tcgaagaacc agaattgctt atgaaagaat gtgcaatatc     720
ctcaaggga aatttcagac agcagcacaa cgggctatga tggaccaggt gagggaaggc     780
cgcaaccctg aaacgctga aattgaggat ctcatttct tggcacgatc agcacttatt       840
ttgagaggat cagtagccca taatcatgc ctacctgcct gtgtttatgg ccttgcagta      900
accagtgggt atgactttga aaggaagga tactctctgg ttggaattga tcctttcaaa      960
ctactccaga cagtcaaat tttcagtcta atcagaccaa agaaaaccc agcacacaaa      1020
agccaattgg tgtggatggc atgccattct gcagcatttg aggatctgag agtttttaaat  1080
ttcattagag gaaccaaagt aatcccaaga ggacagttaa caaccagagg agttcaaatt  1140
gcttcaaatg aaaacatgga gacaataaat tctagcacac ttgaactgag aagcaaatat 1200
tgggcaataa gaaccagaag cggaggaaac accagtcaac agagagcatc tgcaggacag 1260
ataagtgtgc aacctacttt ctcagtacag agaaatcttc cctttgagag agcaaccatt 1320
atggctgcat tcactggtaa cactgaaggg aggacttccg acatgagaac ggaaatcata 1380
aggatgatgg aaaatgccaa atcagaagat gtgtctttcc aggggcgggg agtcttcgag 1440
ctctcggacg aaaaggcaac gaacccgatc gtgccttcct ttgacatgag caatgaaggg 1500
tcttatttct tcggagacaa tgctgaggag tttgacaatt aaagaaaaat acccttgttt 1560
ctact                                                                1565
```

<210> SEQ ID NO 18
<211> LENGTH: 498
<212> TYPE: PRT
<213> ORGANISM: Influenza A virus (H3N8)

<400> SEQUENCE: 18

```
Met Ala Ser Gln Gly Thr Lys Arg Ser Tyr Glu Gln Met Glu Thr Asp
1               5                   10                  15

Gly Glu Arg Gln Asn Ala Thr Glu Ile Arg Thr Ser Val Gly Arg Met
            20                  25                  30

Val Gly Gly Ile Gly Arg Phe Tyr Val Gln Met Cys Thr Glu Leu Lys
        35                  40                  45
```

```
Leu Asn Asp Tyr Glu Gly Arg Leu Ile Gln Asn Ser Ile Thr Ile Glu
 50                  55                  60

Arg Met Val Leu Ser Ala Phe Asp Glu Arg Arg Asn Lys Tyr Leu Glu
 65                  70                  75                  80

Glu His Pro Ser Ala Gly Lys Asp Pro Lys Lys Thr Gly Gly Pro Ile
                     85                  90                  95

Tyr Arg Arg Lys Asp Gly Lys Trp Met Arg Glu Leu Ile Leu His Asp
                 100                 105                 110

Lys Glu Glu Ile Met Arg Ile Trp Arg Gln Ala Asn Asn Gly Glu Asp
             115                 120                 125

Ala Thr Ala Gly Leu Thr His Met Met Ile Trp His Ser Asn Leu Asn
130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
                180                 185                 190

Leu Ile Arg Met Ile Lys Arg Gly Ile Asn Asp Arg Asn Phe Trp Arg
            195                 200                 205

Gly Glu Asn Gly Arg Arg Thr Arg Ile Ala Tyr Glu Arg Met Cys Asn
210                 215                 220

Ile Leu Lys Gly Lys Phe Gln Thr Ala Ala Gln Arg Ala Met Met Asp
225                 230                 235                 240

Gln Val Arg Glu Gly Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Thr Ser Gly
        275                 280                 285

Tyr Asp Phe Glu Lys Glu Gly Tyr Ser Leu Val Gly Ile Asp Pro Phe
290                 295                 300

Lys Leu Leu Gln Asn Ser Gln Ile Phe Ser Leu Ile Arg Pro Lys Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Asn Phe Ile Arg Gly Thr Lys Val
            340                 345                 350

Ile Pro Arg Gly Gln Leu Thr Thr Arg Gly Val Gln Ile Ala Ser Asn
        355                 360                 365

Glu Asn Met Glu Thr Ile Asn Ser Ser Thr Leu Glu Leu Arg Ser Lys
370                 375                 380

Tyr Trp Ala Ile Arg Thr Arg Ser Gly Gly Asn Thr Ser Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
            420                 425                 430

Thr Glu Gly Arg Thr Ser Asp Met Arg Thr Glu Ile Ile Arg Met Met
        435                 440                 445

Glu Asn Ala Lys Ser Glu Asp Val Ser Phe Gln Gly Arg Gly Val Phe
450                 455                 460

Glu Leu Ser Asp Glu Lys Ala Thr Asn Pro Ile Val Pro Ser Phe Asp
```

Met Ser Asn Glu Gly Ser Tyr Phe Phe Gly Asp Asn Ala Glu Glu Phe
465             470                 475                 480
                    485                 490                 495
Asp Asn

<210> SEQ ID NO 19
<211> LENGTH: 1461
<212> TYPE: DNA
<213> ORGANISM: Influenza A virus (H3N8)

<400> SEQUENCE: 19

```
agcaaaagca ggagtttaaa atgaatccaa atcaaaagat aatagcaatt ggatctgcat    60
cattggggat attaatcatt aatgtcattc tccatgtagt cagcattata gtaacagtac   120
tggtcctcaa taacaataga acagatcaa actgcaaagg gacgatcata agagagtaca   180
atgaaacagt aagagtagaa aaacttactc aatggtataa tatcagtaca attaagtaca   240
tagagagacc ttcaaatgaa tattacatga caacactga ccactttgt gaggcccaag    300
gctttgcacc attttccaaa gataatggaa tacgaattgg gtcgagaggc catgtttttg   360
tgataagaga accttttgta tcatgttcac cctcagaatg tagaacctttt tcctcacac    420
agggctcatt actcaatgac aaacattcta acggcacaat aaaggatcga agtccgtata   480
ggactctgat gagtgtcaaa atagggcaat cacctaatgt atatcaagct aaatttgaat   540
cggtggcatg gtcagcaaca gcatgccatg atggaaaaaa atggatgaca gttggagtca   600
cagggcccga caatcaagca attgcagtag tgaactatgg aggtgttccg gttgatatta   660
ttaattcatg ggcaggggat attttaagaa cccaagaatc atcatgcacc tgcattaaag   720
gagactgtta tggggtaatg actgatggac cggcaaatag gcaagctaat taaggatat   780
tcaaagcaaa agatggaaga gtaattggac gaactgatat aagtttcaat gggggacaca   840
tagaggagtg ttcttgttac cccaatgaag ggaaggtgga atgcatatgc agagacaatt   900
ggactggaac aaatagacca attctggtaa tatcttctga tctatcgtac acagttggat   960
atttgtgtgc tggcattccc actgacaccc tagggggaga ggatagtcaa ttcacaggct  1020
catgtacaag tccctttgga aataaaggat acggagtcaa aggtttcggg tttcgacaag  1080
gaactgacgt atgggccgga aggacaatta gtaggacttc aagatcagga ttcgaaataa  1140
taaaaatcag gaatggttgg acacagaata gtaaggacca atcaggagg caagtgatta  1200
tcgatgaccc aaattggtca ggatatagcg gttctttcac attgccggtt gaattaacaa  1260
aaaaaggatg tttggtcccc tgtttctggg ttgaaatgat tagaggtaaa cctgaagaaa  1320
caacaatatg gaccctagc agctccattg tgatgtgtgg agtagatcat aaaattgcca  1380
gttggtcatg gcacgatgga gcaattcttc cctttgacat cgataagatg taatttatga  1440
aaaaaactcc ttgtttctac t                                             1461
```

<210> SEQ ID NO 20
<211> LENGTH: 470
<212> TYPE: PRT
<213> ORGANISM: Influenza A virus (H3N8)

<400> SEQUENCE: 20

Met Asn Pro Asn Gln Lys Ile Ile Ala Ile Gly Ser Ala Ser Leu Gly
1               5                   10                  15

Ile Leu Ile Ile Asn Val Ile Leu His Val Val Ser Ile Ile Val Thr
            20                  25                  30

-continued

Val Leu Val Leu Asn Asn Asn Arg Thr Asp Leu Asn Cys Lys Gly Thr
            35                  40                  45

Ile Ile Arg Glu Tyr Asn Glu Thr Val Arg Val Glu Lys Leu Thr Gln
50                  55                  60

Trp Tyr Asn Ile Ser Thr Ile Lys Tyr Ile Glu Arg Pro Ser Asn Glu
65                  70                  75                  80

Tyr Tyr Met Asn Asn Thr Glu Pro Leu Cys Glu Ala Gln Gly Phe Ala
            85                  90                  95

Pro Phe Ser Lys Asp Asn Gly Ile Arg Ile Gly Ser Arg Gly His Val
                100                 105                 110

Phe Val Ile Arg Glu Pro Phe Val Ser Cys Ser Pro Ser Glu Cys Arg
            115                 120                 125

Thr Phe Phe Leu Thr Gln Gly Ser Leu Leu Asn Asp Lys His Ser Asn
130                 135                 140

Gly Thr Ile Lys Asp Arg Ser Pro Tyr Arg Thr Leu Met Ser Val Lys
145                 150                 155                 160

Ile Gly Gln Ser Pro Asn Val Tyr Gln Ala Lys Phe Glu Ser Val Ala
                165                 170                 175

Trp Ser Ala Thr Ala Cys His Asp Gly Lys Lys Trp Met Thr Val Gly
            180                 185                 190

Val Thr Gly Pro Asp Asn Gln Ala Ile Ala Val Val Asn Tyr Gly Gly
            195                 200                 205

Val Pro Val Asp Ile Ile Asn Ser Trp Ala Gly Asp Ile Leu Arg Thr
210                 215                 220

Gln Glu Ser Ser Cys Thr Cys Ile Lys Gly Asp Cys Tyr Trp Val Met
225                 230                 235                 240

Thr Asp Gly Pro Ala Asn Arg Gln Ala Asn Tyr Arg Ile Phe Lys Ala
                245                 250                 255

Lys Asp Gly Arg Val Ile Gly Arg Thr Asp Ile Ser Phe Asn Gly Gly
            260                 265                 270

His Ile Glu Glu Cys Ser Cys Tyr Pro Asn Glu Gly Lys Val Glu Cys
            275                 280                 285

Ile Cys Arg Asp Asn Trp Thr Gly Thr Asn Arg Pro Ile Leu Val Ile
290                 295                 300

Ser Ser Asp Leu Ser Tyr Thr Val Gly Tyr Leu Cys Ala Gly Ile Pro
305                 310                 315                 320

Thr Asp Thr Pro Arg Gly Glu Asp Ser Gln Phe Thr Gly Ser Cys Thr
                325                 330                 335

Ser Pro Leu Gly Asn Lys Gly Tyr Gly Val Lys Gly Phe Gly Phe Arg
            340                 345                 350

Gln Gly Thr Asp Val Trp Ala Gly Arg Thr Ile Ser Arg Thr Ser Arg
            355                 360                 365

Ser Gly Phe Glu Ile Ile Lys Ile Arg Asn Gly Trp Thr Gln Asn Ser
370                 375                 380

Lys Asp Gln Ile Arg Arg Gln Val Ile Ile Asp Asp Pro Asn Trp Ser
385                 390                 395                 400

Gly Tyr Ser Gly Ser Phe Thr Leu Pro Val Glu Leu Thr Lys Lys Gly
                405                 410                 415

Cys Leu Val Pro Cys Phe Trp Val Glu Met Ile Arg Gly Lys Pro Glu
            420                 425                 430

Glu Thr Thr Ile Trp Thr Ser Ser Ser Ile Val Met Cys Gly Val
            435                 440                 445

Asp His Lys Ile Ala Ser Trp Ser Trp His Asp Gly Ala Ile Leu Pro

```
    450                 455                 460

Phe Asp Ile Asp Lys Met
465                 470

<210> SEQ ID NO 21
<211> LENGTH: 1027
<212> TYPE: DNA
<213> ORGANISM: Influenza A virus (H3N8)

<400> SEQUENCE: 21
agcaaaagca ggtagatatt taaagatgag tcttctaacc gaagtcgaaa cgtacgttct      60
ctctatcata ccatcaggcc ccctcaaagc cgagatcgcg cagagacttg aagatgtctt     120
tgcgggaaag aacaccgatc ttgaggcact tatggaatgg ctaaagacaa gaccaatcct     180
gtcacctctg actaaaggga ttttaggatt tgtattcacg ctcaccgtgc ccagtgagcg     240
aggactgcag cgtagacgct ttgtccaaaa tgcccttagt ggaaacggag atccaaacaa     300
catggacaga gcagtaaaac tatacaggaa gcttaaaaga gaaataacat tccatggggc     360
aaaagaagtg gcactcagct attccactgg tgcactagcc agttgcatgg gactcatata     420
caacagaatg ggaactatta caaccgaagt ggcatttggc ctggtatgcg ccacatgtga     480
acagattgct gattcccagc atcggtctca caggcagatg gtgacaacaa ccaacccatt     540
aatcagacat gaaaacagaa tggtattagc cagcaccacg gctaaagcca tggaacagat     600
ggcaggatcg agtgagcaag cagcagaggc catggaggtt gctagtaggg ctaggcagat     660
ggtacaggca atgagaacca ttgggaccca ccctagctcc agtgccggtt tgaaagatga     720
tctccttgaa aatttacagg cctaccagaa acggatggga gtgcaaatgc agcgattcaa     780
gtgatcctct cgttactgca gcaagtatca ttgggatctt gcacttgata ttgtggattc     840
ttgatcgtct tttcttcaaa ttcatttatc gtcgccttaa atacgggtta aaaagagggc     900
cttctacgga aggagtacct gagtctatga gggaagaata tcggcaggaa cagcagaatg     960
ctgtggatgt tgacgatggt cattttgtca acatagagct ggagtaaaaa actaccttgt    1020
ttctact                                                               1027

<210> SEQ ID NO 22
<211> LENGTH: 252
<212> TYPE: PRT
<213> ORGANISM: Influenza A virus (H3N8)

<400> SEQUENCE: 22

Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Ser Gly Asn Gly Asp Pro Asn Asn Met Asp Arg Ala
                85                  90                  95

Val Lys Leu Tyr Arg Lys Leu Lys Arg Glu Ile Thr Phe His Gly Ala
            100                 105                 110

Lys Glu Val Ala Leu Ser Tyr Ser Thr Gly Ala Leu Ala Ser Cys Met
```

```
        115                 120                 125

Gly Leu Ile Tyr Asn Arg Met Gly Thr Ile Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Arg
        195                 200                 205

Ala Arg Gln Met Val Gln Ala Met Arg Thr Ile Gly Thr His Pro Ser
    210                 215                 220

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 23
<211> LENGTH: 91
<212> TYPE: PRT
<213> ORGANISM: Influenza A virus (H3N8)

<400> SEQUENCE: 23

Met Ser Leu Leu Thr Glu Val Glu Thr Glu Cys Lys Cys Ser Asp Ser
1               5                   10                  15

Ser Asp Pro Leu Val Thr Ala Ala Ser Ile Ile Gly Ile Leu His Leu
            20                  25                  30

Ile Leu Trp Ile Leu Asp Arg Leu Phe Phe Lys Phe Ile Tyr Arg Arg
        35                  40                  45

Leu Lys Tyr Gly Leu Lys Arg Gly Pro Ser Thr Glu Gly Val Pro Glu
    50                  55                  60

Ser Met Arg Glu Glu Tyr Arg Gln Glu Gln Gln Asn Ala Val Asp Val
65                  70                  75                  80

Asp Asp Gly His Phe Val Asn Ile Glu Leu Glu
                85                  90

<210> SEQ ID NO 24
<211> LENGTH: 890
<212> TYPE: DNA
<213> ORGANISM: Influenza A virus (H3N8)

<400> SEQUENCE: 24
agcaaaagca gggtgacaaa aacataatgg attccaacac tgtgtcaagc tttcaggtag      60
actgttttct ttggcatgtc cgcaaacaat tcgcagacca agaactgggt gatgccccat     120
tccttgaccg gcttcgccga gaccagaagt ccctaagggg aagaggtagc actcttggtc     180
tggacatcga aacagccact catgcaggaa agcagatagt ggagcagatt ctggaaaagg     240
aatcagatga ggcacctaaa atgaccattg cctctgttcc tgcttcacgc tacttaactg     300
acatgactct tgatgagatg tcaagagact ggttcatgct catgcccaag caaaaagtaa     360
caggctccct atgtataaga atggaccagg caatcatgga taagaacatc atacttaaag     420
caaactttag tgtgattttc gaaaggctgg aaacactaat actacttaga gccttcaccg     480
aagaaggagc aatcgttggc gaaatttcac cattaccttc tcttccagga catactaatg     540
aggatgtcaa aaatgcaatt ggggtcctca tcggaggatt taaatggaat gataatacgg     600
```

```
ttaaaatctc tgaaactcta cagagattcg cttggagaag cagtcatgag aatgggagac    660
cttcactccc ttcaaagcag aaacgaaaaa tggagagaac aattaagcca gaaatttgaa    720
gaaataagat ggttgattga agaagtgcga catagactga aaaatacaga aaatagtttt    780
gaacaaataa catttatgca agccttacaa ctattgcttg aagtagaaca agagataaga    840
actttctcgt ttcagcttat ttaatgataa aaaacaccct tgtttctact               890

<210> SEQ ID NO 25
<211> LENGTH: 230
<212> TYPE: PRT
<213> ORGANISM: Influenza A virus (H3N8)

<400> SEQUENCE: 25

Met Asp Ser Asn Thr Val Ser Ser Phe Gln Val Asp Cys Phe Leu Trp
1               5                   10                  15

His Val Arg Lys Gln Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr His Ala Gly Lys Gln Ile
    50                  55                  60

Val Glu Gln Ile Leu Glu Lys Glu Ser Asp Glu Ala Pro Lys Met Thr
65                  70                  75                  80

Ile Ala Ser Val Pro Ala Ser Arg Tyr Leu Thr Asp Met Thr Leu Asp
                85                  90                  95

Glu Met Ser Arg Asp Trp Phe Met Leu Met Pro Lys Gln Lys Val Thr
            100                 105                 110

Gly Ser Leu Cys Ile Arg Met Asp Gln Ala Ile Met Asp Lys Asn Ile
        115                 120                 125

Ile Leu Lys Ala Asn Phe Ser Val Ile Phe Glu Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Asn Glu Asp Val Lys Asn
                165                 170                 175

Ala Ile Gly Val Leu Ile Gly Gly Phe Lys Trp Asn Asp Asn Thr Val
            180                 185                 190

Lys Ile Ser Glu Thr Leu Gln Arg Phe Ala Trp Arg Ser Ser His Glu
        195                 200                 205

Asn Gly Arg Pro Ser Leu Pro Ser Lys Gln Lys Arg Lys Met Glu Arg
    210                 215                 220

Thr Ile Lys Pro Glu Ile
225                 230

<210> SEQ ID NO 26
<211> LENGTH: 121
<212> TYPE: PRT
<213> ORGANISM: Influenza A virus (H3N8)

<400> SEQUENCE: 26

Met Asp Ser Asn Thr Val Ser Ser Phe Gln Asp Ile Leu Met Arg Met
1               5                   10                  15

Ser Lys Met Gln Leu Gly Ser Ser Ser Glu Asp Leu Asn Gly Met Ile
            20                  25                  30

Ile Arg Leu Lys Ser Leu Lys Leu Tyr Arg Asp Ser Leu Gly Glu Ala
```

```
                  35                  40                  45
Val Met Arg Met Gly Asp Leu His Ser Leu Gln Ser Arg Asn Glu Lys
         50                  55                  60

Trp Arg Glu Gln Leu Ser Gln Lys Phe Glu Glu Ile Arg Trp Leu Ile
 65                  70                  75                  80

Glu Glu Val Arg His Arg Leu Lys Asn Thr Glu Asn Ser Phe Glu Gln
                 85                  90                  95

Ile Thr Phe Met Gln Ala Leu Gln Leu Leu Glu Val Glu Gln Glu
             100                 105                 110

Ile Arg Thr Phe Ser Phe Gln Leu Ile
         115                 120

<210> SEQ ID NO 27
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 27
gataagtaga tcttgattaa ttaagaagga                                      30

<210> SEQ ID NO 28
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 28
atgtcatgat taattaagaa gga                                             23

<210> SEQ ID NO 29
<211> LENGTH: 26
<212> TYPE: DNA
<213> ORGANISM: Artificial Sequence
<220> FEATURE:
<223> OTHER INFORMATION: Chemically Synthesized

<400> SEQUENCE: 29
gaatcataag ctttaattaa gaagga                                          26

<210> SEQ ID NO 30
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 30
tttcagctcg aggacata                                                   18
```

NS1 TRUNCATED VIRUS FOR THE DEVELOPMENT OF CANINE INFLUENZA VACCINES

CROSS-REFERENCES TO RELATED APPLICATIONS

This application is a U.S. national phase application filed under 35 U.S.C. § 371 claiming benefit to International Patent Application No. PCT/US16/47711, filed Aug. 19, 2016, which is entitled to priority under 35 U.S.C. § 119(e) to U.S. Provisional Patent Application No. 62/207,576, filed Aug. 20, 2015, each of which application is hereby incorporated herein by reference in its entirety.

BACKGROUND OF THE INVENTION

Influenza A viruses (IAVs) have a broad host range and mainly exist in the wild aquatic fowl reservoir (de Jong et al., 2007, J Virol, 81:4315-4322, Taubenberger et al., 2010, Cell host & microbe, 7:440-451, Webster et al., 1992, Microbiological reviews, 56:152-179, Yoon et al., 2014, Current topics in microbiology and immunology, 385:359-375). IAV has gained the capacity to cross the species barrier to infect and cause disease in new hosts (Parrish et al., 2005, Annual review of microbiology, 59:553-586, Parrish et al., 2015, J Virol, 89:2990-2994). Two IAV strains emerged in dogs in the past 16 years, first the equine-origin H3N8 CIV in the USA around 1999 (Crawford et al., 2005, Science, 310:482-485), and then the avian-origin CIV H3N2 in China around 2005 (Song et al., 2008, Emerging infectious diseases, 14:741-746). Serological evidence demonstrated that CIV H3N8 has been circulating in dogs in the United States (US) since 1999 (Hayward et al., 2010, J Virol, 84:12636-12645), the virus was first isolated in 2004 from Florida racing greyhounds exhibiting signs of respiratory disease (Crawford et al., 2005, Science, 310:482-485). In turn, H3N2 CIV has been circulating in Asia after 2005, and was imported to North America in February 2015. Therefore, CIVs represent new threats to canine health in the US, and potentially worldwide (Crawford et al., 2005, Science, 310: 482-485, Holt et al., 2010, Journal of the American Veterinary Medical Association, 237:71-73, Pecoraro et al., 2013, Journal of veterinary diagnostic investigation, 25:402-406, Yoon et al., 2005, Emerging infectious diseases, 11:1974-1976). Vaccination remains the best prophylactic option against IAV infection (Nogales et al., 2014, J Virol, 88:10525-10540, Pica et al., 2013, Annual review of medicine, 64:189-202), but only inactivated influenza vaccines (IIV) against H3N8 and H3N2 are commercially available. IIVs require the production of large amounts of virus and do not induce significant cellular responses, which are important for generating long-term memory against subsequent influenza infections (Belshe et al., 2007, The New England journal of medicine, 356:685-696, Belshe et al., 2000, The Journal of infectious diseases, 181:1133-1137, Centers et al., 2010, MMWR, 59(16):485-486, Rimmelzwaan et al., 2007, Current opinion in biotechnology, 18:529-536). In contrast, live attenuated influenza vaccines (LAIVs) induce stronger innate and adaptive cellular and humoral immunity (Belshe et al., 2007, The New England journal of medicine, 356: 685-696, Cox et al., 2015, J Virol, 89(6):3421-3426). In addition, LAIVs have the advantage of intranasal administration, avoiding possible muscle soreness and potential iatrogenic practices associated with the intramuscular administration of IIV.

An important public health concern is the ability of IAV to cause occasional pandemics when novel viruses are introduced into humans (Smith et al., 2009, Nature, 459: 1122-1125). Dogs are susceptible to IAVs, and could become "mixing vessels" species for the generation of novel IAVs with pandemic potential to humans. Moreover, natural and experimental infections of dogs with human viruses have been reported (Dundon et al., 2009, Emerging infectious diseases, 16:2019-2021, Song et al., 2015, The Journal of general virology, 96:254-258), and reassortants between canine and human influenza viruses could result in the emergence of new viruses in humans.

In 2006, the American Veterinary Medical Association (AVMA) called for the urgent development of an effective vaccine against CIV. A vaccine made from inactivated virus have been developed that is administered subcutaneously as two doses to reduce the severity of the CIV disease and to reduce the incidence of CIV infection in naive dogs (Nobivac, Merck). However, to date, no LAIV for CIV infections has been developed. Thus there is a need in the art for improved vaccines for CIV. The present invention satisfies this unmet need.

SUMAMRY OF THE INVENTION

In one aspect, the present invention provides an immunological composition comprising a canine influenza virus (CIV), wherein the CIV comprises one or more mutations in segment 8 of the viral genome. In one embodiment, the segment 8 comprises a nucleic acid sequence selected from the group consisting of SEQ ID NO: 1, SEQ ID NO: 2, SEQ ID NO: 3, and SEQ ID NO: 4

In one embodiment, the CIV comprises one or more mutations in segment 8, which encodes a truncation mutant of NS1. In one embodiment, the truncation mutant of NS1 is selected from the group consisting of NS1-126, NS1-99, and NS1-73. in one embodiment, the truncation mutant of NS1 comprises an amino acid sequence selected from the group consisting of SEQ ID NO: 5, SEQ ID NO: 6, and SEQ ID NO: 7. In one embodiment, the CIV comprises one or more mutations in segment 8 such that NS1 is not expressed.

In one embodiment, the CIV is derived from H3N8 subtype of influenza A virus. In one embodiment the composition is used for the treatment or prevention of canine influenza in a subject.

In one aspect, the present invention provides a method for treating or preventing canine influenza in a subject. The method comprises administering to the subject an immunological composition comprising a canine influenza virus (CIV), wherein the CIV comprises one or more mutations in segment 8 of the viral genome.

In one embodiment, the segment 8 comprises a nucleic acid sequence selected from the group consisting of SEQ ID NO: 1, SEQ ID NO: 2, SEQ ID NO: 3, and SEQ ID NO: 4

In one embodiment, the CIV comprises one or more mutations in segment 8, which encodes a truncation mutant of NS1. In one embodiment, the truncation mutant of NS1 is selected from the group consisting of NS1-126, NS1-99, and NS1-73. in one embodiment, the truncation mutant of NS1 comprises an amino acid sequence selected from the group consisting of SEQ ID NO: 5, SEQ ID NO: 6, and SEQ ID NO: 7. In one embodiment, the CIV comprises one or more mutations in segment 8 such that NS1 is not expressed.

In one embodiment, the CIV is derived from H3N8 subtype of influenza A virus.

In one embodiment, the subject does not have canine influenza, and wherein the method induces immunity against one or more of: influenza A virus subtype H3N8 and influenza A virus subtype H3N2. In one embodiment, the subject is infected with at least one or more of: influenza A virus subtype H3N8 and influenza A virus subtype H3N2; and wherein the method induces a therapeutic immune response.

In one embodiment, the immunological composition is administered intranasally, intratracheally, orally, intradermally, intramuscularly, intraperitoneally, intravenously, or subcutaneously. In one embodiment, the subject is a dog.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A through FIG. 1C depicts the results of experiments demonstrating the generation of CIV with truncated NS1 proteins.

FIG. 2, comprising FIG. 2A through FIG. 2C depicts the results of experiments demonstrating the characterization of CIV WT and NS1-truncated viruses. (FIG. 2A and FIG. 2B) Multicycle growth kinetics of CIV WT and NS1-truncated viruses. MDCK cells were infected with the indicated viruses (MOI of 0.001) and incubated at 37° C. (FIG. 2A) or 33° C. (FIG. 2B). Supernatants were collected at 24, 48, 72, and 96 hours post-infection (h.p.i.) and viral titers were determined by immunofocus assay (FFU/ml). Data is expressed as the means of triplicate wells. Dotted black lines indicate limit of detection (20 FFU/ml). P<0.05:* WT versus $\Delta$NS1,  WT versus NS1-126 and NS1-99 and * WT versus NS1-73, using a Student's t test. (FIG. 2C) Plaque assays: Plaque sizes of WT and NS1-truncated H3N8 CIVs in MDCK cells at 33° C. were evaluated at 3 days post-infection.

FIG. 3, comprising (FIG. 3A) Schematic representation of the IFN-$\beta$ induction bioassays: MDCK cells constitutively expressing GFP-CAT and firefly luciferase (FFluc) reporter genes under the control of the IFN$\beta$ promoter (MDCK IFN$\beta$ GFP-CAT/FFluc) were infected with WT H3N8 CIV or NS1 mutants (MOI 3). At 12 h p.i. IFN$\beta$ promoter activation was determined by assessing GFP (fluorescence microscope) and FFluc (luciferase assay) expressions. Supernatants of the same MDCK infected cells were collected and, after UV virus inactivation, used to treat fresh MDCK cells for 24 hours prior to infection with rNDV-GFP. GFP expression from rNDV-GFP-infected cells was determined at 14 h p.i. using fluorescent microscopy. (FIG. 3B) Indirect immunofluorescence: WT and NS1-truncated H3N8 CIV infections of MDCK IFN$\beta$ GFP-CAT/FFluc cells were evaluated at 12 h p.i. using an anti-NP antibody. DAPI was used for nuclear staining. (FIG. 3C and FIG. 3D) Activation of the IFN$\beta$ promoter: At 12 hours post-infection of the MDCK IFN$\beta$ GFP-CAT/FFluc cells, activation of the IFN$\beta$ promoter was determined by assessing GFP expression (FIG. 3C) and FFluc activity. (FIG. 3D) Inhibition of NDV infection: Supernatants of previously infected MDCK cells were collected, UV-inactivated and used to treat fresh MDCK cells. After 24 hours of incubation, cells were infected with the IFN-sensitive rNDV-GFP (MOI 3). At 14 h p.i., rNDV-GFP-infected cells were quantified. (FIG. 3E). Scale bars, 200 $\mu$M (FIG. 3B and FIG. 3C). Data shown in FIG. 3D and FIG. 3E represents the means and SDs of triplicate wells. *, P<0.05 (WT versus NS1-126, WT versus NS1-99, WT versus NS1-73 or WT versus $\Delta$NS1) using Student's t test.

FIG. 5, comprising FIG. 5A (FIG. 5B) Protection efficacy: Two weeks post-vaccination, mice were challenged with 1×10$^5$ PFU of CIV WT H3N8. To evaluate virus replication, mice were euthanized at days 2 (N=3) and 4 (N=3) post-infection with WT H3N8 CIV, lungs were harvested and viral titers determined by immunofocus assay (FFU/ml). The dotted black line indicates the limit of detection (200 FFU/ml). ND, virus not detected. Data represent the means +/− SDs. *, P<0.05 (PBS vs. $\Delta$NS1 or PBS vs. Nobivac) using a Student's t test.

FIG. 6, comprising (FIG. 6A) Histological features of dog tracheas infected with 200 PFU of H3N8 CIVs (WT or mutants) or mock-infected with infection media. Lesions are shown in sections stained with haematoxylin and eosin (H&E). (FIG. 6B) Infected cells were detected by immunohistochemical staining of the NP viral protein. Positive cells are stained in brown. Black horizontal bars represent 20 μm.

FIG. 9 depicts the nucleotide sequence of modified segment 8, wherein the segment is modified such that it does not express NS1 (ΔNS1), derived from H3N8 CIV (Influenza A/canine/NY/dog23/2009).

FIG. 10, comprising FIG. 10A and FIG. 10B, depict the nucleotide sequence of modified segment 8 (FIG. 10A), and the encoded amino acid sequence (FIG. 10B) of the NS1-126 mutant, derived from H3N8 CIV (Influenza A/canine/NY/dog23/2009).

FIG. 11, comprising FIG. 11A and FIG. 11B, depict the nucleotide sequence of modified segment 8 (FIG. 11A), and the encoded amino acid sequence (FIG. 11B) of the NS1-99 mutant, derived from H3N8 CIV (Influenza A/canine/NY/dog23/2009).

FIG. 12, comprising FIG. 12A and FIG. 12B, depict the nucleotide sequence of modified segment 8 (FIG. 12A), and the encoded amino acid sequence (FIG. 12B) of the NS1-73 mutant, derived from H3N8 CIV (Influenza A/canine/NY/dog23/2009).

DETAILED DESCRIPTION

Figures 1A, 1B, 1C:
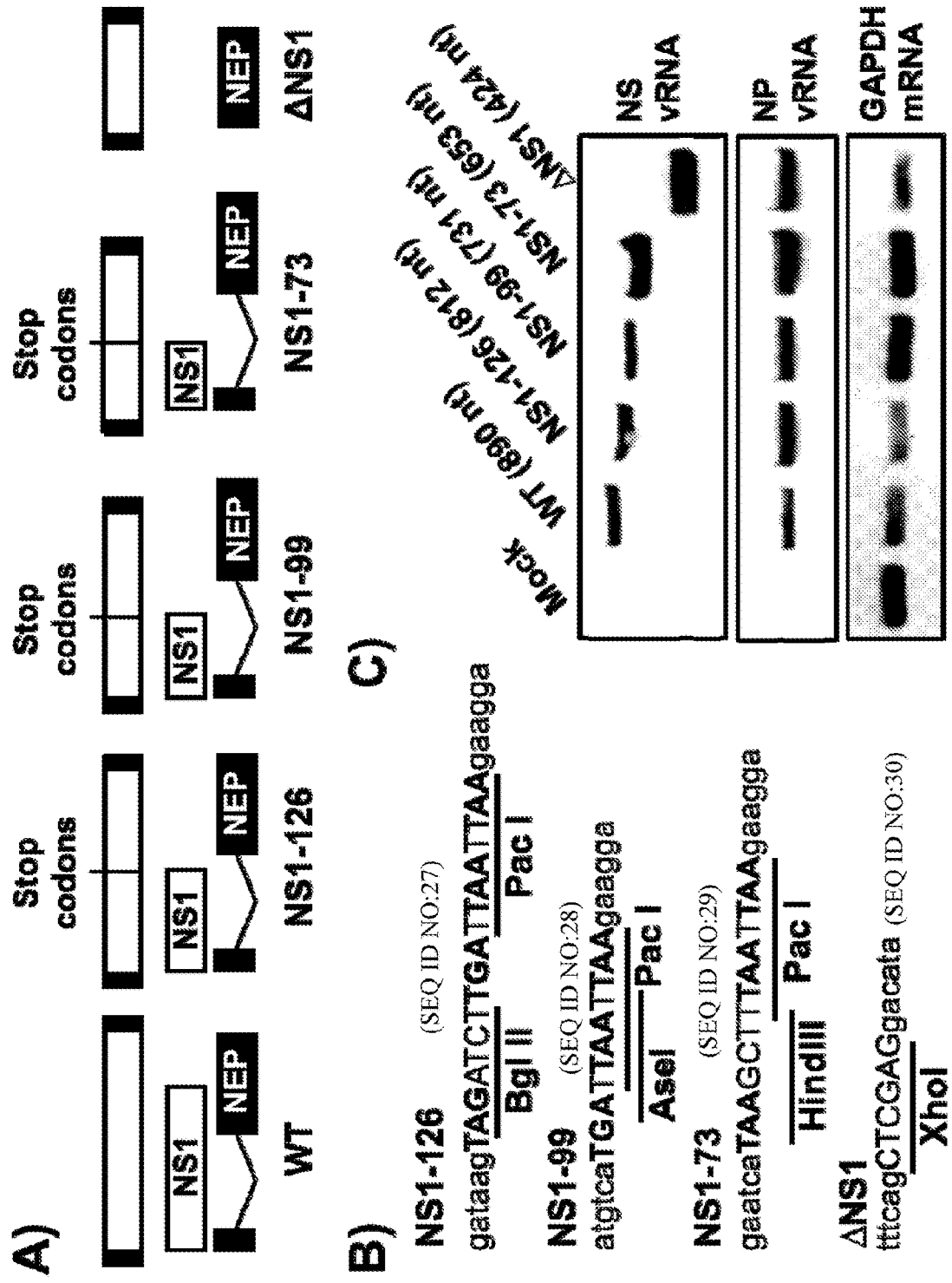
(FIG. 1A and FIG. 1B) Schematic representation of the WT and truncated NS1 H3N8 CIVs. C-terminal truncations were introduced to the NS1 protein, resulting in four constructs encoding the first 126, 99, or 73 amino acids or a deletion ($\Delta$NS1) of the viral NS1 protein. The nuclear export protein (NEP) open reading frame was not altered (FIG. 1A). The viral NS non-coding regions, NCR (black boxes) and the stop codons are indicated. Deletions, stop codons and/or restriction enzymes were introduced in each construct (FIG. 1B). NS1 sequence (lowercase), stop codons (bold, uppercase) and restriction sites (underlined, uppercase) are indicated.
(FIG. 1C) RT-PCR of the WT and truncated NS H3N8 CIVs: MDCK cells were infected (MOI 3) with the indicated H3N8 CIVs. At 20 hours post-infection total RNA was extracted and the presence of vRNAs encoding NS and NP as well as cellular mRNA encoding GAPDH was assessed by RT-PCR. Expected nucleotide (nt) sizes are indicated. The sizes of molecular markers (bp) are indicated to the left.

The present invention relates to compositions and methods for the treatment and prevention of canine influenza virus (CIV) and CIV-related pathology. The present invention is based in part upon the discovery that mutations in segment 8 of the CIV genome, resulting in the truncation of NS1 or the lack of NS1 expression, induces a CIV-specific immune response and can be used to protect against CIV infection. In certain embodiments, the NS1-mutated CIV described herein is a live-attenuated canine influenza vaccine (LACIV).

In certain embodiments, the present invention provides a composition for the treatment and prevention of canine influenza virus (CIV) and CIV-related pathology. In one embodiment, the composition comprises a mutant CIV having one or more mutations in segment 8 of the viral genome. For example, in one embodiment, the mutant CIV encodes mutant NS1. In certain embodiments, mutant NS1 is a truncation mutant, selected from NS1-126, NS1-99, or NS1-73. In one embodiment, the mutant CIV comprises one or more mutations in segment 8 that results in the lack of expression of NS1 (denoted herein as delNS1 or ΔNS1).

In certain embodiments, the present invention provides a method for treating or preventing CIV and CIV-related pathology, comprising administering a composition comprising a mutant CIV described herein. In certain embodiments, the method comprises intranasal delivery of the mutant CIV.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample.

As used herein, the term "autologous" is meant to refer to any material derived from the same individual to which it is later to be re-introduced into the individual.

As used herein, by "combination therapy" is meant that a first agent is administered in conjunction with another agent. "In conjunction with" refers to administration of one treatment modality in addition to another treatment modality. As such, "in conjunction with" refers to administration of one treatment modality before, during, or after delivery of the other treatment modality to the individual. Such combinations are considered to be part of a single treatment regimen or regime.

As used herein, the term "concurrent administration" means that the administration of the first therapy and that of a second therapy in a combination therapy overlap with each other.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein, is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, the term "immune response" includes T-cell mediated and/or B-cell mediated immune responses. Exemplary immune responses include T cell responses, e.g., cytokine production and cellular cytotoxicity, and B cell responses, e.g., antibody production. In addition, the term immune response includes immune responses that are indirectly affected by T cell activation, e.g., antibody production (humoral responses) and activation of cytokine responsive cells, e.g., macrophages. Immune cells involved in the immune response include lymphocytes, such as B cells and T cells (CD4+, CD8+, Th1 and Th2 cells); antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer cells; myeloid cells, such as macrophages, eosinophils, mast cells, basophils, and granulocytes.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A," the presence of a molecule containing epitope A (or free, unlabeled A), in a reaction containing labeled "A" and the antibody, will reduce the amount of labeled A bound to the antibody.

The term "normal temperature" or "normal body temperature" as used herein refers to the temperature of a healthy subject. For example, in certain instances the "normal body temperature" in a human subject is in the range of about 36° C. to about 38° C. In certain instances, in a canine subject, "normal body temperature" is in the range of about 38° C. to about 39.5° C.

The tem "elevated temperature" or "elevated body temperature" as used herein refers to a temperature in a subject that is greater than the "normal body temperature" of a subject of a given organism. In certain instances "elevated body temperature" may be indicative of a fever, infection, or other illness. In certain instances, elevated body temperature in a human subject is greater than about 37° C. In certain instances, elevated body temperature in a canine subject is greater than about 38.5° C.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides immunological compositions and methods useful for the inhibition, prevention and treatment of canine influenza and canine influenza related diseases and disorders. In one embodiment, the immunological composition comprises a live-attenuated virus (LAV).

In one embodiment, the present invention provides a mutant form of a canine influenza virus. For example, it is demonstrated herein that mutations in segment 8 of the CIV genome, resulting the expression of truncated NS1 or the lack of NS1 expression, provides antigen-specific immune responses and protection against CIV. In one embodiment, the mutant CIV provides at least the same antigen-specific immune responses and protection against CIV compared to wildtype CIV. In certain embodiments, the mutant CIV provides greater antigen-specific immune responses and protection against CIV as compared to inactivated CIV.

In general, wild-type influenza viruses contain a segmented genome with 8 segments as described in Table 1 below:

TABLE 1

| Segment | Gene Product |
| --- | --- |
| 1 | PB2 (Polymerase (basic) protein 2) |
| 2 | PB1 (Polymerase (basic) protein 1) |
| 3 | PA (Polymerase (acidic) protein) |
| 4 | HA (Hemagglutinin) |
| 5 | NP (Nucleoprotein) |
| 6 | NA (Neuraminidase) |
| 7 | M1 (Matrix protein 1) and M2 (Matrix protein 2) |
| 8 | NS1 (non-structural protein 1) and NEP/NS2 (non-structural protein 2) |

In certain embodiments, the present invention provides an immunological composition comprising segment 8, wherein segment 8 comprises one or more mutations. For example, in certain embodiments, the immunological composition comprises an LAV, comprising one or more mutations in segment 8.

The present invention also provides methods of preventing, inhibiting, and treating CIV and CIV-related diseases and disorders. In one embodiment, the methods of the invention induce immunity against CIV by generating an immune response directed to CIV. In one embodiment, the methods of the invention induce production of CIV-specific antibodies. In one embodiment, the methods of the invention prevent CIV-related pathology. In one embodiment, the methods of the invention comprise administering an immunological composition comprising a mutant CIV, wherein the mutant CIV comprises one or more mutations in segment 8, to a subject in need thereof In one embodiment, the methods comprise administering an immunological composition to a subject in need thereof, thereby inducing immunity to CIV.

Compositions

The present invention provides immunological compositions that when administered to a subject in need thereof, elicit an immune response directed against canine influenza virus (CIV). In some embodiments, the composition includes polypeptides, nucleotides, vectors, or vaccines. Further, when the compositions are administered to a subject, they elicit an immune response that serves to protect the inoculated subject against canine influenza. As exemplified herein, the composition can be obtained in large quantities for use as a vaccine.

In one embodiment, the present invention provides compositions that are useful as immunomodulatory agents, for example, in stimulating immune responses and in preventing canine influenza and canine influenza-related pathology. In certain embodiments, the composition comprises a live-attenuated virus (LAV).

The immunological compositions can be used as immunostimulatory agents to induce the production of CIV-specific antibodies and protect against canine influenza and canine influenza-related pathology. In one embodiment, the composition of the invention comprises a mutant CIV, wherein the mutant CIV comprises one or more mutations in the viral genome. For example, in one embodiment, the mutant CIV comprises one or more mutations in segment 8 of the viral genome. In one embodiment, the one or more mutations in segment 8 of the viral genome encode a mutant NS1 protein. For example, in one embodiment, the one or more mutations in segment 8 of the viral genome encode a truncation mutant of NS1, where NS1 is truncated at its C-terminus. In one embodiment, the one or more mutations in segment 8 of the viral genome results in the lack of NS1 protein expression. In one embodiment, the mutant segment 8 of the mutant CIV still encodes wildtype NEP/NS2 protein.

In one embodiment, the LACIV is based upon the genome of Influenza A/canine/NY/dog23/2009 H3N8. Wildtype nucleic acid sequences for each segment of Influenza A/canine/NY/dog23/2009 H3N8 and wildtype amino acid sequences for the encoded proteins are summarized in Table 2 below:

TABLE 2

Wildtype sequences for Influenza A/canine/NY/dog23/2009 H3N8

| Segments | Gene Products | |
|---|---|---|
| Segment 1 (SEQ ID NO: 9) | PB2 (SEQ ID NO: 10) | |
| Segment 2 (SEQ ID NO: 11) | PB1 (SEQ ID NO: 12) | |
| Segment 3 (SEQ ID NO: 13) | PA (SEQ ID NO: 14) | |
| Segment 4 (SEQ ID NO: 15) | HA (SEQ ID NO: 16) | |
| Segment 5 (SEQ ID NO: 17) | NP (SEQ ID NO: 18) | |
| Segment 6 (SEQ ID NO: 19) | NA (SEQ ID NO: 20) | |
| Segment 7 (SEQ ID NO: 21) | M1 (SEQ ID NO: 22) | M2 (SEQ ID NO: 23) |
| Segment 8 (SEQ ID NO: 24) | NS1 (SEQ ID NO: 25) | NEP/NS2 (SEQ ID NO: 26) |

In one embodiment, the composition comprises one or more mutations in the nucleic acid sequences of segment 8, encoding NS1 and NEP/NS2 proteins. In one embodiment, certain embodiments, the composition encodes mutant NS1. In one embodiment, the composition encodes a truncation mutant of NS1. In one embodiment, the composition comprises a mutation in segment 8 that results in the lack of expression of NS1. In one embodiment, the composition encodes wildtype NEP/NS2.

In some embodiments, the invention provides a composition comprising one or more mutations in segment 8. For example, in one embodiment, the composition comprises segment 8 having one or more mutation which results in the production of a truncation mutant of NS1, where the truncation mutant of NS1 is truncated at its C-terminus, as compared to wildtype NS1. For example, in one embodiment, the mutant NS1 comprises the amino acid sequence of SEQ ID NO: 25, except having one or more amino acids deleted from the C-terminus. In one embodiment, the mutant NS1 comprises amino acids 1-126 of NS1, referred to herein as NS1-126. For example, in one embodiment, NS1-126 comprises the amino acid sequence of SEQ ID NO: 5. In one embodiment, the mutant NS1 comprises amino acids 1-99 of NS1, referred to herein as NS1-99. For example, in one embodiment, NS1-99 comprises the amino acid sequence of SEQ ID NO: 6. In one embodiment, the mutant NS1 comprises amino acids 1-73 of NS1, referred to herein as NS1-73. For example, in one embodiment, NS1-73 comprises the amino acid sequence of SEQ ID NO: 7.

In one embodiment, the composition comprises a nucleic acid sequence encoding a mutant NS1 having an amino acid sequence of SEQ ID NO: 5, SEQ ID NO: 6, or SEQ ID NO: 7. In one embodiment, the composition comprises a nucleic acid sequence encoding a mutant NS1 that is substantially homologous to SEQ ID NO: 5, SEQ ID NO: 6, or SEQ ID NO: 7. For example, in certain embodiments, the composition comprises a nucleic acid sequence that encodes a mutant NS1 that is at least 50% homologous, at least 60% homologous, at least 70% homologous, at least 80% homologous, at least 90% homologous, at least 95% homologous, at least 98% homologous, at least 99% homologous, or at least 99.5% homologous to SEQ ID NO: 5, SEQ ID NO: 6, or SEQ ID NO: 7.

In one embodiment, the composition comprises a mutant segment 8 comprising the nucleotide sequence of SEQ ID NO: 2. In one embodiment, the composition comprises nucleotide sequence that is substantially homologous to SEQ ID NO: 2. For example, in certain embodiments, the composition comprises a nucleotide sequence that is at least 50% homologous, at least 60% homologous, at least 70% homologous, at least 80% homologous, at least 90% homologous, at least 95% homologous, at least 98% homologous, at least 99% homologous, or at least 99.5% homologous to SEQ ID NO: 2.

In one embodiment, the composition comprises a mutant segment 8 comprising the nucleotide sequence of SEQ ID NO: 3. In one embodiment, the composition comprises nucleotide sequence that is substantially homologous to SEQ ID NO: 3. For example, in certain embodiments, the composition comprises a nucleotide sequence that is at least 50% homologous, at least 60% homologous, at least 70% homologous, at least 80% homologous, at least 90% homologous, at least 95% homologous, at least 98% homologous, at least 99% homologous, or at least 99.5% homologous to SEQ ID NO: 3.

In one embodiment, the composition comprises a mutant segment 8 comprising the nucleotide sequence of SEQ ID NO: 4. In one embodiment, the composition comprises nucleotide sequence that is substantially homologous to SEQ ID NO: 4. For example, in certain embodiments, the composition comprises a nucleotide sequence that is at least 50% homologous, at least 60% homologous, at least 70% homologous, at least 80% homologous, at least 90% homologous, at least 95% homologous, at least 98% homologous, at least 99% homologous, or at least 99.5% homologous to SEQ ID NO: 4.

In one embodiment, the composition comprises segment 8 having one or more mutation which results in the deletion of NS1, where NS1 is not expressed by segment 8, referred to herein as delNS1 or ΔNS1.

In one embodiment, the composition comprises a mutant segment 8 comprising the nucleotide sequence of SEQ ID NO: 1. In one embodiment, the composition comprises nucleotide sequence that is substantially homologous to SEQ ID NO: 1. For example, in certain embodiments, the composition comprises a nucleotide sequence that is at least 50% homologous, at least 60% homologous, at least 70% homologous, at least 80% homologous, at least 90% homologous, at least 95% homologous, at least 98% homologous, at least 99% homologous, or at least 99.5% homologous to SEQ ID NO: 1.

In one embodiment, the composition comprises segment 8 having one or more mutation which results in mutant NS1 or lack of NS1 expression, but still expresses wildtype NEP/NS2. In one embodiment, the composition comprises a nucleic acid sequence encoding a NEP/NS2 having an amino acid sequence of SEQ ID NO: 8. In one embodiment, the composition comprises a nucleic acid sequence encoding a NEP/NS2 that is substantially homologous to SEQ ID NO: 8. For example, in certain embodiments, the composition comprises a nucleic acid sequence that encodes a NEP/NS2 that is at least 50% homologous, at least 60% homologous, at least 70% homologous, at least 80% homologous, at least 90% homologous, at least 95% homologous, at least 98% homologous, at least 99% homologous, or at least 99.5% homologous to SEQ ID NO: 8.

In certain embodiments, the composition comprises one or more mutations in the nucleic acid sequences of segment 8, while comprising wildtype nucleic acid sequences for the rest of the segmented genome. For example, in one embodiment, the composition comprises one or more mutations in segment 8 and comprises wildtype segment 1, segment 2, segment 3, segment 4, segment 5, segment 6, and segment 7.

In certain embodiments, the composition comprises one or more mutations in segment 8, in combination with one or more mutations in one or more other segments of the viral genome.

For example, in one embodiment, the composition further comprises one or more mutations in segment 1 and/or segment 2. In one embodiment, the composition comprises a mutation in segment 1 and/or segment 2, encoding a point mutation in PB2 and/or PB1 that render the CIV temperature sensitive. An exemplary point mutations of PB2 is N265S. Exemplary point mutations of PB1 include a K391E point mutation, a E581G point mutation, and a A661T point mutation, as described in PCT Patent Application PCT/US2016/047715, filed on Aug. 19, 2016, claiming priority to U.S. Provisional Patent Application No. 62/207,571, each of which applications are incorporated by reference in their entirety.

For example, in one embodiment, the composition further comprises one or more mutations in segment 4. In one embodiment, the composition comprises a deletion mutant of segment 4, such that HA is not expressed, as described in PCT Patent Application PCT/US2016/047726, filed on Aug. 19, 2016, claiming priority to U.S. Provisional Patent Application No. 62/207,579, each of which applications are incorporated by reference in their entirety.

In certain embodiments, the composition comprises a mutated segment 8, as described herein, in combination with one or more nucleotide sequences encoding another antigen. For example, in certain embodiments, the composition comprises a mutated segment 8, as described herein, in combination with one or more nucleotide sequences encoding one or more antigens of another virus or strain. For example, in certain aspects, the H3N8 NS1 mutants described herein can be used as a master donor virus (MDV). For example, an MDV comprising an H3N8 modified segment 8 described herein, can be modified to comprise one or more nucleotide sequences encoding one or more of PB2, PB1, PA, NP, HA, NA, M1, M2, NS1, or NEP/NS2 from another influenza strain. As such a composition comprising an H3N8 modified segment 8 described herein can provide protection against a different strain, when the composition expresses an antigen of the different strain. For example, in one embodiment, a composition comprises the backbone of a NS1 mutant H3N8 described herein, further comprising one or more nucleotide sequences encoding one or more of PB2, PB1, PA, NP, HA, NA, M1, M2, NS1, or NEP/NS2 from another influenza strain. In one embodiment, the composition comprises the backbone of a NS1 mutant H3N8 described herein, further comprising one or more nucleotide sequences encoding one or more of HA or NA of a different influenza strain, including but not limited to H3N2 CIV. For example, the composition comprising the backbone of a NS1 mutant H3N8 described herein, may be modified to express one or more viral proteins of a newly emergent strain, thereby providing protection against the newly emergent strain.

In certain embodiments, the composition comprises a polynucleotide encoding a truncation mutant of NS1. In one embodiment, the composition comprises a polynucleotide that results in the lack of NS1 expression. The polynucleotide can be RNA or DNA. In one embodiment, the composition comprises a DNA vaccine.

The nucleic acid sequences include both the DNA sequence that is transcribed into RNA and the RNA sequence that is translated into a polypeptide. According to other embodiments, the polynucleotides of the invention are inferred from the amino acid sequence of the polypeptides of the invention. As is known in the art several alternative polynucleotides are possible due to redundant codons, while retaining the biological activity of the translated polypeptides.

Further, the invention encompasses an isolated nucleic acid comprising a nucleotide sequence having substantial homology to a nucleotide sequence of an isolated nucleic acid encoding a polypeptide disclosed herein. Preferably, the nucleotide sequence of an isolated nucleic acid encoding a polypeptide of the invention is "substantially homologous," that is, is about 60% homologous, more preferably about 70% homologous, even more preferably about 80% homologous, more preferably about 90% homologous, even more preferably, about 95% homologous, and even more preferably about 99% homologous to a nucleotide sequence of an isolated nucleic acid encoding a polypeptide of the invention.

It is to be understood explicitly that the scope of the present invention encompasses homologs, analogs, variants, fragments, derivatives and salts, including shorter and longer polypeptides and polynucleotides, as well as polypeptide and polynucleotide analogs with one or more amino acid or nucleic acid substitution, as well as amino acid or nucleic acid derivatives, non-natural amino or nucleic acids and synthetic amino or nucleic acids as are known in the art, with the stipulation that these modifications must preserve the immunologic activity of the original molecule. Specifically any active fragments of the active polypeptides as well as extensions, conjugates and mixtures are included and are disclosed herein according to the principles of the present invention.

The invention should be construed to include any and all isolated nucleic acids which are homologous to the nucleic acids described and referenced herein, provided these homologous nucleic acids encode polypeptides having the biological activity of the polypeptides disclosed herein.

The skilled artisan would understand that the nucleic acids of the invention encompass a RNA or a DNA sequence encoding a polypeptide of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

Further, any number of procedures may be used for the generation of mutant, derivative or variant forms of a protein of the invention using recombinant DNA methodology well known in the art such as, for example, that described in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York). Procedures for the introduction of amino acid changes in a polypeptide or polypeptide by altering the DNA sequence encoding the polypeptide are well known in the art and are also described in these, and other, treatises.

According to yet another embodiment, composition of the invention, comprising the nucleic acid sequences or combination of nucleic acid sequences of the present invention, is capable of generating a CIV-specific immune response. In another embodiment, the composition of the invention, comprising the nucleic acid sequences or combination of nucleic acid sequences of the present invention, is capable of generating CIV-specific antibodies. In certain embodiments, the composition is able to protect against CIV, including H3N8 CIV and H3N2 CIV.

In one embodiment, the composition of the invention comprises a polypeptide, or a fragment of a polypeptide, a homolog, a variant, a derivative or a salt of a polypeptide having the sequence of any one or more of SEQ ID NO: 5, SEQ ID NO: 6, SEQ ID NO: 7, or SEQ ID NO: 8.

The invention should also be construed to include any form of a polypeptide having substantial homology to the polypeptides disclosed herein. Preferably, a polypeptide which is "substantially homologous" is about 50% homologous, more preferably about 70% homologous, even more preferably about 80% homologous, more preferably about 90% homologous, even more preferably, about 95% homologous, and even more preferably about 99% homologous to amino acid sequence of the polypeptides disclosed herein.

According to yet another embodiment, composition of the invention, comprising the polypeptide or combination of polypeptides of the present invention, is capable of generating a CIV-specific immune response. In another embodiment, the composition of the invention, comprising the polypeptide or combination of polypeptides of the present invention, is capable of generating CIV-specific antibodies. In certain embodiments, the composition is able to protect against CIV, including H3N8 CIV and H3N2 CIV.

The present invention should also be construed to encompass "mutants," "derivatives," and "variants" of the polypeptides of the invention (or of the DNA encoding the same) which mutants, derivatives and variants are polypeptides which are altered in one or more amino acids (or, when referring to the nucleotide sequence encoding the same, are altered in one or more base pairs) such that the resulting polypeptide (or DNA) is not identical to the sequences recited herein, but has the same biological property as the polypeptides disclosed herein.

Mutated Virus and LAV

The invention relates in part to the generation, selection and identification of mutant CIV that generate a CIV-specific immune response, and the use of such viruses in vaccine and pharmaceutical formulations. In certain embodiments, the mutant CIV is a live-attenuated CIV (LACIV).

As described herein, in certain embodiments the mutant CIV comprises one or more mutations in segment 8, the results in either the lack of NS1 expression or the expression of truncation mutants of NS1. The mutant CIV induces CIV-specific immune responses and antibody production, and is thus able to protect against CIV and CIV-related pathology.

Any mutant virus or strain which has at least one mutation can be selected and used in accordance with the invention. In one embodiment, naturally occurring mutants or variants, or spontaneous mutants can be selected that include at least one mutation in segment 8, as described elsewhere herein. In another embodiment, mutant viruses can be generated by exposing the virus to mutagens, such as ultraviolet irradiation or chemical mutagens, or by multiple passages and/or passage in non-permissive hosts. Screening in a differential growth system can be used to select for those mutants having at least one mutation in segment 8, as described elsewhere herein. For viruses with segmented genomes, the attenuated phenotype can be transferred to another strain having a desired antigen by reassortment, (i.e., by coinfection of the attenuated virus and the desired strain, and selection for reassortants displaying both phenotypes).

In another embodiment, mutations can be engineered into an influenza virus, including, but not limited to H3N8 CIV or H3N2 CIV using "reverse genetics" approaches. In this way, natural or other mutations which confer the attenuated phenotype can be engineered into vaccine strains. For example, deletions, insertions, or substitutions of the coding region of segment 8, encoding NS1 can be engineered. Deletions, substitutions or insertions in the non-coding region of segment 8 are also contemplated. To this end, mutations in the signals responsible for the transcription, replication, polyadenylation and/or packaging of segment 8 can be engineered. In certain embodiments, the mutation comprises the insertion of a stop signal, which terminates translation of the NS1 protein, thereby producing a truncated NS1 mutant.

In certain instances, the reverse genetics technique involves the preparation of synthetic recombinant viral RNAs that contain the non-coding regions of the negative strand virus RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. In some instances, a more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. patent application Ser. No. 09/152,845; in International Patent Publications PCT WO97/12032 published Apr. 3, 1997; WO96/34625 published Nov. 7, 1996; in European Patent Publication EP-A780475; WO 99/02657 published Jan. 21, 1999;. WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 47SA1 published Jun. 25, 1997, each of which is incorporated by reference herein in its entirety.

Attenuated viruses generated by the reverse genetics approach can be used in the vaccine and pharmaceutical formulations described herein. Reverse genetics techniques can also be used to engineer additional mutations to other viral genes important for vaccine production—i.e., the epitopes of useful vaccine strain variants can be engineered into the attenuated virus. Alternatively, completely foreign epitopes, including antigens derived from other viral or non-viral pathogens can be engineered into the attenuated strain.

In an alternate embodiment, a combination of reverse genetics techniques and reassortant techniques can be used to engineer attenuated viruses having the desired epitopes. For example, an attenuated virus (generated by natural selection, mutagenesis or by reverse genetics techniques) and a strain carrying the desired vaccine epitope (generated by natural selection, mutagenesis or by reverse genetics techniques) can be co-infected in hosts that permit reassortment of the segmented genomes. Reassortants that display both the attenuated phenotype and the desired epitope can then be selected.

The attenuated virus of the present invention can itself be used as the active ingredient in vaccine or pharmaceutical formulations. In certain embodiments, the attenuated virus can be used as the vector or "backbone" of recombinantly produced vaccines. To this end, the "reverse genetics" technique can be used to engineer mutations or introduce foreign epitopes into the attenuated virus, which would serve as the "parental" strain. In this way, vaccines can be designed for immunization against strain variants, or in the alternative, against completely different infectious agents or disease antigens.

For example, in one embodiment, the immunological composition of the invention comprises a mutant virus, engineered to express one or more epitopes or antigens of CIV along with epitopes or antigens of another pathogen. For example, the virus can be engineered to express neutralizing epitopes of other preselected strains. Alternatively, epitopes of other viruses can be built into the mutant virus. Alternatively, epitopes of non-viral infectious pathogens (e.g., parasites, bacteria, fungi) can be engineered into the virus.

In one embodiment, the viruses selected for use in the invention is capable of inducing a robust anti-CIV response in the host—a feature which contributes to the generation of a strong immune response when used as a vaccine, and which has other biological consequences that make the viruses useful as pharmaceutical agents for the prevention and/or treatment of other viral infections, or other diseases.

The mutant viruses, which induce a CIV-specific immune response in hosts, may also be used in pharmaceutical formulations for the prophylaxis or treatment of other influenza infections, or influenza-related pathology. In this regard, the tropism of the virus can be altered to target the virus to a desired target organ, tissue or cells in vivo or ex vivo. Using this approach, the CIV-specific immune response can be induced locally, at the target site, thus avoiding or minimizing the side effects of systemic treatments. To this end, the attenuated virus can be engineered to express a ligand specific for a receptor of the target organ, tissue or cells.

Vaccine

In certain aspects, the immunological composition is useful as a vaccine, where the immunological composition induces an immune response to the antigen in a cell, tissue or mammal. Preferably, the vaccine induces a protective immune response in the mammal. As used herein, an "immunological composition" may comprise, by way of examples, a mutant virus, a live-attenuated virus (LAV), an antigen (e.g., a polypeptide), a nucleic acid encoding an antigen (e.g., an antigen expression vector), or a cell expressing or presenting an antigen or cellular component. In particular embodiments the immunological composition comprises or encodes all or part of any polypeptide antigen described herein, or an immunologically functional equivalent thereof. In other embodiments, the immunological composition is in a mixture that comprises an additional immunostimulatory agent or nucleic acids encoding such an agent. Immunostimulatory agents include but are not limited to an additional antigen, an immunomodulator, an antigen presenting cell or an adjuvant. In other embodiments, one or more of the additional agent(s) is covalently bonded to the antigen or an immunostimulatory agent, in any combination. In certain embodiments, the antigenic composition is conjugated to or comprises an HLA anchor motif amino acids.

In the context of the present invention, the term "vaccine" refers to a substance that induces anti-CIV immunity or suppresses CIV upon inoculation into an animal.

The invention encompasses vaccine formulations comprising a mutant virus, wherein the mutant virus is a canine influenza virus (CIV). In one embodiment, the vaccine comprises a mutant CIV comprising one or more mutations in segment 8, and a suitable excipient. The virus used in the vaccine formulation may be selected from naturally occurring mutants or variants, mutagenized viruses or genetically engineered viruses. Mutant strains of CIV can also be generated via reassortment techniques, or by using a combination of the reverse genetics approach and reassortment techniques. Naturally occurring variants include viruses isolated from nature as well as spontaneous occurring variants generated during virus propagation. The mutant virus can itself be used as the active ingredient in the vaccine formulation. Alternatively, the mutant virus can be used as the vector or "backbone" of recombinantly produced vaccines. To this end, recombinant techniques such as reverse genetics (or, for segmented viruses, combinations of the reverse genetics and reassortment techniques) may be used to engineer mutations or introduce foreign antigens into the attenuated virus used in the vaccine formulation. In this way, vaccines can be designed for immunization against strain variants, or in the alternative, against completely different infectious agents or disease antigens.

In one embodiment, the vaccine formulation comprises a plurality of mutant CIV. For example, in one embodiment, the vaccine formulation may comprise one or more of the mutant CIV, described herein, in combination with other mutant CIV that induce an anti-CIV immune response. For example, in one embodiment, the vaccine formulation comprises a live-attenuated CIV having one or more mutations in segment 1 and/or segment 2. In one embodiment, the vaccine formulation comprises a mutant single-cycle infectious CIV comprising a deletion mutant in segment 4, resulting in the lack of HA expression.

In one embodiment, the present invention comprises a method of generating a mutant virus, comprising contacting a host cell with a polynucleotide comprising the nucleic acid sequences of segment 8, having one or more mutations, described elsewhere herein.

Propagation of the virus in culture is known to persons in the art. Briefly, the virus is grown in the media compositions in which the host cell is commonly cultured. Suitable host cells for the replication of CIV include, e.g., Vero cells, BHK cells, MDCK cells, 293 cells COS cells, and CEK cells, including 293T cells, COS7 cells. Commonly, co-cultures including two of the above cell lines, e.g., MDCK cells and either 293T or COS cells are employed at a ratio, e.g., of 1:1, to improve replication efficiency. Typically, cells are cultured in a standard commercial culture medium, such as Dulbecco's modified Eagle's medium supplemented with serum (e.g., 10% fetal bovine serum), or in serum free medium, under controlled humidity and $CO_2$ concentration suitable for maintaining neutral buffered pH (e.g., at pH between 7.0 and 7.2). Optionally, the medium contains antibiotics to prevent bacterial growth, e.g., penicillin, streptomycin, etc., and/or additional nutrients, such as L-glutamine, sodium pyruvate, non-essential amino acids, additional supplements to promote favorable growth characteristics, e.g., trypsin, β-mercaptoethanol, and the like.

Procedures for maintaining mammalian cells in culture have been extensively reported, and are known to those of skill in the art. General protocols are provided, e.g., in Freshney (1983) Culture of Animal Cells: Manual of Basic Technique, Alan R. Liss, New York; Paul (1975) Cell and Tissue Culture, $5^{th}$ ed., Livingston, Edinburgh; Adams (1980) Laboratory Techniques in Biochemistry and Molecular Biology-Cell Culture for Biochemists, Work and Burdon (eds.) Elsevier, Amsterdam. Additional details regarding tissue culture procedures of particular interest in the production of influenza virus in vitro include, e.g., Merten et al. (1996) Production of influenza virus in cell cultures for vaccine preparation. In Cohen and Shafferman (eds) Novel Strategies in Design and Production of Vaccines, which is incorporated herein in its entirety. Additionally, variations in such procedures adapted to the present invention are readily determined through routine experimentation.

Cells for production of a virus can be cultured in serum-containing or serum free medium. In some case, e.g., for the preparation of purified viruses, it is desirable to grow the host cells in serum free conditions. Cells can be cultured in small scale, e.g., less than 25 ml medium, culture tubes or flasks or in large flasks with agitation, in rotator bottles, or on microcarrier beads (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor) in flasks, bottles or reactor cultures. Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface. For commercial production of viruses, e.g., for vaccine production, it is often desirable to culture the cells in a bioreactor or fermenter. Bioreactors are available in volumes from under 1 liter to in excess of 100 liters, e.g., Cyto3 Bioreactor (Osmonics, Minnetonka, Minn.); NBS bioreactors (New Brunswick Scientific, Edison, N.J.); laboratory and commercial scale bioreactors from B. Braun Biotech International (B. Braun Biotech, Melsungen, Germany).

Virtually any heterologous gene sequence may be constructed into the viruses of the invention for use in vaccines. Preferably, epitopes that induce a protective immune response to any of a variety of pathogens, or antigens that bind neutralizing antibodies may be expressed by or as part of the viruses. For example, heterologous gene sequences that can be constructed into the viruses of the invention for use in vaccines include but are not limited to epitopes of human immunodeficiency virus (HIV) such as gp120; hepatitis B virus surface antigen (HBsAg); the glycoproteins of herpes virus (e.g. gD, gE); VP1 of poliovirus; antigenic determinants of non-viral pathogens such as bacteria and parasites, to name but a few. In another embodiment, all or portions of immunoglobulin genes may be expressed. For example, variable regions of anti-idiotypic immunoglobulins that mimic such epitopes may be constructed into the viruses of the invention. In yet another embodiment, tumor associated antigens may be expressed.

Either a live recombinant viral vaccine or an inactivated recombinant viral vaccine can be formulated. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification.

Many methods may be used to introduce the vaccine formulations described above, these include but are not limited to introduction intranasally, intratracheally, orally, intradermally, intramuscularly, intraperitoneally, intravenously, and subcutaneously. It may be preferable to introduce the virus vaccine formulation via the natural route of infection of the pathogen for which the vaccine is designed, or via the natural route of infection of the parental virus.

A vaccine of the present invention, comprising a mutant CIV could be administered once. Alternatively, a vaccine of the present invention, comprising a mutant CIV, could be administered twice or three or more times with a suitable interval between doses. Alternatively, a vaccine of the present invention, comprising a mutant CIV, could be administered as often as needed to an animal, preferably a mammal.

Methods

The invention provides a method for treating or preventing canine influenza infection or a CIV-related disease or disorder. In one embodiment, the method comprises administering an immunological composition comprising a mutant CIV. In one embodiment, the method comprises administering an immunological composition comprising a mutant CIV comprising one or more mutations in segment 8, to a subject in need thereof.

In certain embodiments, the mutant CIV induces an enhanced immune response as compared to an inactivated CIV. For example, in certain embodiments, the induced immune response of mutant CIV is 2-fold more, 3-fold more, 5-fold more, 10-fold more, 15-fold more, 20-fold more, 50-fold more, 100-fold more, 500-fold more, or 1000-fold more, than inactivated CIV. The immune response induced the mutant CIV can be measured using standard assays. For example, in certain embodiments, the immune response induced by mutant CIV is measured by detecting the amount of CIV-specific antibodies produced in the subject following administration of mutant CIV.

The therapeutic compositions of the invention may be administered prophylactically or therapeutically to subjects suffering from, or at risk of, or susceptible to, developing the disease or condition. Such subjects may be identified using standard clinical methods. In the context of the present invention, prophylactic administration occurs prior to the manifestation of overt clinical symptoms of disease, such that a disease or disorder is prevented or alternatively delayed in its progression. In the context of the field of medicine, the term "prevent" encompasses any activity which reduces the burden of mortality or morbidity from disease. Prevention can occur at primary, secondary and tertiary prevention levels. While primary prevention avoids the development of a disease, secondary and tertiary levels of prevention encompass activities aimed at preventing the progression of a disease and the emergence of symptoms as well as reducing the negative impact of an already established disease by restoring function and reducing disease-related complications.

In certain embodiments, the subject is a mammal. For example, the subject may include, but is not limited to, a human, primate, cow, horse, sheep, pig, dog, cat, or rodent. In one embodiment, the subject is a dog. The method may be used to treat or prevent CIV or CIV-related pathology in any breed or species of dog. In certain embodiments, the relative amount of active ingredient in a single dose, or the frequency of doses, will vary depending on the age, sex, weight, or breed of subject (e.g. dog).

The composition may be combined with an adjuvant. An adjuvant refers to a compound that enhances the immune response when administered together (or successively) with the immunological composition. Examples of suitable adjuvants include cholera toxin, salmonella toxin, alum and such, but are not limited thereto. Furthermore, a vaccine of this invention may be combined appropriately with a pharmaceutically acceptable carrier. Examples of such carriers are sterilized water, physiological saline, phosphate buffer, culture fluid and such. Furthermore, the vaccine may contain as necessary, stabilizers, suspensions, preservatives, surfactants and such. The vaccine is administered systemically or locally. Vaccine administration may be performed by single administration or boosted by multiple administrations.

Administration

In one embodiment, the methods of the present invention comprise administering an immunological composition of the invention directly to a subject in need thereof. Administration of the composition can comprise, for example, intranasal, intramuscular, intravenous, peritoneal, subcutaneous, intradermal, as well as topical administration.

Furthermore, the actual dose and schedule can vary depending on whether the compositions are administered in combination with other pharmaceutical compositions, or depending on inter-individual differences in pharmacokinetics, drug disposition, and metabolism. One skilled in the art can easily make any necessary adjustments in accordance with the exigencies of the particular situation.

Pharmaceutical Compositions

The present invention envisions treating or preventing CIV or CIV-related pathology in a mammal by the administration of a therapeutic composition of the invention to a mammal in need thereof. Administration of the composition in accordance with the present invention may be continuous or intermittent, depending, for example, upon the recipient's physiological condition, whether the purpose of the administration is therapeutic or prophylactic, and other factors known to skilled practitioners. The administration of the compositions of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art.

The present invention encompasses pharmaceutical compositions comprising a mutant CIV to be used as anti-viral agents or as agents against CIV-related diseases and disorders. The pharmaceutical compositions have utility as an anti-viral prophylactic and may be administered to a subject at risk of getting infected or is expected to be exposed to a virus. For example, subjects traveling to parts of the world where CIV is prevalent can be administered a pharmaceutical composition of the invention. In certain embodiments, subjects who are expected to be in contact with other subjects at risk, can be administered a pharmaceutical composition of the invention.

The mutant CIV of the invention may be engineered using the methods described herein to express proteins or peptides which would target the viruses to a particular site. In one embodiment, where the site to be targeted expresses a receptor to a growth factor, e.g., VEGF, EGF, or PDGF, the LACIV may be engineered to express the appropriate growth factor or portion(s) thereof. Thus, in accordance with the invention, the mutant CIV may be engineered to express any target gene product, including peptides, proteins, such as enzymes, hormones, growth factors, antigens or antibodies, which will function to target the virus to a site in need of anti-viral, antibacterial, anti-microbial or anti-cancer activity.

Methods of introduction include but are not limited to intradermal, intramuscular, intraperitoneal, intravenous, subcutaneous, intranasal, epidural, and oral routes. The pharmaceutical compositions of the present invention may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, in a preferred embodiment it may be desirable to introduce the pharmaceutical compositions of the invention into the lungs by any suitable route. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In certain embodiments, the pharmaceutical composition is a veterinary pharmaceutical composition suitable for administration to a veterinary subject, including but not limited to a canine subject. Exemplary canine subjects include dogs, wolves, foxes, coyotes, and jackals.

In certain embodiments, the veterinary pharmaceutical composition is "palatable," meaning an oral veterinary composition that is readily accepted by canines, including dogs, without any coaxing or with some coaxing. Palatable compositions are compositions that score at least 2 using a palatability assessment method wherein dog owners score the composition from 0 to 3, wherein dogs scoring 0 do not consume the composition; dogs scoring 1 consume the composition after some time; dogs scoring 2 consume the composition with some coaxing and dogs scoring 3 consume the composition readily. A skilled person is well-versed in these palatability standards and scoring regimes. In another embodiment, the daily dose for dogs may be around 100 mg/kg. Veterinary pharmaceutical agents that may be included in the compositions of the invention are well-known in the art (see e.g. Plumb' Veterinary Drug Handbook, 5th Edition, ed. Donald C. Plumb, Blackwell Publishing, (2005) or The Merck Veterinary Manual, 9th Edition, (January 2005)).

In yet another embodiment, the pharmaceutical composition can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger & Peppas, 1983, J. Macromol. Sci. Rev. Macromol. Chem. 23:61; see also Levy et al., 1985, Science 228:190; During et al., 1989, Ann. Neurol. 25:351 (1989); Howard et al., 1989, J. Neurosurg. 71:105). In yet another embodiment, a controlled release system can be placed in proximity of the composition's target, i.e., the lung, thus requiring only a fraction of the systemic dose (see, e.g., Goodson, 1984, in Medical Applications of Controlled Release, supra, vol. 2, pp. 115-138). Other controlled release systems are discussed in the review by Langer (1990, Science 249:1527-1533).

The pharmaceutical compositions of the present invention comprise a therapeutically effective amount of the attenuated virus, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water and the like. These compositions can take the form of solutions, suspensions, emulsion, tablets, pills, capsules, powders, sustained-release formulations and the like. These compositions can be formulated as a suppository. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

The amount of the pharmaceutical composition of the invention which will be effective in the treatment or prevention of a particular disease or disorder will depend on the nature of the disease or disorder, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Canine Influenza Viruses with Modified NS1 Proteins for the Development of Live-attenuated Vaccines Influenza non-structural (NS) segment 8 encodes the non-structural protein 1 (NS1) from the full-length transcript, as well as the nuclear export protein (NEP) from pre-mRNA splicing (Hale et al., 2008, The Journal of general virology, 89:2359-2376, Lamb et al., 1980, Proceedings of the National Academy of Sciences, 77:1857-1861). NS1 is a multifunctional protein that is mainly involved in counteracting the antiviral type I interferon (IFN) response (Garcia-Sastre et al., 1998, Virology, 252:324-330, Hale et al., 2008, The Journal of general virology, 89:2359-2376, Steidle et al., 2010, J Virol, 84:12761-12770), and also contributes to viral virulence and pathogenesis (Geiss et al., 2002, Proceedings of the National Academy of Sciences, 99:10736-10741, Nogales et al., 2014, J Virol, 88:10525-10540). Because of NS1's ability to hijack the host immune response, a variety of potential vaccine strategies have been developed that are based on the use of modified NS1 proteins as a mean for virus attenuation (Falcon et al., 2005, The Journal of general virology, 86:2817-2821, Ferko et al., 2004, J Virol, 78:13037-13045, Quinlivan et al., 2005, J Virol, 79:8431-8439, Richt et al., 2009, Current topics in microbiology and immunology, 333:177-195, Steel et al., 2009, J Virol 83:1742-1753, Vincent et al., 2007, Vaccine 25:7999-8009). Equine (Quinlivan et al., 2005, J Virol, 79:8431-8439), swine (Richt et al., 2006, J Virol 80:11009-11018, Solorzano et al., 2005, J Virol, 79:7535-7543, Vincent et al., 2007, Vaccine, 25:7999-8009), avian (Choi et al., 2015, Archives of virology, 160:1729-1740, Steel et al., 2009, J Virol, 83:1742-1753, Wang et al., 2008, Vaccine, 26:3580-3586), and human (Baskin et al., 2007, J Virol, 81:11817-11827, Pica et al., 2012, J Virol, 86:10293-10301) IAVs with partial truncations or deletions in the viral NS1 protein are all attenuated in vitro and in vivo (Pica et al., 2012, J Virol, 86:10293-10301, Quinlivan et al., 2005, J Virol, 79:8431-8439, Steel et al., 2009, J Virol, 83:1742-1753, Vincent et al., 2007, Vaccine, 25:7999-8009). These NS1 mutant IAVs are also able to induce protective immune response in mice (Hai et al., 2008, J Virol, 82:10580-10590, Pica et al., 2012, J Virol, 86:10293-10301, Talon et al., 2000, Proceedings of the National Academy of Sciences, 97:4309-4314), horses (Quinlivan et al., 2005, J Virol, 79:8431-8439), pigs (Richt et al., 2006, J Virol, 80:11009-11018, Solorzano et al., 2005, J Virol, 79:7535-7543, Vincent et al., 2007, Vaccine, 25:7999-8009), birds (Choi et al., 2015, Archives of virology, 160:1729-1740, Steel et al., 2009, J Virol, 83:1742-1753, Wang et al., 2008, Vaccine, 26:3580-3586), and macaques (Baskin et al., 2007, J Virol, 81:11817-11827) and therefore, they represent LAIV candidates for prevention of IAV infections.

Canine Influenza Virus (CIV) H3N8 is the causative agent of canine influenza, a common and contagious respiratory disease of the dog. CIV originated from the transfer of H3N8 Equine Influenza Virus (EIV) into canine populations around 1999. Since that time CIV has continued to infect and spread among dog populations. Currently, only inactivated influenza vaccines (IIV) are commercially available for the prevention of CIV H3N8. However, live-attenuated influenza vaccines (LAIV) are known to provide better immunogenicity and protection efficacy than IIVs. The influenza virus non-structural protein 1 (NS1) is a virulence factor that offers an attractive target for the preparation of attenuated viruses for use as LAIVs. Described herein is the development and manufacture of a genetically engineered A/canine/NY/dog23/2009 in order to generate LAIV candidates. To this end, reverse genetics technology was used to generate viruses containing C-terminal truncations of NS1 (NS1-73, NS1-99 and NS1-126) or an entire NS1 deletion (ΔNS1). All recombinant viruses replicated efficiently in MDCK cells in spite of being impaired in their ability to inhibit the type I interferon (IFN) response. Compared with wild-type H3N8 CIV, a single intranasal inoculation of the NS1 mutant viruses resulted in lower levels of replication in vivo, while retaining immunogenicity and conferring homologous protection against wild type virus challenge. Immunogenicity and protection efficacy was also better than that observed with a commercially available IIV (Nobivac). This is the first description of a LAIV for the prevention and control of H3N8 CIV in dogs.

The materials and methods employed in these experiments are now described.

Cells and Viruses

Human embryonic kidney 293T (293T; ATCC CRL-11268) and Madin-Darby canine kidney (MDCK; ATCC CCL-34) cells were grown at 37° C. with 5% CO2 in Dulbecco's modified Eagle's medium (DMEM; Mediatech, Inc.), 10% fetal bovine serum (FBS), and 1% PSG (penicillin, 100 units/ml; streptomycin 100 µg/ml; L-glutamine, 2 mM) (Nogales et al., 2014, J Virol, 88:10525-10540).

Influenza A/canine/NY/dog23/2009 H3N8 WT (Feng et al., 2015, J Virol, 89:6860-6873) and NS1 truncated (NS1-73, NS1-99 and NS1-126) or deleted (ΔNS1) NS1 mutants were grown in MDCK cells at 33° C. For infections, virus stocks were diluted in phosphate buffered saline (PBS), 0.3% bovine albumin (BA) and 1% PS (PBS/BA/PS). After viral infections, cells were maintained in DMEM with 0.3% BA, 1% PSG, and 1 µg/ml TPCK-treated trypsin (Sigma) (Martinez-Sobrido et al., 2010, Journal of visualized experiments, doi: (42)10.3791/2057). Recombinant Newcastle Disease Virus (rNDV) expressing the green fluorescent protein (GFP), rNDV-GFP, was also used in this experiment (Martinez-Sobrido et al., 2006, J Virol, 80:9192-9199, Park et al., 2003, J Virol, 77:1501-1511).

Construction of Plasmids

The ambisense pDZ plasmid (Quinlivan et al., 2005, J Virol, 79:8431-8439) encoding the NS gene (Feng et al., 2015, J Virol, 89:6860-6873) was used to engineer the four NS1 mutants: pDZ-NS1-73 (encoding the first 73 amino acids of NS1), pDZ-NS1-99 (encoding the first 99 amino acids of NS1), pDZ-NS1-126 (encoding the first 126 amino acids of NS1) and pDZ-ΔNS1 (deletion of the entire NS1). Truncations were generated by inverse PCR using primers designed to introduce deletions together with stop codons into the recombinant NS segments (FIG. 1A and FIG. 1B) (Quinlivan et al., 2005, J Virol, 79:8431-8439). The presence of introduced mutations was confirmed by sequencing.

The nucleotide sequences encoding the NS1 mutants are provided in SEQ ID NOs: 1-4, while the amino acid sequences of the NS1 truncation mutants are provided in SEQ IDs NOs 5-7 (FIG. 9 through FIG. 12).

Rescue of Recombinant H3N8 CIVs

Viruses were rescued as previously demonstrated (Martinez-Sobrido et al., 2010, Journal of visualized experiments, doi: (42)10.3791/2057). Briefly, co-cultures (1:1) of 293T/MDCK cells (6-well plate format, $10^6$ cells/well) were co-transfected in suspension, using Lipofectamine 2000 (Invitrogen), with 1 µg of the seven-ambisense WT plasmids (43) (pDZ-PB2, -PB1, -PA, -HA, -NP, -NA, -M,) plus the ambisense WT NS plasmid (pDZ-NS) or the NS1 mutant constructs (pDZ-ΔNS1, -NS1-73, -NS1-99 and -NS1-126). At 12 h post-transfection, medium was replaced with DMEM supplemented with 0.3% BA, 1% PSG, and 1.0 µg/ml TPCK-treated trypsin (Sigma). Virus-containing tissue culture supernatants (TCS) were collected 2-3 days post-transfection, clarified, and used to infect fresh MDCK cells. At 3 days post-infection (p.i), recombinant H3N8 CIVs were plaque purified and grown in MDCK cells (Nogales et al., 2014, J Virol, 88:10525-10540). Virus stocks were titrated by standard plaque assay (plaque forming units, PFU/ml) in MDCK cells (Nogales et al., 2014, J Virol, 88:10525-10540).

RT-PCR

Total RNA from mock or CIV-infected MDCK cells (multiplicity of infection [MOI] 3) was collected at 20 h p.i and purified using TRIzol reagent (Invitrogen) according to the manufacturer's specifications. cDNA synthesis for NS or NP viral (v)RNAs was performed using SuperScript® II Reverse Transcriptase (Invitrogen) and specific primers. cDNA synthesis of canine GAPDH mRNA was performed using a dT oligonucleotide (Invitrogen). cDNAs were used as templates for semi-quantitative PCR with primers specific for the NS and NP vRNAs and the cellular GAPDH mRNA.

Virus Growth Kinetics and Plaque Assays

Confluent monolayers of MDCK cells (12-well plate format, triplicates, $5\times10^5$ cells/well) were infected (MOI 0.001) and placed at 33° C. or 37° C. Tissue culture supernatants were collected at various times p.i and viral titers were determined by immunofocus assay (fluorescent forming units, FFU]/ml) in MDCK cells (Nogales et al., 2014, J Virol, 88:10525-10540). The mean value and standard deviation was calculated using Microsoft Excel. For plaque assays, confluent MDCK cell monolayers (6-well plate format, 106 cells/well) were infected with the indicated CIVs. One hour after infection, monolayers were overlaid with agar and incubated for 3 days at 33° C. Cells were then fixed with 4% paraformaldehyde (PFA), and the overlays removed. Fixed cells were permeabilized (0.5% Triton X-100 in PBS for 15 minutes at room temperature) and used for immunostaining (Nogales et al., 2014,Virology, 476C: 206-216) using the anti-NP monoclonal antibody (MAb) HB-65 (ATTC) and the Vectastain ABC kit and DAB HRP Substrate Kit (Vector), according to manufacturer's specifications.

Bioassay to Assess Interferon Production

The levels of type I interferon (IFN) produced in CIV-infected cells were determined by using confluent monolayers of MDCK cells (12-well format, triplicates, $5\times10^5$ cells/well) constitutively expressing GFP-CAT and firefly luciferase (FFluc) under the control of the IFNβ promoter (MDCK IFNβ GFP-CAT/FFluc) (Hai et al., J Virol, 82:10580-10590). These cells were mock infected or infected (MOI 3) with either WT or NS1 mutant H3N8 CIVs. Infection levels were evaluated by immunofluorescence using the anti-NP MAb HB-65. At 12 h p.i., activation of the IFNβ promoter was determined by assessing GFP expression under a fluorescence microscope, and also by quantifying FFluc activity from cell lysates using a luciferase reporter assay (Promega) and a Lumicount luminometer. Supernatants of infected MDCK cells were also collected and viruses were inactivated by exposure to shortwave (254 nm) UV radiation for 10 min at a distance of 6 cm (Nogales et al., 2014, J Virol, 88:10525-10540). Fresh MDCK cells seeded in 96-well plates ($5\times10^4$ cells/well, triplicates) were treated with UV-inactivated supernatants for 24 h and then infected (MOI 3) with rNDV-GFP (Nogales et al., 2014, J Virol, 88:10525-10540). GFP intensity was measured 14 h p.i. using a microplate reader (DTX880; Beckman Coulter). MDCK cells were used as experimental controls and were mock treated or treated with 100 or 1000 units (U) of universal IFN (PBL Assay Science). GFP expression of mock-treated cells infected with rNDV-GFP were determined to be 100%. Mean values and SDs were calculated using Microsoft Excel.

Mice Experiments

Viral replication, immunogenicity and protection efficacy, was evaluated using 5 to 7-week-old female C57BL/6 mice, which were purchased from the National Cancer Institute (NCI) and maintained under specific pathogen-free conditions for one week. Mice were anesthetized intraperitoneally (i.p.) with 2,2,2-tribromoethanol (Avertin; 240 mg/kg of body weight) and inoculated intranasally (i.n.) with the indicated amounts of H3N8 CIVs in a final volume of 30 µl. Alternatively, 100 µl of a commercially available, inactivated CIV H3N8 vaccine ("Nobivac", Merck Animal Health) was inoculated intramuscularly (i.m). CIV H3N8 replication was determined by measuring viral titers in the lungs of infected mice at days 2 and 4 p.i. To that end, three mice from each group were euthanized and lungs were collected and homogenized. Mice were euthanized by administration of a lethal dose of avertin and exsanguination. Virus titers were determined by immunofocus assay (FFU/ml). Mouse sera were collected by submandibular bleeding 24 hours prior to viral challenges and evaluated for the presence of influenza virus total antibodies.

Elisa

Enzyme-linked immunosorbent assays (ELISAs) were performed (Nogales et al., 2014, J Virol, 88:10525-10540) by coating 96-well plates for 16 hours at 4° C. with lysates from mock-, or CIV WT infected MDCK cells. The coated wells were blocked with PBS containing 1% BSA, and then plates were incubated with 1:2 fold dilutions of serum (starting dilution of 1:50) for 1 hour at 37° C. After incubation, plates were washed with PBS, and incubated with HRP-conjugated goat anti-mouse IgG (1:2,000; Southern Biotech) for 1 hour at 37° C. Reactions were developed with tetramethylbenzidine (TMB) substrate (BioLegend) for 10 minutes at room temperature, quenched with 2N $H_2SO_4$, and read at 450 nm (Vmax kinetic microplate reader; Molecular Devices).

HAI Assays

Hemagglutination inhibition (HAI) assays were used to assess the presence of neutralizing antibodies (NAbs). Mouse sera was treated with receptor-destroying enzyme (RDE; Denka Seiken) and heat inactivated for 30 minutes at 56° C. Sera was then serially 2-fold diluted in 96-well V-bottom plates and mixed 1:1 with 4 hemagglutinating units (HAU) of H3N8 CIV for 30 min at room temperature. The HAI titers were determined by adding 0.5% turkey red blood cells (RBCs) to the virus-antibody mixtures for 30 min on ice (Nogales et al., 2014, J Virol, 88:10525-10540). The GMT and SD from individual mice (n=4) was calculated from the last well where hemagglutination was inhibited, using Microsoft Excel.

Canine Tracheal Explants Preparation

Dog tracheas were collected from 3 healthy Beagles (Charles River Laboratories) used as negative controls in other, unrelated studies. Briefly, tracheas were aseptically collected immediately upon euthanasia and transported in pre-warmed medium as previously described (Gonzalez et al., 2014, J Virol, 88(16): 9208-9219). Tracheas were washed 6 times over a period of 4 hours and maintained at 33° C., 5% $CO_2$, and 95% humidity between washes. The connective tissue was then removed and the trachea was open lengthwise. Each tracheal ring was divided in four 0.5-by 0.5-cm explants and placed onto a sterile section of filter paper on top of an agarose plug, epithelium facing upwards.

Explants Infection and Virus Quantification

Explants were infected with a dose of 200 PFU 24 hours after dissection (designed as day 0). Culture medium was used for mock-infected explants. Inoculated explants were sampled for bead clearance, histology, and viral replication at days (D) 0, 1, 3 and 5 p.i. Viral titers were determined by standard plaque assays on MDCK cells and revealed by immunostaining of plaques.

Estimation of Bead Clearance Time

Ciliary beating of the tracheal explants was checked at indicated times p.i. Five microliters of polystyrene microsphere beads (Polysciences, Northampton, UK) was placed on the apical surface of the explants and bead clearance was evaluated by eye every 5 min. Ciliary beating was considered efficient when the beads were completely cleared to one side of the explants by coordinated cilia movement.

Histological Analysis and Immunohistochemistry

After collection, the explants were fixed in 10% buffered formalin for a minimum of 48 hours. Subsequently, 4 μm sections of paraffin embedded tissue were either stained with Haematoxylin and Eosin or deparaffinized and hydrated for viral nucleoprotein (NP) staining using standard procedures. Briefly, sections were incubated overnight at 4° C. with a mouse MAb anti-NP (HB-65) diluted in 10% normal goat serum. Immunohistochemistry was performed using the Dako supervision system according to the manufacturer protocol, and slides were counterstained with Mayer's haematoxylin. Histological images were captured with the cellD software (Olympus).

The results of the experiments are now described.

Generation of Recombinant H3N8 CIVs with Truncated NS1 Proteins

H3N8 CIVs containing a full-length (WT), truncations (NS1-73, NS1-99, and NS1-126) or a deletion (ΔNS1) of the NS1 protein (Feng et al., 2015, J Virol, 89:6860-6873, Martinez-Sobrido et al., 2010, Journal of visualized experiments, doi: (42)10.3791/2057) were generated by reverse genetics (FIG. 1A). Both deletions and stop codons in the NS1 open reading frame were included, as well as unique restriction sites into each modified viral NS segment (FIG. 1B) (Quinlivan et al., 2005, J Virol, 79:8431-8439). Importantly, the open reading frame of the H3N8 CIV NEP was not altered in any of the recombinant CIVs. The evaluation of NS1 protein expression levels by Western blot was demonstrated using a polyclonal antibody generated against the first 73 amino acids of NS1 A/swine/Texas/4199-2/98 (Solorzano et al., 2005, J Virol, 79:7535-7543). Detection of NS1 expression from WT and NS1-126 CIVs was demonstrated, likely due to low protein stability and/or concentration in the latter clones (Quinlivan et al., 2005, J Virol, 79:8431-8439, Solorzano et al., 2005, J Virol, 79:7535-7543). The identities of the recombinant H3N8 CIVs were confirmed by analyzing the expression of the viral NS vRNA by RT-PCR, revealing products with sizes of 890 (WT), 812 (NS1-126), 731 (NS1-99), 653 (NS1-73) and 424 (ΔNS1) nucleotides (FIG. 1C), corresponding to the different recombinant NS segments. The influenza NP vRNA and the canine GAPDH mRNA were also evaluated by RT-PCR from the same samples, which served as controls. Altogether, the data demonstrated the nature of the generated recombinant NS1 mutant H3N8 CIVs.

Growth Properties of Recombinant H3N8 CIVs in Tissue Culture

The replicative properties of the mutant NS1 H3N8 CIVs were examined using multicycle growth curves at 33° C. or 37° C. in MDCK cells infected at a low MOI (0.001) (FIG. 2). Viruses in culture supernatants collected at 24, 48, 72 and 96 h p.i. were titrated using immunofocus assay (fluorescent forming units, FFU/ml). All the viruses containing truncated versions of NS1 (CIV NS1-126, NS1-99 and NS1-73) displayed replication kinetics comparable to that of WT H3N8 CIV at both 37° C. and 33° C. (FIG. 2A and FIG. 2B, respectively). In contrast, ΔNS1 H3N8 CIV replication was significantly affected at 37° C. (FIG. 2A) but not at 33° C. (FIG. 2B) for NS1 deficient influenza viruses (Falcon et al., 2005, The Journal of general virology, 86:2817-2821). Plaque sizes of WT and NS1-truncated H3N8 CIVs in MDCK cells at 33° C. were consistent with the virus growth kinetics at that temperature (FIG. 2C). Comparable plaque sizes for the WT and NS1 truncated H3N8 CIVs were observed, while the ΔNS1 CIV showed smaller plaques. The evaluation of the plaque phenotype of the recombinant H3N8 CIVs at 37° C. could not be demonstrated, since none of the viruses plaque at this temperature. The data demonstrates that the NS1 mutant H3N8 CIVs can be propagated to levels comparable to those of WT virus in MDCK cells at permissive (33° C.) temperatures.

Induction of IFN By Recombinant H3N8 CIVs

Figures 3A, 3B, 3C, 3D, 3E:
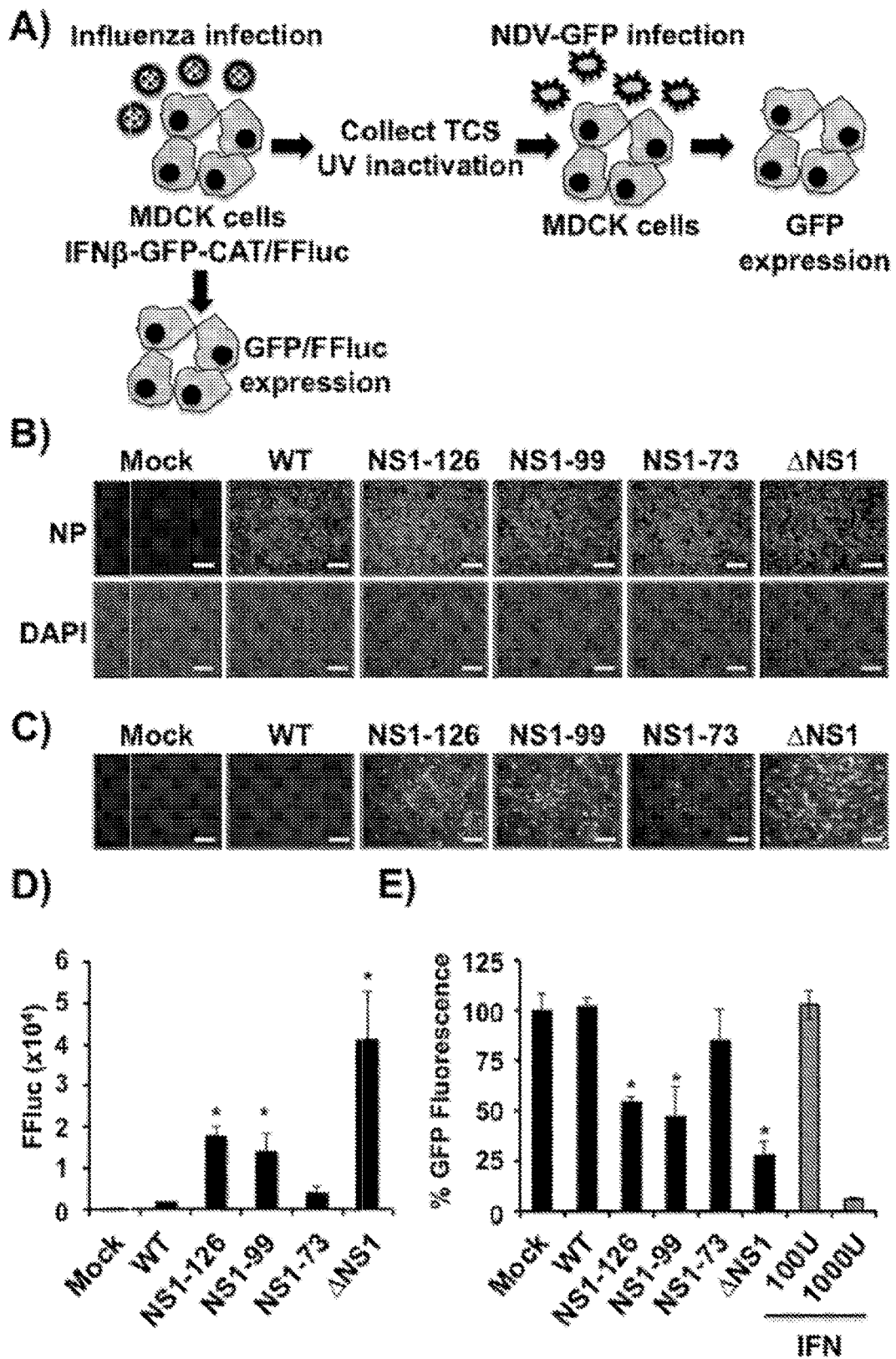
FIG. 3A through FIG. 3E, depicts the results of experiments evaluating the activation of the IFN-$\beta$ promoter by CIV WT and NS1-truncated viruses.

One of the main functions of influenza NS1 protein is to counteract the type I IFN response during viral infection (Garcia-Sastre et al., 1998, Virology, 252:324-330, Hale et al., 2008, Virology, 89:2359-2376). The ability of NS1 mutant H3N8 CIVs to counteract the IFN response was demonstrated by two complementary bioassays (FIG. 3A). The cell-based assay involved MDCK cells constitutively expressing GFP-CAT and FFluc reporter genes under the control of the IFNβ promoter (MDCK IFNβ GFP-CAT/FFluc) (Hai et al., 2008, J Virol, 82:10580-10590). Those cells were mock infected or infected (MOI 3) with either WT or mutant H3N8 CIVs, and IFNβ promoter activation was evaluated. Further, IFN in culture supernatants from the same virus-infected MDCK cells was assessed using a virus-based assay, where inhibition of rNDV-GFP infection was evaluated (Nogales et al., 2014, J Virol, 88:10525-10540). Comparable levels of viral infection were verified by immunofluorescence using an anti-NP HB-65 MAb (FIG. 3B). For the cell-based assay, at 12 h p.i, activation of the IFNβ promoter in MDCK IFNβ GFP-CAT/FFluc cells was assessed by evaluating GFP expression (FIG. 3C) and FFluc activity (FIG. 3D). GFP expression was detected only in cells infected with the NS1 mutant CIVs, but not in mock-infected or WT H3N8 CIV-infected cells (FIG. 3C), indicating that CIV WT infection (and NS1 protein) is able to counteract the IFN response during viral infection. This result with GFP was further confirmed and quantified by assessing FFluc activities from infected-cells lysates (FIG. 3D). Differences in the activation of the IFNβ promoter and induction of FFluc during infection with the NS1 truncated H3N8 CIVs were observed. A stronger activation of the IFNβ promoter was observed in H3N8 CIV ΔNS1 infected cells, followed by NS1-126, NS1-99 and NS1-73 CIVs. The data demonstrated that CIVs encoding truncated or a deleted NS1 protein have different capabilities to counteract IFN activation. These results were confirmed by evaluating the presence of IFN in supernatants of virus-infected cells using virus-based bioassay (Nogales et al., 2014, J Virol, 88:10525-10540). In this assay, the level of IFN in supernatants from virus-infected cells resulted in inhibition of NDV infection and, therefore, GFP expression (Martinez-Sobrido et al., 2009, J Virol, 83:11330-11340, Martinez-Sobrido et al., 2006, J Virol, 80:9192-9199, Park et al., 2003, J Virol, 77:1501-1511). In cells pre-treated with culture supernatants from mock- and WT H3N8 CIV-infected cells, rNDV-GFP replicated efficiently (FIG. 3E). The levels of rNDV-GFP infection decreased in MDCK cells pre-treated with culture supernatants from NS1 mutant H3N8 CIV-infected cells. NDV inhibition was stronger in cells pre-treated with supernatants from H3N8 CIV ΔNS1 infected MDCK cells, followed by NS1-126, NS1-99 and NS1-73, (FIG. 3E). The data demonstrated that infection with the H3N8 CIV NS1 mutants induced different levels of IFN, where ΔNS1 induced higher levels of IFN than the NS1 truncated CIVs.

CIV H3N8 NS1 Mutants Are Attenuated In Vivo

Figure 4:
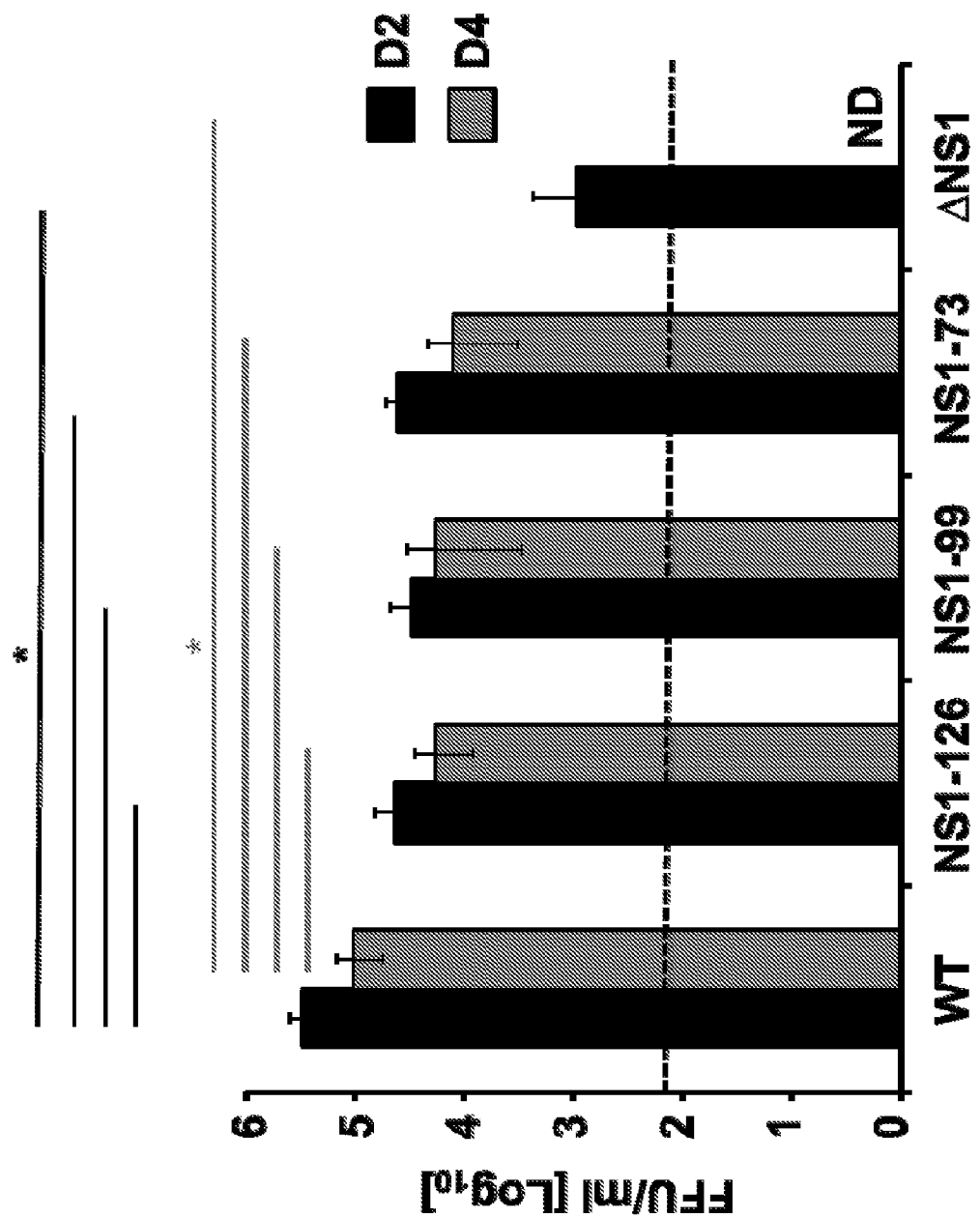
FIG. 4 depicts the results of experiments evaluating the attenuation of NS1-truncated CIV: 5- to 7-week-old C57BL/6 female mice (N=6) were infected i.n. with 1×10$^5$ PFU of WT CIV or NS1 mutants (NS1-126, -99, -73 and $\Delta$NS1). Three mice were euthanized at days 2 and 4 post-infection and lungs were harvested for virus titrations using an immunofocus assay (FFU/ml). The dotted black line indicates the limit of detection (200 FFU/ml). ND, virus not detected. * (black lines for D2 and grey lines for D4) indicate P values <0.05 using a Student's t test from Microsoft Excel.

As the different NS1 truncated H3N8 CIVs presented defects in counteracting the innate immune IFN response (FIG. 3) it was next demonstrated whether the NS1 mutant H3N8 CIVs was attenuated in mice. No signs or symptoms of CIV infection were detected after intranasal (i.n) administration of $10^5$ PFU WT H3N8 CIV. Viral attenuation was determined by the viral titers of H3N8 CIV (and the NS mutants) at days 2 (N=3) and 4 (N=3) p.i in the lungs of infected mice. All H3N8 CIV NS1 mutants replicated efficiently in the lungs of infected mice, although ~1 log lower than WT H3N8 CIV (FIG. 4). ΔNS1 H3N8 CIV was highly defective and was only detected at day 2 p.i. (~2.5 log lower titers than H3N8 CIV WT). These results demonstrate that NS1 mutant H3N8 CIVs are attenuated in mice, as compared to WT CIV, with ΔNS1 H3N8 CIV showing the highest level of attenuation.

Figures 5A, 5B:
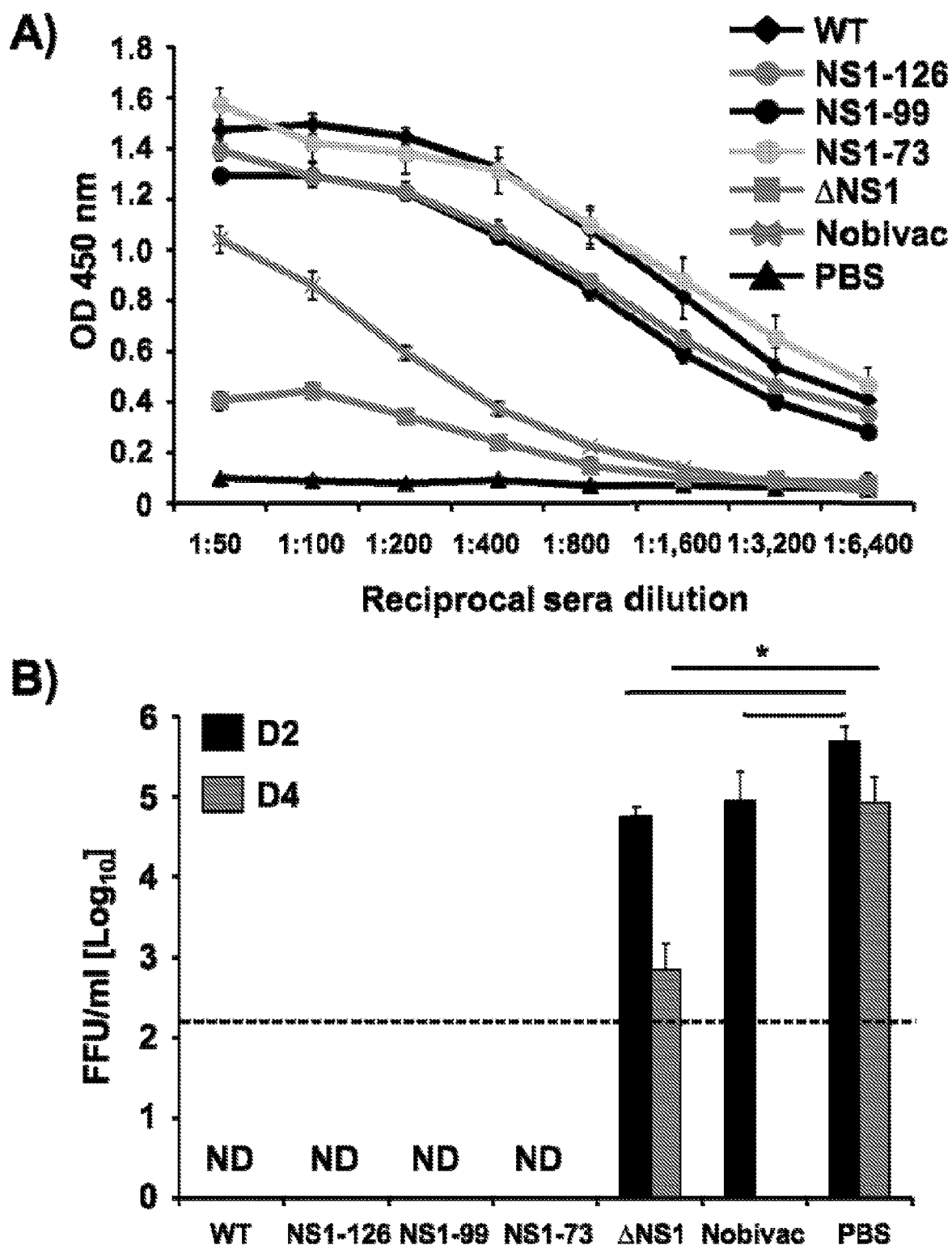
FIG. 5B depicts the results of experiments evaluating the immunogenicity and protection efficacy of NS1 mutant H3N8 CIVs. Female 5- to-7-week-old C57BL/6 mice were vaccinated with the H3N8 CIV IIV (Nobivac; 100 µl i.m), or with 1×10$^3$ PFU of WT or mutant H3N8 CIVs ($\Delta$NS1, NS1-73, NS1-99 and NS1-126, i.n.); or mock vaccinated with PBS.
(FIG. 5A) Induction of humoral responses: At 14 days post-vaccination, mice were bled and sera were collected and evaluated by ELISA for IgG antibodies against total WT H3N8 CIV proteins using cell extracts of MDCK-infected cells. Mock-infected cell extracts were used to evaluate the specificity of the antibody response. OD, optical density. Data represent the means +/− SDs of the results for 4 individual mice.

Vaccination with H3N8 NS1 Mutant CIVs Elicits Protective Immunity against WT H3H8 CIV in Mice Inoculated mice (N=6) i.n. with $10^3$ PFU of WT or NS1 mutant (NS1-73, NS1-99, NS1-126 and ΔNS1) H3N8 CIVs or mock vaccinated with PBS was used to demonstrate the immunity generated in mice. A group of mice (N=6) were vaccinated i.m. with 100 μl of Nobivac as a control (Deshpande et al., 2009, Veterinary therapeutics: research in applied veterinary medicine, 10:103-112). The humoral immune responses induced upon vaccination with the NS1 truncated H3N8 CIVs (FIG. 5A) was determined. Serum samples taken two weeks post-vaccination were evaluated by ELISA using cell lysates from mock- or CIV H3N8-infected MDCK cells (FIG. 5A). All mice vaccinated with the NS1-truncated H3N8 CIVs induced significant antibody titers against WT H3N8 CIV, similar to those induced by WT H3N8 CIV infection (FIG. 5A). It was also demonstrated that total antibody titers from mice vaccinated with the ΔNS1 H3N8 CIV were lower than those observed with the NS1 truncated CIVs. Titers induced by vaccination with the truncated or deleted NS1H3N8 CIVs were higher than those obtained with the commercial vaccine (FIG. 5A). Similar results were demonstrated when the HA inhibiting titers were evaluated against CIV H3N8 using a conventional HAI assay (Table 3). The HAI titers in mice infected with the NS1-truncated H3N8 CIV were slightly lower than those observed in WT CIV H3N8 infected mice, but higher than those observed with the inactivated vaccine (Table 3).

It was then demonstrated that a single immunization with the mutant H3N8 CIVs induced protection against challenge with WT H3N8 CIV. Mice vaccinated with the NS1 mutant H3N8 CIVs were challenged two weeks after vaccination, and then evaluated for the challenge virus at days 2 (N=3) and 4 (N=3) p.i (FIG. 5B). In PBS inoculated mice it was detected high titers of CIV WT H3N8 at days 2 (~106) and 4 (~105) p.i. In contrast, virus in mice vaccinated with the NS1-truncated viruses at either time point (FIG. 5B) were undetected. Mice vaccinated with the H3N8 ΔNS1 CIV or the inactivated vaccine showed similar viral titers at day 2 p.i, and those were slightly lower than the titers in the PBS vaccinated group. At day 4 p.i, the presence of WT H3N8 CIV in the lungs of IIV-vaccinated mice was not detected, but the presence of WT H3N8 CIV in the lungs of the ΔNS1 H3N8 CIV vaccinated group (FIG. 5B) was. The protection results correlate with the ability of these NS1 truncated H3N8 CIV to induce total (FIG. 5A) or neutralizing (Table 3) immune responses.

CIV H3N8 NS1 Mutants Are Attenuated Ex Vivo

Figures 6A, 6B, 6C, 6D:
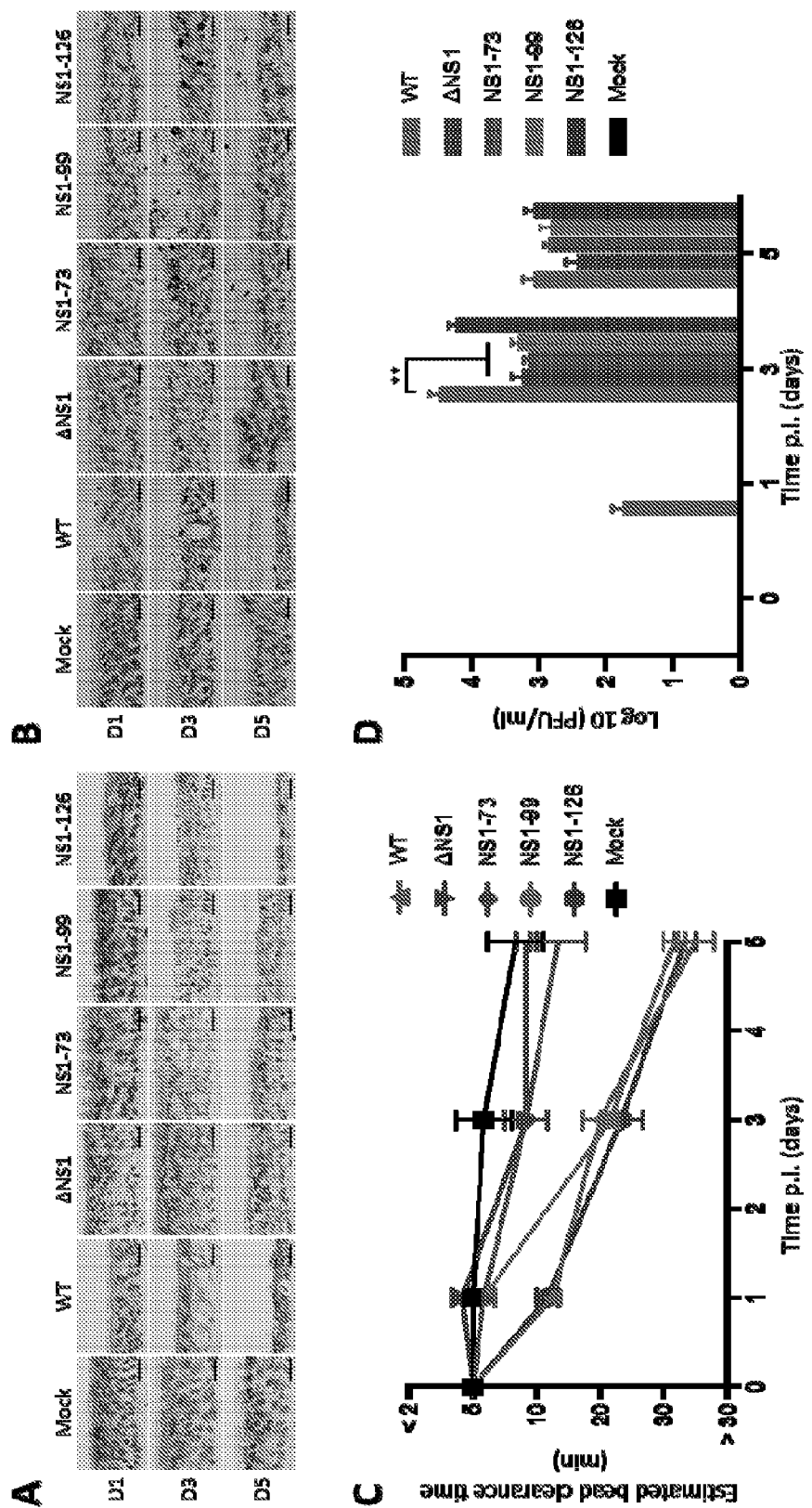
FIG. 6A through FIG. 6B, depicts the results of experiments of ex vivo infection of canine tracheal explants with A/canine/New York/2009 H3N8 WT or mutant ($\Delta$NS1, NS1-73, NS1-99 and NS1-126) viruses.
(FIG. 6C) Graphical representation of bead clearance assays in infected and control explants. Lines represent the average time to clear the beads in three independent experiments. Error bars represent SEM.
(FIG. 6D) Growth kinetics of H3N8 CIVs (WT and mutants) in canine tracheal explants. Vertical bars represent average from three independent experiments. Error bars represent SEM.

To determine the effect of NS1 truncations in CIV H3N8 pathogenesis at the site of infection within the natural host, dog tracheal explants were infected with CIV WT and mutants, as described above. The viruses were titrated at different times p.i., histological lesions changes in ciliary function were assessed and the presence of virus in the tissues was determined using immunohistochemistry. While mock-infected explants kept their normal morphology throughout the study period, infected explants showed major histopathological changes, including loss of cilia and destruction of the epithelium followed by desquamation of cells and subsequent decrease in epithelium thickness (FIG. 6A). Changes were evident by day 1 p.i. for CIV H3N8 WT. H3N8 CIV NS1-126, and to less extent the NS1-99, resembled the WT virus in terms of histological damage (FIG. 6A) and viral antigen expression (FIG. 6B). In contrast, ΔNS1 and the NS1-73 mutant H3N8 CIVs showed an attenuated phenotype as the epithelium exhibited less destruction of cilia and cells (FIG. 6A). Moreover, immunostaining for the viral nucleoprotein (NP) showed that fewer cells were infected with NS1-73 and ΔNS1 H3N8 CIVs (FIG. 6B). Consistent with this, ciliary function was significantly reduced for WT, NS1-126 and 1-99 H3N8 CIVs (FIG. 6C), but only slightly affected compared to mock-infected tracheal explants for NS1-73 and ΔNS1 H3N8 CIVs (FIG. 6C). In terms of virus replication, all H3N8 CIV NS1 mutants were able to replicate in the dog trachea, although viral kinetics between them and WT H3N8 CIV differed (FIG. 6D). H3N8 CIV WT virus was detected from day 1 and peaked at day 3 p.i., whereas infectious virus was only detectable from day 3 p.i. for all H3N8 CIV NS1 mutants. In addition, the peak of virus growth of NS1-73, NS1-99 and ΔNS1 H3N8 CIVs was significantly lower than for WT H3N8 CIV. These results indicate that NS1 truncations attenuate H3N8 CIV ex vivo and that the level of attenuation is influenced by the magnitude of the NS1 truncation.

H3N8 NS1 Mutant CIV Can Provide Protection against H3N2 CIV

Figure 7:
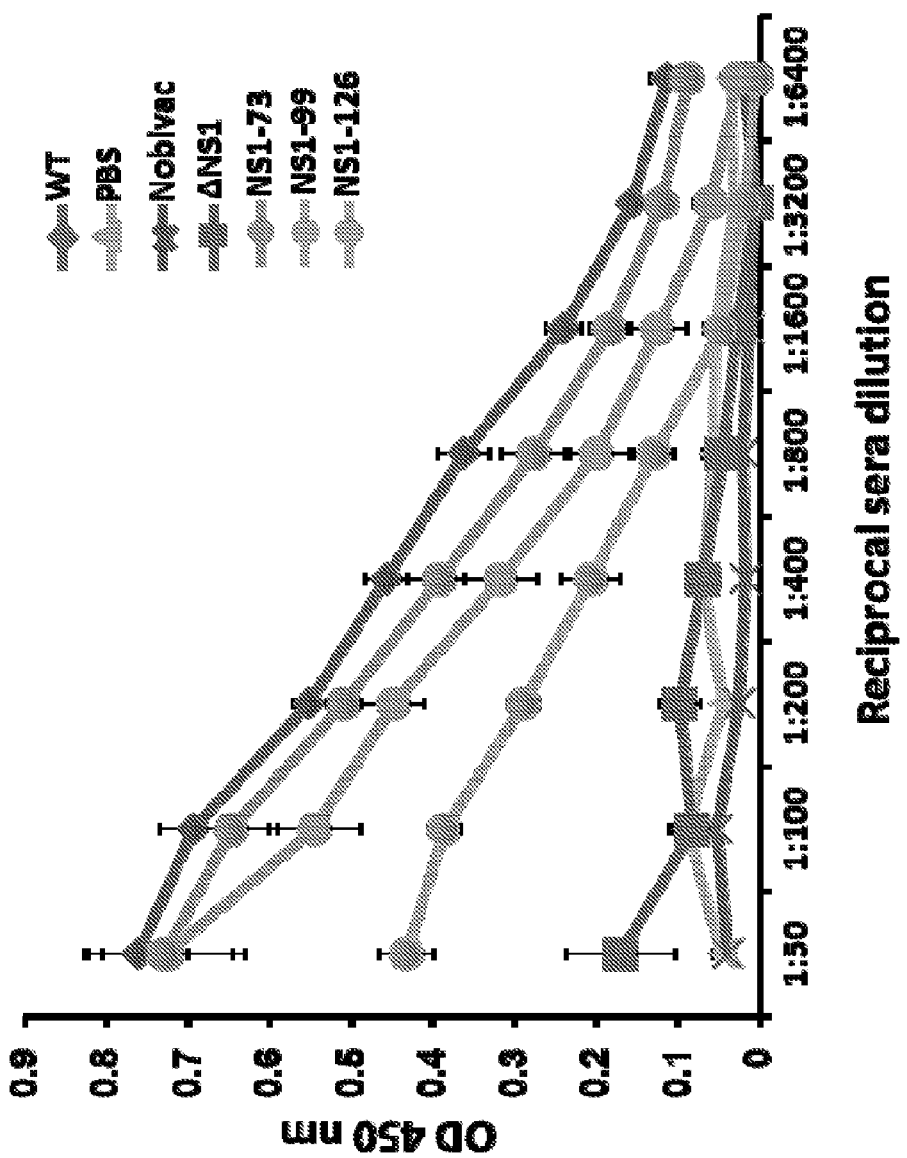
FIG. 7 depicts the results of experiments evaluating the induction of humoral responses by NS1-truncated CIV vaccination. Female 6- to-8-week-old C57BL/6 mice were immunized intranasally with the H3N8 CIV inactivated vaccine (Nobivac; 100 uμ intramuscular), or with $1\times10^3$ PFU of H3N8 CIV wild-type (WT) or NS1-truncated viruses (ΔNS1, NS1-73, NS1-99 and NS1-126); or mock vaccinated with PBS. At 14 days post-infection, mice were bled and the sera were collected and evaluated by ELISA for IgG antibodies against total influenza virus protein using cell extracts of MDCK cells infected with CIV H3N2 wild-type (A/Ca/IL/41915/2015). Mock-infected cell extracts were used to evaluate the specificity of the antibody response. Data represent the means +/− SDs of the results for 4 individual mice.
Figure 8:
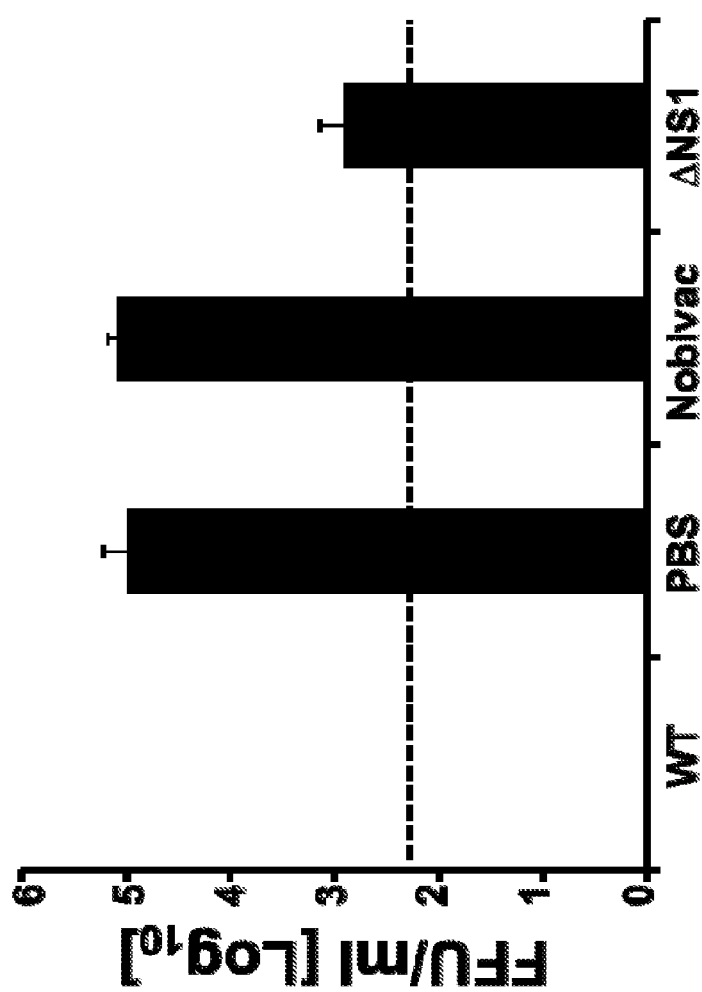
FIG. 8 depicts the results of experiments evaluating the protection efficacy of CIV ΔNS1 against CIV H3N2: Female 6- to-8-week-old C57BL/6 mice (n=6) were immunized intranasally with the H3N8 CIV inactivated vaccine (Nobivac; 100 μl intramuscular), or with $1\times10^3$ PFU of CIV wild-type (WT) or ΔNS1 or mock vaccinated with PBS. Two weeks post-vaccination, mice were challenged with $1\times10^5$ PFU of CIV H3N2 wild-type (A/Ca/IL/41915/2015). To evaluate viral lung replication, mice were sacrificed at days 3 (n=3) post-challenge and lungs were harvested, homogenized, and used to quantify viral titers by immunofocus assay (FFU/ml) using an anti-NP MAb (HB-65). Dotted black lines indicate limit of detection (200 FFU/ml). Data represent the means +/− SDs.

Experiments were conducted to examine if the H3N8 NS1 mutant CIV can provide protection against H3N2 CIV. First, experiments were conducted to evaluate the induction of humoral responses by NS1-truncated CIV vaccination. Female 6- to-8-week-old C57BL/6 mice were immunized intranasally with the H3N8 CIV inactivated vaccine (Nobivac; 100 ul intramuscular), or with 1×10³ PFU of H3N8 CIV wild-type (WT) or NS1-truncated viruses (ΔNS1, NS1-73, NS1-99 and NS1-126); or mock vaccinated with PBS. At 14 days post-infection, mice were bled and the sera were collected and evaluated by ELISA for IgG antibodies against total influenza virus protein using cell extracts of MDCK cells infected with CIV H3N2 wild-type (A/Ca/IL/41915/2015). Mock-infected cell extracts were used to evaluate the specificity of the antibody response. It was observed that, replicating-competent, NS1 deficient or truncated CIV induce better immune responses that the inactivated H3N8 CIV inactivated vaccine (FIG. 7). Next, experiments were conducted to evaluate the protection efficacy of H3N8 NS1 mutant CIV against H3N2 CIV. Female 6- to-8-week-old C57BL/6 mice (n=6) were immunized intranasally with the H3N8 CIV inactivated vaccine (Nobivac; 100 ul intramuscular), or with 1×10³ PFU of CIV wild-type (WT) or ΔNS1 or mock vaccinated with PBS. Two weeks post-vaccination, mice were challenged with 1×10⁵ PFU of CIV H3N2 wild-type (A/Ca/IL/41915/2015). To evaluate viral lung replication, mice were sacrificed at days 3 (n=3) post-challenge and lungs were harvested, homogenized, and used to quantify viral titers by immunofocus assay (FFU/ml) using an anti-NP MAb (HB-65). Dotted black lines indicate limit of detection (200 FFU/ml). Even ΔNS1, inducing a weaker immune response as compared to mice intranasally infected with the NS1-truncated viruses NS1-73, NS1-99 and NS1-126; is able to confer better protection against the new H3N2 CIV than the inactivated influenza vaccine (FIG. 8).

Vaccination with H3N8 NS1 Mutant CIVs Elicits Protective Immunity against WT H3H8 CIV in Mice Currently, there are two subtypes of CIV co-circulating in the US, an equine-origin CIV H3N8, and an avian-origin CIV H3N2. H3N8 CIV has been circulating widely in the dog population for at least 16 years (Crawford et al., 2005, Science, 310:482-485, Yoon et al., 2005, Emerging infectious diseases, 11:1974-1976), particularly in animal shelters (Crawford et al., 2005, Science, 310:482-485, Holt et al., 2010, Journal of the American Veterinary Medical Association, 237:71-73, Pecoraro et al., 2013, Journal of veterinary diagnostic investigation, 25:402-406). Although CIV H3N2 appeared to be limited to Asia, in 2015 there was an outbreak of CIV H3N2 in the Chicago area that has been reported later on in more than 25 states in the US (Newbury et al., 2016, Journal of the American Veterinary Medical Association, 248:1022-1026). The emergence and establishment of these two viral strains create many opportunities for CIV exposure to humans and other species. Moreover, IAVs that belong to the H3 subtype are the most ubiquitous as they have been found in various different hosts including humans, pigs, horses, dogs, cats, seals, poultry and wild aquatic birds (Bean et al., 1992, J Virol, 66:1129-1138, Bush et al., 1999, Molecular biology and evolution, 16:1457-1465, Parrish et al., 2015, J Virol, 89:2990-2994, Song et al., 2008, Emerging infectious diseases, 14:741-746, Song et al., 2015, The Journal of general virology, 96:254-258). Human IAVs have not become established in dogs despite serological evidence of exposure and infection (Dundon et al., 2010, Emerging infectious diseases, 16:2019-2021, Ramirez-Martinez et al., 2013, Influenza and other respiratory viruses, 7:1292-1296).

It has been demonstrated that various human influenza viruses such as PR8 (H1N1), Udorn/72 (H3N2) and A/California/04/09 (pdm09, H1N1) replicate in dog tracheas at levels similar to those observed for CIV H3N8 (Gonzalez et al., 2014, J Virol, 88:9208-9219), and viable reassortments generated by reverse genetics between CIV H3N8 and pdm09 viruses have been reported (Gonzalez et al., 2014, J Virol, 88:9208-9219). Therefore, dogs act as an intermediate host and "mixing vessels" for genetic reassortment between human and avian viruses, facilitating the generation of novel human influenza virus strains and the initiation of influenza pandemics.

Currently, there are only inactivated vaccines to control H3N8 CIV in dogs. The vaccine is intended as an aid in the control of the disease associated with viral infection. Although the vaccine may not completely prevent H3N8 CIV infection, efficacy trials have shown that it may significantly decrease the signs, severity and spread of viral infection, including the level of damage to the lungs or the duration and degree of viral shedding (Deshpande et al., 2009, Veterinary therapeutics: research in applied veterinary medicine, 10:103-112). These benefits are similar to those provided by IIV used in other species, including humans (De Villiers et al., 2009, Vaccine, 28:228-234). CIV LAIV may afford better and faster protection, as it has been shown with other influenza vaccines (Belshe et al., 2007, The New England journal of medicine, 356:685-696, Gorse et al., 1991, Scandinavian journal of infectious diseases, 23:7-17, Pica et al., 2013, Annual review of medicine, 64:189-202.).

Influenza NS1 protein is a multifunctional viral factor which displays several regulatory functions during virus infection and can antagonize the IFN response (Randall et al., 2008, The Journal of general virology, 89:1-47). In these experiments, for the first time, it has been demonstrated that the generation of CIVs with truncations or a deletion of the NS1 protein constitute LAIV candidates.

It was demonstrated that H3N8 CIV WT, NS1 mutant viruses all displayed similar growth kinetics at 33° C., while the CIV ΔNS1 demonstrated a slightly reduced growth. These results correlated with the virus plaque size phenotypes. At 37° C., the NS1-truncated viruses demonstrated comparable replication kinetics to that of H3N8 CIV WT, but the ΔNS1 replication was highly impaired. Cells infected with ΔNS1 CIV induced IFN production at higher levels, followed by the NS1-126, NS1-99 and NS1-73 viruses, and the WT H3N8 CIV. Similar truncations of the NS1 protein in swine or equine influenza viruses generated comparable results (Quinlivan et al., 2005, J Virol, 79:8431-8439, Solorzano et al., 2005, J Virol, 79:7535-7543). It has been demonstrated that the different levels of attenuation observed between the NS1 mutants is that the truncated constructs display different RNA and/or protein stability, affecting the levels of NS1 and NEP expression (Quinlivan et al., 2005, J Virol, 79:8431-8439, Solorzano et al., 2005, J Virol, 79:7535-7543). In vivo the ΔNS1 H3N8 CIV demonstrated the most attenuation in viral growth in mice, followed by the NS1 truncated viruses. These results illustrate the differences observed in pigs with swine influenza viruses encoding the same truncated NS1 proteins (NS1-73, NS1-99 and NS1-126) (Solorzano et al., 2005, J Virol, 79:7535-7543).

The NS1 mutant viruses and the inactivated commercial vaccine conferred protection against challenge with WT CIV H3N8, as demonstrated by the induction of antibodies specific for the virus and reduced virus titers in the vaccinated mice. Importantly, virus replication was not detected in the lungs of mice immunized with the NS1 truncated H3N8 CIV. Furthermore, the lungs from animals vaccinated with ΔNS1 virus or the inactivated vaccine demonstrated high viral titers at day 2 post-challenge (similar to those of mock-vaccinated mice), demonstrating that vaccinated animals shed and transmit virus at early times after natural infection. It should be noted that H3N8 CIV was cleared by day 4 post-challenge in animals vaccinated with Nobivac. Vaccination also induced high and comparable levels of IgG antibodies in sera against the parental CIV WT and the NS1-truncated viruses. The ΔNS1 did not elicit high levels of antibodies and the sera from mice immunized with Nobivac elicited intermediate values, demonstrating that the mutants lacking regions of NS1 protein induce better immune B cell responses in mice than those obtained with current commercial inactivated vaccines.

This report is the first description of a CIV H3N8 LAIV generated by reverse genetics whose attenuation mechanism is based on truncations or total deletion of the NS1 protein. The viruses demonstrated attenuation, while retaining immunogenicity (Hussain et al., 2010, Vaccine, 28:3848-3855, 15).

TABLE 3

Immunogenicity of NS1-truncated viruses

| Immunization and dose[a] | | Mean (SD) serum HAI titer[b] |
|---|---|---|
| PBS | — | ≤8 (ND) |
| WT | 10³ PFU | 215.3 (64) |
| NS1-73 | 10³ PFU | 128 (0) |
| NS1-99 | 10³ PFU | 107.6 (32) |
| NS1-126 | 10³ PFU | 90.5 (36.9) |
| ΔNS1 | 10³ PFU | 22.6 (9.23) |
| Nobivac | 100 μl | 26.9 (8) |

[a]Virus was administered intranasally to anesthetized mice (n = 4), Nobivac was administered intramuscularly, and sera were collected at 14 days postinfection.
[b]Four HAU of the WT virus was incubated with 2-fold serial dilutions of the indicated sera.
ND, not determined.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An immunological composition comprising a canine influenza virus (CIV), wherein the CIV comprises one or more mutations in segment 8 of the viral genome, and wherein segment 8 comprises a nucleic acid sequence selected from the group consisting of SEQ ID NO: 1, SEQ ID NO: 2, SEQ ID NO: 3, and SEQ ID NO: 4.

2. The composition of claim 1, wherein the CIV comprises one or more mutations in segment 8, which encodes a truncation mutant of NS1.

3. The composition of claim 2, wherein the truncation mutant of NS1 is selected from the group consisting of NS1-126, NS1-99, and NS1-73.

4. The composition of claim 2, wherein the truncation mutant of NS1 comprises an amino acid sequence selected from the group consisting of SEQ ID NO: 5, SEQ ID NO: 6, and SEQ ID NO: 7.

5. The composition of claim 1, wherein the CIV comprises one or more mutations in segment 8 such that NS1 is not expressed.

6. The composition of claim 1, wherein the CIV is derived from H3N8 subtype of influenza A virus.

7. The composition of claim 1, wherein the composition is used for inducing an immune response against a canine influenza virus in a subject.

8. A method for inducing an immune response against a canine influenza virus in a subject, the method comprising administering to the subject an immunological composition comprising a canine influenza virus (CIV), wherein the CIV comprises one or more mutations in segment 8 of the viral genome, and wherein the segment 8 comprises a nucleic acid sequence selected from the group consisting of SEQ ID NO: 1, SEQ ID NO: 2, SEQ ID NO: 3, and SEQ ID NO: 4.

9. The method of claim 8, wherein the CIV comprises one or more mutations in segment 8, which encodes a truncation mutant of NS1.

10. The method of claim 9, wherein the truncation mutant of NS1 is selected from the group consisting of NS1-126, NS1-99, and NS1-73.

11. The method of claim 9, wherein the truncation mutant of NS1 comprises an amino acid sequence selected from the group consisting of SEQ ID NO: 5, SEQ ID NO: 6, and SEQ ID NO: 7.

12. The method of claim 8, wherein the CIV comprises one or more mutations in segment 8 such that NS1 is not expressed.

13. The method of claim 8 wherein the CIV is derived from H3N8 subtype of influenza A virus.

14. The method of claim 8, wherein the subject does not have canine influenza, and wherein the method induces immunity against one or more of: influenza A virus subtype H3N8 and influenza A virus subtype H3N2.

15. The method of claim 8, wherein the subject is infected with at least one or more of: influenza A virus subtype H3N8 and influenza A virus subtype H3N2;

and wherein the method induces a therapeutic immune response.

16. The method of claim 8, wherein the immunological composition is administered intranasally, intratracheally, orally, intradermally, intramuscularly, intraperitoneally, intravenously, or subcutaneously.

17. The method of claim 8, wherein the subject is a dog.

* * * * *